US012806145B2

(12) United States Patent
Moreadith et al.

(10) Patent No.: US 12,806,145 B2
(45) Date of Patent: Nov. 24, 2026

(54) POLY(OXAZOLINE) CONJUGATES WITH PENDANT CATIONIC GROUPS AND LIPID NANOPARTICLES AND POLYPLEXES INCLUDING SAME

(71) Applicant: Serina Therapeutics (AL), Inc., Hunstville, AL (US)

(72) Inventors: Randall Moreadith, Huntsville, AL (US); J Milton Harris, Huntsville, AL (US); Kunsang Yoon, Madison, AL (US); Zhihao Fang, Madison, AL (US); Rebecca Weimer, Huntsville, AL (US); Wookhyun Kim, Madison, AL (US); Kelley Smith, Madison, AL (US)

(73) Assignee: Serina Therapeutics (AL), Inc., Huntsville, AL (US)

( * ) Notice: Subject to any disclaimer, the term of this patent is extended or adjusted under 35 U.S.C. 154(b) by 196 days.

(21) Appl. No.: 18/743,721

(22) Filed: Jun. 14, 2024

(65) Prior Publication Data

US 2025/0017857 A1 Jan. 16, 2025

Related U.S. Application Data

(60) Provisional application No. 63/521,164, filed on Jun. 15, 2023.

(51) Int. Cl.
*A61K 9/1272* (2025.01)

(52) U.S. Cl.
CPC .................................. *A61K 9/1272* (2013.01)

(58) Field of Classification Search
None
See application file for complete search history.

(56) References Cited

U.S. PATENT DOCUMENTS

| | | | |
|---|---|---|---|
| 4,235,871 A | 11/1980 | Papahadjopoulous et al. |
| 11,318,195 B2 | 5/2022 | Sahin et al. |
| 2022/0249695 A1 | 8/2022 | Harris et al. |
| 2022/0276232 A1 | 9/2022 | Yamauchi et al. |
| 2022/0370357 A1 | 11/2022 | Stanton et al. |

FOREIGN PATENT DOCUMENTS

| | | | |
|---|---|---|---|
| CN | 115626983 A * | 1/2023 | ............. C08G 73/00 |
| WO | 2023073228 | 5/2023 | |

OTHER PUBLICATIONS

Mahand et al. European Polymer Journal (2022), 178, 111484 (20 pages).*

Siedenbiedel et al., "Antimicrobial Polymers in Solution and on Surfaces: Overview and Functional Principles", Polymers, Jan. 9, 2012, vol. 4, pp. 46-71; p. 52, Figure 5.

International Search Report and Written Opinion dated Nov. 12, 2024 of corresponding International Patent Application No. PCT/US24/34074.

Thomas, T. J., Heidar-Ali Tajmir-Riahi, and C. K. S. Pillai (2019). "Biodegradable Polymers for Gene Delivery" Molecules 24, No. 20: 3744. https://doi.org/10.3390/molecules24203744.

Rinkenauer AC et al. (Mar. 2015): A Cationic Poly(2-oxazoline) with High In Vitro Transfection Efficiency Identified by a Library Approach; Macromolecular Bioscience vol. 15, Issue 3, pp. 414-425 (https://doi.org/10.1002/mabi.201400334).

Zhu et al. (PLoS One. 2009; 4(4): e5009. Epub Apr. 6, 2009), pp. 1-4.

Bouten, P. J. M.; Hertsen, D.; Vergaelen, M.; Monnery, B. D.; Boerman, M. A.; Goossens, H.; Catak, S.; van Hest, J. C. M.; van Speybroeck, V.; Hoogenboom, R. Polym. Chem. 2015, 6, 514-518.

Szoka et al. PNAS 1978 vol. 75, 4194-4198.

* cited by examiner

*Primary Examiner* — Brian J Davis
(74) *Attorney, Agent, or Firm* — Bradley Arant Boult Cummings LLP

(57) ABSTRACT

Poly(oxazoline) conjugates with pendant cationic groups (cationic POZ) and lipid nanoparticles (LNPs) including cationic POZ used to facilitate delivery of an encapsulated payload. LNPs and polyplexes including cationic POZ and a nucleic acid payload such as, but not limited to, mRNA or modified mRNA are disclosed. Such LNPs have no immunogenicity or reduced immunogenicity as compared to a corresponding LNP containing an ionizable lipid.

17 Claims, 13 Drawing Sheets

POLY(OXAZOLINE) CONJUGATES WITH PENDANT CATIONIC GROUPS AND LIPID NANOPARTICLES AND POLYPLEXES INCLUDING SAME

FIELD OF THE INVENTION

The present disclosure relates to polyoxazoline (POZ) conjugates with pendent and terminal cationic groups (cationic POZ) and methods of synthesis. In addition, the present disclosure relates to lipid nanoparticles (LNPs) and polyplexes including cationic POZ and pharmaceutical compositions including such LNPs. LNPs and polyplexes incorporating oligonucleotides such as mRNA, DNA, saRNA and siRNA for delivery into living cells is also contemplated.

BACKGROUND OF THE INVENTION

Nucleic-acid (particularly mRNA)-based vaccines offer advantages over other vaccine technologies. Such vaccines can be produced with reduced development time and costs by employing a common manufacturing platform based on lipid nanoparticles (LNPs). In fact, the utility of LNPs for delivering mRNA to cells has been demonstrated in vaccines for Covid-19 (or SARS-CoV-2) to address the global pandemic that led to over 7 million deaths worldwide. Given the extraordinary burden on health care systems resulting from this viral disease and given the apparent wide utility of cellular delivery of mRNA for a range of diseases from cancer to influenza, there has been a large amount of work on understanding and improving LNP delivery of RNA.

As shown in FIG. 1, the basic structure of a LNP is accomplished by four components—(1) a sterol lipid (to provide flexibility, e.g., cholesterol), (2) a helper lipid (to provide structural integrity, e.g., such as distearoylphosphatidylcholine (DSPC)), (3) a polymer lipid (to stabilize the lipid nanoparticles and prevent fusion with other nanoparticles, e.g., a PEG-lipid or a POZ-lipid) and (4) an ionizable lipid (which complexes with the oligonucleotide). Most commonly, these components are prepared in two separate phases: 1) an aqueous phase (containing the RNA or other oligonucleotide) in buffers at approximately pH 4-5, and 2) an organic phase containing the cholesterol/DSPC/polymer-lipid/ionizable lipid components in ethanol. By employing microfluidic techniques during which the flow rates of these two phases are precisely controlled, LNPs can be prepared of a desired size that facilitates the delivery of the nucleic acid payload to produce a therapeutic response.

In this aspect, the ionizable lipid has been shown to be a critical component of LNPs. However, preclinical studies have suggested the ionizable lipid is implicated in a host of undesirable side effects from enhanced reactogenicity in patients (adverse events) to abnormal blood coagulation, which include binding of PEG-lipid nanoparticles following immunization with the approved mRNA vaccines, activation of the complement cascade, induction of proinflammatory pathways and accelerated clearance of the LNP. Thus, while the nature of the ionizable lipid may have profound effects on delivery and expression of the payloads (for example MC3 works exceptionally well for delivery of siRNA but generally not well for delivery of mRNA), the field is in need of developing technology that reduces or eliminates the undesirable side effects upon repeat dose administration that may be associated with the ionizable lipid. More specifically, there is a need in the art for a non-immunogenic (or at least markedly reduced immunogenic) replacement for the ionizable lipid without compromising the efficacy of the LNP.

Synthetic cationic polymers are being used as non-viral vectors in gene therapy. In this aspect, long DNA chains are collapsed into nanoparticles of 50-300 nm in size by condensation with polyamines such as poly(L-lysine), spermidine, and spermine (Thomas, T. J., Heidar-Ali Tajmir-Riahi, and C. K. S. Pillai (2019). "Biodegradable Polymers for Gene Delivery" Molecules 24, no. 20: 3744. https://doi.org/10.3390/molecules24203744). However, highly positively charged polymers with primary amines have high zeta-potential values and may cause cytotoxicity.

Polymer chains with secondary amines have been also used, and these include the polyethyleneimine (PEI) linear and branched polymers. These polymers have been shown to have high transfection efficiencies. For example, U.S. Pat. No. 11,318,195 describes polyplexes that were made with PEI of 5000 to 25000 Da molecular weight and single stranded RNA with N/P ratios of 2 to 15. The toxicity of free and pure PEI on HEK-293 cells shows an $IC_{50}$ of 77 μM. To reduce these toxic effects, these polymers have been co-polymerized with inert polymers such as polyethylene glycol (PEG), polysaccharides, dextran, polycaprolactone and polyglutamic acid.

Co-polymers of poly(methyl oxazoline) and poly(decenyl oxazoline) or poly(butenyl oxazoline) have been discussed. See, e.g., Rinkenauer A C et al. (March 2015): A Cationic Poly(2-oxazoline) with High In Vitro Transfection Efficiency Identified by a Library Approach; *Macromolecular Bioscience* Vol. 15, Issue 3, Pages 414-425 (https://doi.org/10.1002/mabi.201400334). In this aspect, the "longer" decenyl or "shorter" butenyl side chains are attached to a thiol amine by photoaddition in order to create charged oxazoline polymers with thioether primary or tertiary amines. The polymer sizes are about 20,000 Da to 30,000 Da in molecular size and the polydispersity indices (PDI) are about 1.4. These polymers were condensed with plasmid pEGFP-N1 (4.7 kb) to make polyplexes 90 to 200 nm size and zeta-potential values from −4 to +40 mV. However, the polyplexes had very low transfection properties (less than 25 percent). Moreover, these polymers were not safe and were found to hemolyze erythrocytes.

In addition to the safety concerns with the cationic polymers and polyplexes discussed above, there have been no attempts to prepare LNPs from these polymers or polyplexes. The present disclosure provides a solution to the shortcomings of the prior art.

SUMMARY OF THE INVENTION

The present disclosure relates to polyoxazoline (POZ) conjugates with pendent and terminal cationic groups (cationic POZ) suitable as a replacement for the ionizable lipids that are used in the commercially available mRNA vaccines. In particular, the inventors have now made the surprising observation that LNPs and/or polyplexes made with cationic POZ provide efficient and therapeutic delivery of RNA and DNA payloads.

In some embodiments, the cationic POZ is cationic poly(ethyloxazoline) (cationic PEOZ). In this aspect, LNPs may be made in accordance with the present disclosure including a sterol lipid, a helper lipid, a polymer lipid, and a cationic PEOZ (cationic PEOZ LNP). In some embodiments, the polymer lipid may be POZ-lipid. For example, a cationic PEOZ LNP may be made with cholesterol, DSPC, POZ-lipid, and cationic PEOZ. Similarly, polyplexes may be made with a cationic POZ and payload.

In this invention, co-polymers of poly(ethyl oxazoline) were made with monomers of pentynyl oxazoline (PtynOZ) and methyl oxazolinyl propionate (MeEstOZ) at smaller molecular weights of 1,000 to 3,000 Da and PDI of less than 1.2. These smaller polymers were used to prepare cationic POZ polymers with spermidine, spermine, choline, and N-methyl piperidine groups that in turn were used to prepare LNPs that deliver RNA and DNA payloads.

The present disclosure also relates to a lipid nanoparticle including:

a cationic POZ;

a helper lipid;

a polymer lipid; and a sterol lipid, wherein the cationic POZ is selected from the group consisting of one of the cationic POZ of Formulae I-IV:

$$R-POZ_1-\text{cation} \quad (I)$$

wherein R includes an initiating group and $POZ_1$ includes a polyoxazoline polymer;

$$R-\{[\underset{\text{cation}}{N}CH_2CH_2]_n[N(COR_2)CH_2CH_2]_m\}_a-T \quad (II)$$

wherein R includes an initiating group, n ranges from 1 to 10, $R_2$ is independently selected for each repeating unit from an unsubstituted or substituted alkyl, alkenyl, aralkyl, heterocyclylalkyl, or active functional group, m ranges from 1 to 100, a is ran, which indicates a random copolymer, or block, which indicates a block copolymer, and T includes a terminating group;

$$R-\{[\underset{\text{cation}}{N}CH_2CH_2]_n[N(COR_2)CH_2CH_2]_m\}_a-T\text{-cation} \quad (III)$$

wherein R includes an initiating group, n ranges from 1 to 10, $R_2$ is independently selected for each repeating unit from an unsubstituted or substituted alkyl, alkenyl, aralkyl, heterocyclylalkyl, or active functional group, m ranges from 1 to 100, a is ran, which indicates a random copolymer, or block, which indicates a block copolymer, and T includes a terminating group; and $$R-\{[\underset{\text{cation}}{N}CH_2CH_2]_n[N(COR_2)CH_2CH_2]_m\}_a-T\text{-cation} \quad (IV)$$

wherein R includes an initiating group, n ranges from 1 to 10, $R_2$ is independently selected for each repeating unit from an unsubstituted or substituted alkyl, alkenyl, aralkyl, heterocyclylalkyl, or active functional group, m ranges from 1 to 100, a ranges from 3 to 20, and T includes a terminating group.

In some embodiments, the lipid nanoparticle includes about 0.1 percent to about 10 percent cationic POZ, about 30 percent to about 80 percent sterol lipid, about 0.5 percent to about 20 percent polymer lipid, and about 15 percent to about 65 percent helper lipid. In other embodiments, the lipid nanoparticle includes about 30 percent to about 70 percent cationic POZ, about 30 percent to about 50 percent sterol lipid, about 0.5 percent to about 20 percent polymer lipid, and about 5 percent to about 15 percent helper lipid.

In still other embodiments, the polymer lipid is a POZ-lipid of Formula V:

$$R-POZ_2-L-\text{Lipid} \quad (V)$$

wherein R includes an initiating group, $POZ_2$ includes poly(oxazoline),

L includes a linking group, and

Lipid includes a non-charged lipid including at least one hydrophobic moiety.

In some aspects, the linking group is physiologically degradable. In other aspects, the linking group is stable.

The present disclosure also relates to a lipid nanoparticle including:

a cationic POZ of Formula I $$R-POZ_1-\text{cation} \quad (I)$$

wherein R includes an initiating group and $POZ_1$ includes a polyoxazoline polymer;

a helper lipid;

a polymer lipid; and a sterol lipid.

In some embodiments, the polymer lipid is a POZ-lipid of Formula V:

$$R-POZ_2-L-\text{Lipid} \quad (V)$$

wherein R includes an initiating group, $POZ_2$ includes poly(oxazoline),

L includes a linking group, and

Lipid includes a non-charged lipid including at least one hydrophobic moiety.

In some aspects, the linking group is physiologically degradable. In other aspects, the linking group is stable.

In other embodiments, the lipid nanoparticle includes about 0.1 percent to about 10 percent cationic POZ, about 30 percent to about 80 percent sterol lipid, about 0.5 percent to about 20 percent polymer lipid, and about 15 percent to about 65 percent helper lipid. In yet other embodiments, the lipid nanoparticle includes about 30 percent to about 70 percent cationic POZ, about 30 percent to about 50 percent sterol lipid, about 0.5 percent to about 20 percent polymer lipid, and about 5 percent to about 15 percent helper lipid.

The present disclosure also relates to a lipid nanoparticle including:

a cationic POZ of Formula II $$R-\{[\underset{\text{cation}}{N}CH_2CH_2]_n[N(COR_2)CH_2CH_2]_m\}_a-T \quad (II)$$

wherein R includes an initiating group, n ranges from 1 to 10, $R_2$ is independently selected for each repeating unit from an unsubstituted or substituted alkyl, alkenyl, aralkyl, heterocyclylalkyl, or active functional group, m ranges from 1 to 100, a is ran, which indicates a random copolymer, or block, which indicates a block copolymer, and T includes a terminating group;

a helper lipid;

a polymer lipid; and a sterol lipid.

In some embodiments, the polymer lipid is a POZ-lipid of Formula V:

$$R—POZ_2—L—Lipid \quad (V)$$

wherein R includes an initiating group, $POZ_2$ includes poly(oxazoline),

L includes a linking group, and

Lipid includes a non-charged lipid including at least one hydrophobic moiety.

In some aspects, the linking group is physiologically degradable. In other aspects, the linking group is stable.

In other embodiments, the lipid nanoparticle includes about 0.1 percent to about 10 percent cationic POZ, about 30 percent to about 80 percent sterol lipid, about 0.5 percent to about 20 percent polymer lipid, and about 15 percent to about 65 percent helper lipid. In still other embodiments, the lipid nanoparticle includes about 30 percent to about 70 percent cationic POZ, about 30 percent to about 50 percent sterol lipid, about 0.5 percent to about 20 percent polymer lipid, and about 5 percent to about 15 percent helper lipid.

The present disclosure also relates to a lipid nanoparticle including:

a cationic POZ of Formula III $$R—\{[\underset{\text{cation}}{\underset{|}{N}}CH_2CH_2]_n[N(COR_2)CH_2CH_2]_m\}_a—T\text{-cation} \quad (III)$$

wherein R includes an initiating group, n ranges from 1 to 10, $R_2$ is independently selected for each repeating unit from an unsubstituted or substituted alkyl, alkenyl, aralkyl, heterocyclylalkyl, or active functional group, m ranges from 1 to 100, a is ran, which indicates a random copolymer, or block, which indicates a block copolymer, and T includes a terminating group;

a helper lipid;

a polymer lipid; and a sterol lipid.

In some embodiments, the polymer lipid is a POZ-lipid of Formula V:

$$R—POZ_2—L—Lipid \quad (V)$$

wherein R includes an initiating group, $POZ_2$ includes poly(oxazoline),

L includes a linking group, and

Lipid includes a non-charged lipid including at least one hydrophobic moiety.

In some aspects, the linking group is physiologically degradable. In other aspects, the linking group is stable.

In other embodiments, the lipid nanoparticle includes about 0.1 percent to about 10 percent cationic POZ, about 30 percent to about 80 percent sterol lipid, about 0.5 percent to about 20 percent polymer lipid, and about 15 percent to about 65 percent helper lipid. In yet other embodiments, the lipid nanoparticle includes about 30 percent to about 70 percent cationic POZ, about 30 percent to about 50 percent sterol lipid, about 0.5 percent to about 20 percent polymer lipid, and about 5 percent to about 15 percent helper lipid.

The present disclosure also relates to a lipid nanoparticle including:

a cationic POZ of Formula IV $$R—\{[\underset{\text{cation}}{\underset{|}{N}}CH_2CH_2]_n[N(COR_2)CH_2CH_2]_m\}_a—T\text{-cation} \quad (IV)$$

wherein R includes an initiating group, n ranges from 1 to 10, $R_2$ is independently selected for each repeating unit from an unsubstituted or substituted alkyl, alkenyl, aralkyl, heterocyclylalkyl, or active functional group, m ranges from 1 to 100, a ranges from 3 to 20, and T includes a terminating group;

a helper lipid;

a polymer lipid; and a sterol lipid.

In some embodiments, the polymer lipid is a POZ-lipid of Formula IV:

$$R—POZ_2—L—Lipid \quad (IV)$$

wherein R includes an initiating group, $POZ_2$ includes poly(oxazoline),

L includes a linking group, and

Lipid includes a non-charged lipid including at least one hydrophobic moiety.

In some aspects, the linking group is physiologically degradable. In other aspects, the linking group is stable.

In other embodiments, R includes glycerol, pentaerythritol, polyglycerol, or combinations thereof. In still other embodiments, the lipid nanoparticle includes about 0.1 percent to about 10 percent cationic POZ, about 30 percent to about 80 percent sterol lipid, about 0.5 percent to about 20 percent polymer lipid, and about 15 percent to about 65 percent helper lipid. In yet other embodiments, the lipid nanoparticle includes about 30 percent to about 70 percent cationic POZ, about 30 percent to about 50 percent sterol lipid, about 0.5 percent to about 20 percent polymer lipid, and about 5 percent to about 15 percent helper lipid.

The present disclosure also relates to a compound of Formula I $$R—POZ_1—cation \quad (I)$$

wherein R includes an initiating group and $POZ_1$ includes a polyoxazoline polymer. In some embodiments, R includes hydrogen, a substituted or unsubstituted alkyl, an alkyne-substituted alkyl, or a substituted or unsubstituted aralkyl group.

The present disclosure also relates to a compound of Formula II

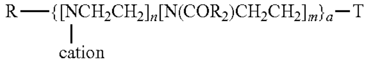

(II)

wherein R includes an initiating group, n ranges from 1 to 10, $R_2$ is independently selected for each repeating unit from an unsubstituted or substituted alkyl, alkenyl, aralkyl, heterocyclylalkyl, or active functional group, m ranges from 1 to 100, a is ran, which indicates a random copolymer, or block, which indicates a block copolymer, and T includes a terminating group. In some embodiments, R includes hydrogen, a substituted or unsubstituted alkyl, an alkyne-substituted alkyl, a triazole with attached carboxylic acid, or a substituted or unsubstituted aralkyl group.

The present disclosure also relates to a compound of Formula III

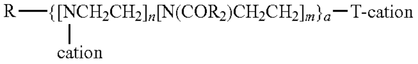

(III)

wherein R includes an initiating group, n ranges from 1 to 10, $R_2$ is independently selected for each repeating unit from an unsubstituted or substituted alkyl, alkenyl, aralkyl, heterocyclylalkyl, or active functional group, m ranges from 1 to 100, a is ran, which indicates a random copolymer, or block, which indicates a block copolymer, and T includes a terminating group. In some embodiments, R includes hydrogen, a substituted or unsubstituted alkyl, an alkyne-substituted alkyl, a triazole with attached carboxylic acid, or a substituted or unsubstituted aralkyl group.

The present disclosure also relates to a compound of Formula IV

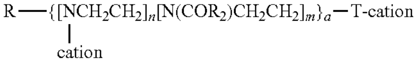

(IV)

wherein R includes an initiating group, n ranges from 1 to 10, $R_2$ is independently selected for each repeating unit from an unsubstituted or substituted alkyl, alkenyl, aralkyl, heterocyclylalkyl, or active functional group, m ranges from 1 to 100, a ranges from 3 to 20, and T includes a terminating group. In some embodiments, R includes glycerol, pentaerythritol, polyglycerol, or combinations thereof.

BRIEF DESCRIPTION OF THE DRAWINGS

Further features and advantages of the invention can be ascertained from the following detailed description that is provided in connection with the drawings described below.

DETAILED DESCRIPTION OF THE INVENTION

Figure 1:
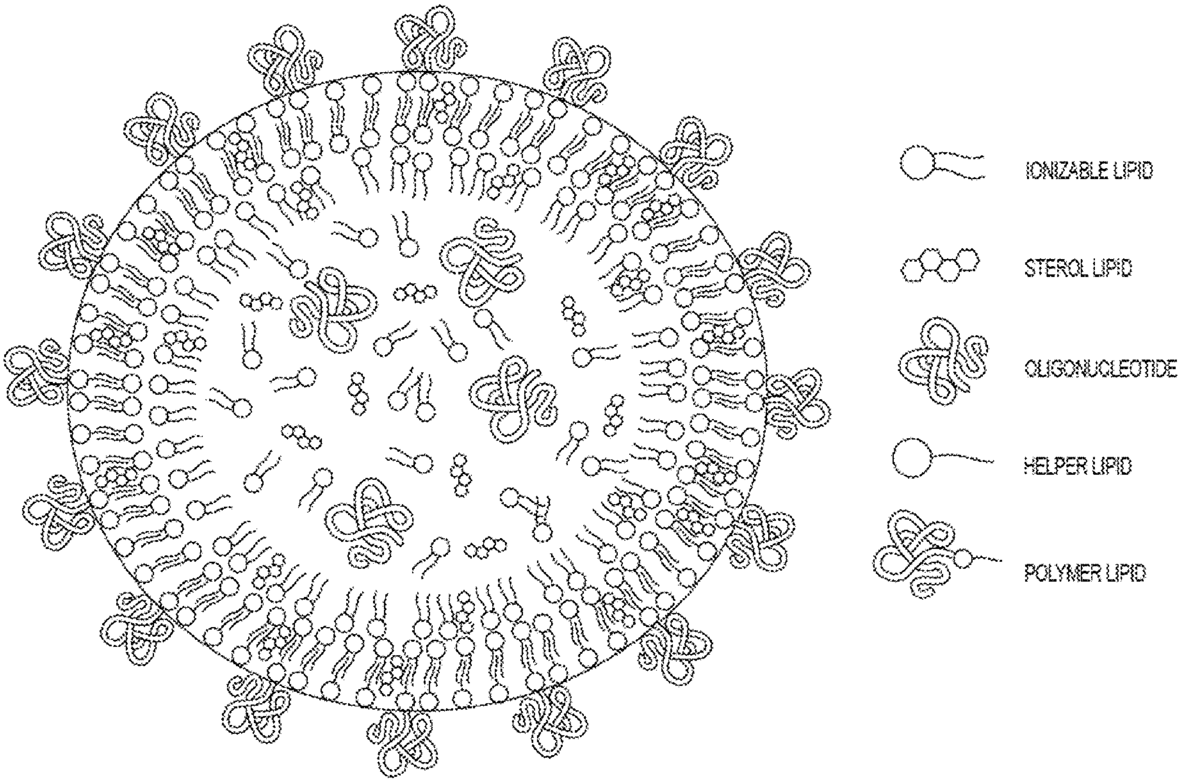
FIG. 1 PRIOR ART
FIG. 1 shows a conventional lipid nanoparticle.
Figure 2:
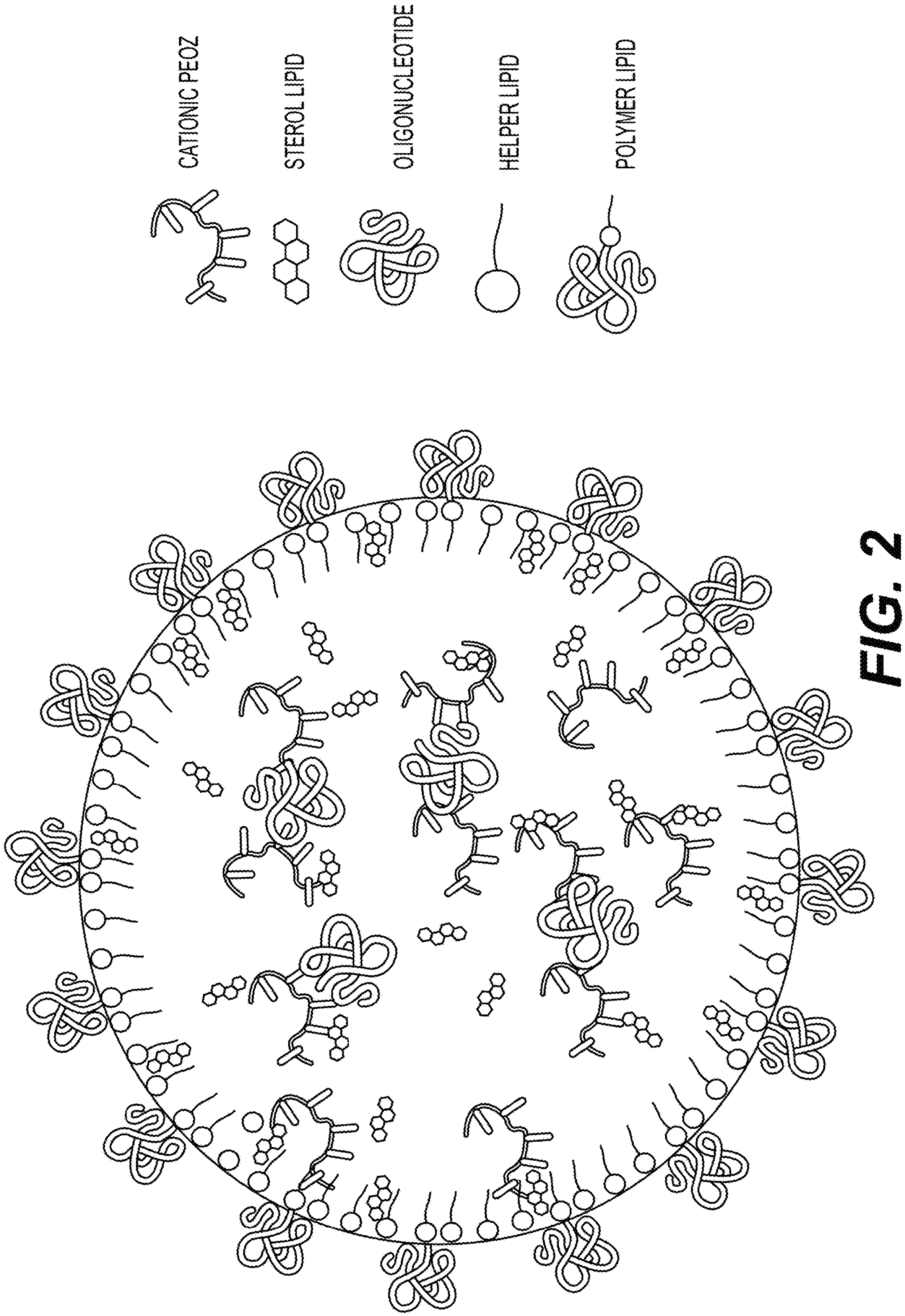
FIG. 2 shows a lipid nanoparticle in accordance with an embodiment of the present disclosure.

The present disclosure provides for cationic poly(oxazoline) (cationic POZ) suitable for replacement of the ionizable lipid in LNPs. In particular, a cationic POZ LNP may be made as shown in FIG. 2 and include a cationic POZ, a sterol lipid, a helper lipid, and a polymer lipid. The cationic POZ LNPs made in accordance with the present disclosure may be used to preferentially deliver an encapsulated payload, e.g., a nucleic acid payload including, but not limited to, mRNA or modified mRNA.

The cationic POZ and other components of the cationic POZ LNP are discussed in greater detail below.

Definitions

All patent applications, patents, and printed publications cited herein are incorporated herein by reference in the entireties, except for any definitions, subject matter disclaimers or disavowals, and except to the extent that the incorporated material is inconsistent with the express disclosure herein, in which case the language in this disclosure controls.

The articles "a" and "an" are used herein to refer to one or to more than one (i.e., to at least one) of the grammatical object of the article. By way of example, "an element" means one element or more than one element.

The terms "about" and "approximately" shall generally mean an acceptable degree of error or variation for the quantity measured given the nature or precision of the measurements. Numerical quantities given in this description are approximate unless stated otherwise, meaning that the term "about" or "approximately" can be inferred when not expressly stated.

As used herein, the term "active" or "activated" when used in conjunction with a particular functional group refers to a functional group that reacts readily with an electrophile or a nucleophile on another molecule. This is in contrast to those groups that require catalysts or impractical reaction conditions in order to react (i.e., a "non-reactive" or "inert" group).

As used herein, the term "physiologically degradable" or "physiologically releasable" refers to a linkage containing a cleavable moiety. The terms degradable and releasable do not imply any particular mechanism by which the linker is cleaved.

As used herein, the term "link", "linked" "linkage" or "linker" when used with respect to a POZ polymer, POZ conjugate, an agent, or compound described herein, or components thereof, refers to bonds that normally are formed as the result of a chemical reaction and typically are covalent linkages.

As used herein, the term "lipid nanoparticle" or "LNP" is used to encompass any of the many types of nanoparticles, including liposomes, that are formed by a lipid layer or layers surrounding a core containing a molecule to be released into the body. Liposomes generally have one or more contiguous lipid bilayers encapsulating an aqueous core. Other forms of liposome-like nanocarriers may have a lipid monolayer, or a non-contiguous bilayer, and may or may not have an aqueous core.

As used herein, the term "hydrophilic," for example with reference to a hydrophilic group, refers to a compound or molecule, or a portion thereof, where the interaction with water is thermodynamically more favorable than interaction with oil or other hydrophobic solvents. A hydrophilic compound is able to dissolve in, or be dispersed in, water.

As used herein, the term "hydrophobic", for example with reference to a hydrophobic portion, refers to a compound or molecule, or a portion thereof, where the interaction with water is thermodynamically less favorable than interaction with oil or other hydrophobic solvents. A hydrophobic compound is able to dissolve in, or be dispersed in, oil or other hydrophobic solvents.

As used herein, the term "inert" or "non-reactive" when used in conjunction with a particular functional group refers to a functional group that does not react readily with an electrophile or a nucleophile on another molecule and require catalysts or impractical reaction conditions in order to react.

As used herein, the term "pendent group" refers to a part of the POZ polymer that is attached to the POZ polymer.

As used herein, the term "pendent moiety" refers to a substituent that is linked to the POZ polymer portion via a linking group; a pendent moiety is exemplified by $R_2$ of formula IV as described herein.

As used herein, the term "pharmaceutically acceptable" refers to a compound that is compatible with the other ingredients of a composition and not deleterious to the subject receiving the compound or composition. In some embodiments, the term "pharmaceutically acceptable" means approved by a regulatory agency of the Federal or a state government or listed in the U.S. Pharmacopeia or other generally recognized pharmacopeia for use in animals, and more particularly in humans.

As used herein, the term "pharmaceutically acceptable form" is meant to include known forms of a compound or POZ conjugate that may be administered to a subject, including, but not limited to, solvates, hydrates, prodrugs, isomorphs, polymorphs, pseudomorphs, neutral forms and salt forms of a compound. In certain embodiments, the pharmaceutically acceptable form excludes prodrugs, isomorphs and/or pseudomorphs. In certain embodiments, the pharmaceutically acceptable form is limited to pharmaceutically acceptable salts, neutral forms, solvates and hydrates. In certain embodiments, the pharmaceutically acceptable form is limited to pharmaceutically acceptable salts and neutral forms. In certain embodiments, the pharmaceutically acceptable form is limited to pharmaceutically acceptable salts.

As used herein, the term "alkyl", whether used alone or as part of a substituent group, is a term of art and refers to saturated aliphatic groups that optionally contain one or more heteroatoms (such as O, S or N) which may be optionally substituted, including straight-chain alkyl groups, branched-chain alkyl groups, cycloalkyl groups, alkyl substituted cycloalkyl groups, and cycloalkyl substituted alkyl groups. In certain embodiments, a straight-chain or branched-chain alkyl has about 30 or fewer carbon atoms in its backbone (e.g., $C_1$-$C_{30}$ for straight chain, $C_3$-$C_{30}$ for branched chain), and alternatively, about 20 or fewer, or 10 or fewer. In certain embodiments, the term "alkyl" refers to a $C_1$-$C_{10}$ straight-chain alkyl group or a $C_1$-$C_3$ straight-chain alkyl group. In certain embodiments, the term "alkyl" refers to a $C_3$-$C_{12}$ branched-chain alkyl group. In certain embodiments, the term "alkyl" refers to a $C_3$-$C_8$ branched-chain alkyl group. Representative examples of alkyl include, but are not limited to, methyl, ethyl, n-propyl, iso-propyl, n-butyl, sec-butyl, iso-butyl, tert-butyl, n-pentyl, isopentyl, neopentyl, and n-hexyl. In certain embodiments, the term "alkyl" refers to a $C_1$-$C_{10}$ straight-chain alkyl group that contains one or more heteroatoms in place of a carbon atom (such as O, S or N), wherein the heteroatom may be optionally substituted. In certain embodiments, the term "alkyl" refers to a $C_1$-$C_{10}$ straight-chain alkyl group that is substituted with up to 5 groups selected from the group consisting of OH, $NH_2$ and =0.

As used herein, the term "alkenyl", whether used alone or as part of a substituent group, is a term of art and refers to unsaturated aliphatic groups that optionally contain one or more heteroatoms (such as O, S or N) which may be optionally substituted, including, a straight or branched chain hydrocarbon radical containing from 2 to 30 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl. The unsaturated bond(s) of the alkenyl group can be located anywhere in the moiety and can have either the (Z) or the (E) configuration about the double bond(s).

As used herein, the term "alkynyl", whether used alone or as part of a substituent group, is a term of art and refers to unsaturated aliphatic groups that optionally contain one or more heteroatoms (such as O, S or N) which may be optionally substituted, including, straight or branched chain hydrocarbon radical containing from 2 to 30 carbon atoms and containing at least one carbon-carbon triple bond. Representative examples of alkynyl include, but are not limited, to acetylenyl, 1-propynyl, 2-propynyl, 3-butynyl, 2-pentynyl, 4-pentynyl, and 1-butynyl.

As used herein, the term "substituted alkyl", "substituted alkenyl", and "substituted alkynyl" refers to alkyl, alkenyl and alkynyl groups as defined above in which one or more bonds to a carbon(s) or hydrogen(s) are replaced by a bond to non-hydrogen or non-carbon atoms such as, but not limited to, a halogen atom in halides such as F, Cl, Br, and I; and oxygen atom in groups such as carbonyl, carboxyl, hydroxyl groups, alkoxy groups, aryloxy groups, heterocyclyloxy groups, and ester groups; a sulfur atom in groups such as thiol groups, alkyl and aryl sulfide groups, sulfone groups, sulfonyl groups, and sulfoxide groups; a nitrogen atom in groups such as amines, amides, alkylamines, dialkylamines, arylamines, alkylarylamines, diarylamines, N-oxides, imides, enamines imines, oximes, hydrazones, heterocyclylamine, (alkyl)(heterocyclyl)-amine, (aryl)(heterocyclyl)amine, diheterocyclylamine, triazoles, and nitriles; a silicon atom in groups such as in trialkylsilyl groups, dialkylarylsilyl groups, alkyldiarylsilyl groups, and triarylsilyl groups; and other heteroatoms in various other groups. In a specific embodiment, a "polar alkyl", "polar alkenyl", and "polar alkynyl", refers to alkyl, alkenyl, and alkynyl groups substituted with an atom that results in a polar covalent bond. In another specific embodiment, a "polar alkyl", "polar alkenyl", and "polar alkynyl" refers to C1 to C5 alkyl, alkenyl, and alkynyl, groups substituted with an atom that results in a polar covalent bond. In a specific embodiment, a "polar alkyl", "polar alkenyl", and "polar alkynyl", refers to alkyl, alkenyl, alkynyl groups, such as C1 to C5 alkyl, alkenyl, and alkynyl groups, substituted with an —OH group and/or a —C(O)—OH group.

As used herein, the term "halo" or "halogen" whether used alone or as part of a substituent group, is a term of art and refers to —F, —Cl, —Br, or —I.

As used herein, the term "alkoxy", whether used alone or as part of a substituent group, is a term of art and refers to an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

As used herein, the term "aralkyl" or "arylalkyl", whether used alone or as part of a substituent group, is a term of art and refers to an alkyl group substituted with an aryl group, wherein the moiety is appended to the parent molecule through the alkyl group. An arylalkyl group may be optionally substituted. A "substituted aralkyl" has the same meaning with respect to unsubstituted aralkyl groups that substituted aryl groups had with respect to unsubstituted aryl groups. However, a substituted aralkyl group also includes groups in which a carbon or hydrogen bond of the alkyl part of the group is replaced by a bond to a non-carbon or a non-hydrogen atom.

As used herein, the term "heteroaralkyl" or "heteroarylalkyl", whether used alone or as part of a substituent group, is a term of art and refers to an alkyl group substituted with a heteroaryl group, wherein the moiety is appended to the parent molecular moiety through the alkyl group. A heteroarylalkyl may be optionally substituted. The term "substituted heteroarylalkyl" has the same meaning with respect to unsubstituted heteroarylalkyl groups that substituted aryl groups had with respect to unsubstituted aryl groups.

As used herein, the term "heterocyclylalkyl", whether used alone or as part of a substituent group, is a term of art and refers to unsubstituted or substituted alkyl, alkenyl or alkynyl groups in which a hydrogen or carbon bond of the unsubstituted or substituted alkyl, alkenyl or alkynyl group is replaced with a bond to a heterocyclyl group. A heterocyclylalkyl may be optionally substituted. The term "substituted heterocyclylalkyl" has the same meaning with respect to unsubstituted heterocyclylalkyl groups that substituted aryl groups had with respect to unsubstituted aryl groups. However, a substituted heterocyclylalkyl group also includes groups in which a non-hydrogen atom is bonded to a heteroatom in the heterocyclyl group of the heterocyclylalkyl group such as, but not limited to, a nitrogen atom in the piperidine ring of a piperidinylalkyl group.

As used herein, the term "aryl", whether used alone or as part of a substituent group, is a term of art and refers to includes monocyclic, bicyclic and polycyclic aromatic hydrocarbon groups, for example, benzene, naphthalene, anthracene, and pyrene. The aromatic ring may be substituted at one or more ring positions with one or more substituents, such as halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, fluoroalkyl (such as trifluromethyl), cyano, or the like. The term "aryl" also includes polycyclic ring systems having two or more cyclic rings in which two or more carbons are common to two adjoining rings (the rings are "fused rings") wherein at least one of the rings is an aromatic hydrocarbon, e.g., the other cyclic rings may be cycloalkyls, cycloalkenyls, cycloalkynyls, aryls, heteroaryls, and/or heterocyclyls. In certain embodiments, the term "aryl" refers to a phenyl group. The aryl group may be optionally substituted.

As used herein, the term "cycloalkyl", whether used alone or as part of a substituent group, is a term of art and refers to a saturated carbocyclic group containing from three to six ring carbon atoms, wherein such ring may optionally be substituted with a substituted or unsubstituted alkyl group or a substituent as described for a substituted alkyl group. Exemplary cycloalkyl groups include, but are not limited to, cyclopropyl, cyclobutyl, cyclopentyl, cyclohexyl, 2-methylcyclobutyl and 4-ethylcyclohexyl.

As used herein, the term "heteroaryl", whether used alone or as part of a substituent group, is a term of art and refers to a monocyclic, bicyclic, and polycyclic aromatic group having 3 to 30 total atoms including one or more heteroatoms such as nitrogen, oxygen, or sulfur in the ring structure. Exemplary heteroaryl groups include azaindolyl, benzo(b)thienyl, benzimidazolyl, benzofuranyl, benzoxazolyl, benzothiazolyl, benzothiadiazolyl, benzotriazolyl, benzoxadiazolyl, furanyl, imidazolyl, imidazopyridinyl, indolyl, indolinyl, indazolyl, isoindolinyl, isoxazolyl, isothiazolyl, isoquinolinyl, oxadiazolyl, oxazolyl, purinyl, pyranyl, pyrazinyl, pyrazolyl, pyridinyl, pyrimidinyl, pyrrolyl, pyrrolo[2,3-d]pyrimidinyl, pyrazolo[3,4-d]pyrimidinyl, quinolinyl, quinazolinyl, triazolyl, thiazolyl, thiophenyl, tetrahydroindolyl, tetrazolyl, thiadiazolyl, thienyl, thiomorpholinyl, triazolyl or tropanyl, and the like. The "heteroaryl" may be substituted at one or more ring positions with one or more substituents such as halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, fluoroalkyl (such as trifluromethyl), cyano, or the like. The term "heteroaryl" also includes polycyclic ring systems having two or more cyclic rings in which two or more carbons are common to two adjoining rings (the rings are "fused rings") wherein at least one of the rings is an aromatic group having one or more heteroatoms in the ring structure, e.g., the other cyclic rings may be cycloalkyls, cycloalkenyls, cycloalkynyls, aryls, heteroaryls, and/or heterocyclyls.

As used herein, the term "heterocyclyl", whether used alone or as part of a substituent group, is a term of art and refers to a radical of a non-aromatic ring system, including, but not limited to, monocyclic, bicyclic, and tricyclic rings, which can be completely saturated or which can contain one or more units of unsaturation, for the avoidance of doubt, the degree of unsaturation does not result in an aromatic ring system, and having 3 to 15 atoms including at least one heteroatom, such as nitrogen, oxygen, or sulfur. For purposes of exemplification, which should not be construed as limiting the scope of this invention, the following are examples of heterocyclic rings: aziridinyl, azirinyl, oxiranyl, thiiranyl, thiirenyl, dioxiranyl, diazirinyl, diazepanyl, 1,3-dioxanyl, 1,3-dioxolanyl, 1,3-dithiolanyl, 1,3-dithianyl, imidazolidinyl, isothiazolinyl, isothiazolidinyl, isoxazolinyl, isoxazolidinyl, azetyl, oxetanyl, oxetyl, thietanyl, thietyl, diazetidinyl, dioxetanyl, dioxetenyl, dithietanyl, dithietyl, dioxalanyl, oxazolyl, thiazolyl, triazinyl, isothiazolyl, isoxazolyl, azepines, azetidinyl, morpholinyl, oxadiazolinyl, oxadiazolidinyl, oxazolinyl, oxazolidinyl, oxopiperidinyl, oxopyrrolidinyl, piperazinyl, piperidinyl, pyranyl, pyrazolinyl, pyrazolidinyl, pyrrolinyl, pyrrolidinyl, quinuclidinyl, thiomorpholinyl, tetrahydropyranyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. A heterocyclyl group may be substituted at one or more ring positions with one or more substituents such as halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, fluoroalkyl (such as trifluromethyl), cyano, or the like.

As used herein, the terms "treatment", "treat", and "treating" refers a course of action (such as administering a conjugate as described herein or pharmaceutical composition comprising a conjugate as described herein) so as to prevent, eliminate, or reduce a symptom, aspect, or characteristics of a disease or condition. Such treating need not be absolute to be useful. In one embodiment, treatment includes a course of action that is initiated concurrently with or after the onset of a symptom, aspect, or characteristics of a disease or condition. In another embodiment, treatment includes a course of action that is initiated before the onset of a symptom, aspect, or characteristics of a disease or condition.

As used herein, the term "in need of treatment" refers to a judgment made by a caregiver that a patient requires or will benefit from treatment. This judgment is made based on a variety of factors that are in the realm of a caregiver's expertise, but that includes the knowledge that the patient is ill, or will be ill, as the result of a disease or condition that is treatable by a method or compound of the disclosure.

As used herein, the terms "individual", "subject", or "patient" refers to any animal, including mammals, such as mice, rats, other rodents, rabbits, dogs, cats, swine, cattle, sheep, horses, or primates, and humans. The terms may specify male or female or both, or exclude male or female. In a preferred embodiment, the terms "individual", "subject", or "patient" refers to a human.

As used herein, the term "therapeutically effective amount" refers to an amount of a conjugate, either alone or as a part of a pharmaceutical composition, that is capable of having any detectable, positive effect on any symptom, aspect, or characteristics of a disease or condition. Such effect need not be absolute to be beneficial.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, fragmentation, decomposition, cyclization, elimination, or other reaction.

It will be understood that when a group is specified as a part of a compound, the substitution of the group may be adjusted to accommodate the particular bonds. For example, when an alkyl group is joined to two other groups, the alkyl group is considered an alkylene group.

The term "substituted" is also contemplated to include all permissible substituents of organic compounds. In a broad aspect, the permissible substituents include acyclic and cyclic, branched and unbranched substituents, carbocyclic and heterocyclyl, aromatic and nonaromatic substituents of organic compounds. Illustrative substituents include, for example, those described herein above. For purposes of this disclosure, the heteroatoms, such as oxygen or nitrogen, may have hydrogen substituents and/or any permissible substituents of organic compounds described herein which satisfy the valences of the heteroatoms. Exemplary substitutions include, but are not limited to, hydroxy, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, fluoroalkyl (such as trifluromethyl), cyano, or the like. This invention is not intended to be limited in any manner by the permissible substituents of organic compounds.

Other chemistry terms herein are used according to conventional usage in the art, as exemplified by The McGraw-Hill Dictionary of Chemical Terms (ed. Parker, S., 1985), McGraw-Hill, San Francisco, incorporated herein by reference). Unless otherwise defined, all technical and scientific terms used herein have the same meaning as commonly understood by one of ordinary skill in the art to which this invention pertains.

The term "pharmaceutically acceptable salt" as used herein includes salts derived from inorganic or organic acids including, for example, hydrochloric, hydrobromic, sulfuric, nitric, perchloric, phosphoric, formic, acetic, lactic, maleic, fumaric, succinic, tartaric, glycolic, salicylic, citric, methanesulfonic, benzenesulfonic, benzoic, malonic, trifluoroacetic, trichloroacetic, naphthalene-2-sulfonic, and other acids. Pharmaceutically acceptable salt forms can include forms wherein the ratio of molecules comprising the salt is not 1:1. For example, the salt may comprise more than one inorganic or organic acid molecule per molecule of base, such as two hydrochloric acid molecules per molecule of conjugate. As another example, the salt may comprise less than one inorganic or organic acid molecule per molecule of base, such as two molecules of conjugate per inorganic or organic acid molecule.

The terms "carrier" and "pharmaceutically acceptable carrier" as used herein refer to a diluent, adjuvant, excipient, or vehicle with which a compound is administered or formulated for administration. Non-limiting examples of such pharmaceutically acceptable carriers include liquids, such as water, saline, and oils; and solids, such as gum acacia, gelatin, starch paste, talc, keratin, colloidal silica, urea, and the like. In addition, auxiliary, stabilizing, thickening, iso osmotic, cryo-preservatives, lubricating, flavoring, and coloring agents may be used. Other examples of suitable pharmaceutical carriers are described in *Remington's Science and Practice of Pharmacy* ($23^{rd}$ edition, ISBN 9780128200070) and *Handbook of Pharmaceutical Excipients* ($8^{th}$ edition, 978-0-85-711271-2), each herein incorporated by reference in their entirety.

As used herein, the term "target molecule" refers to any molecule having a therapeutic or diagnostic application or a targeting function, or a vehicle with which a compound is administered or formulated for administration, wherein the target molecule is capable of forming a linkage with an active functional group on a POZ polymer or a POZ derivative of the present disclosure, including, but not limited to, a therapeutic agent (such as but not limited to a drug), a diagnostic agent, a targeting agent, an organic small molecule, an oligonucleotide, a polypeptide, an antibody, an antibody fragment, a protein, a carbohydrate such as heparin or hyaluronic acid, or a lipid such as a glycerolipid, glycolipid, or phospholipid.

As used herein, "lipid" or "lipid portion" means (i) an organic compound that includes an ester of fatty acid or a derivative thereof and is characterized by being insoluble in water, but soluble in many organic solvents, and includes, but is not limited to, simple lipids such as fats, oils, and waxes, compound lipids such as phospholipids, glycolipids, cationic lipids, non-cationic lipids, neutral lipids, and anionic lipids, and derived lipids such as steroids, as well as (ii) an organic compound that does not include an ester of fatty acid, but mimics such an organic compound through its amphipathic character, i.e., it possesses both hydrophobic and hydrophilic portions, and, thus, is able to aggregate in a specific manner to form layers, vesicles and LNPs in aqueous environments.

As used herein, "small interfering RNA (siRNA)" means a class of double-stranded RNA molecules, 16-40 nucleotides in length, that are involved in the RNA interference (RNAi) pathway, where it interferes with the expression of a specific gene. In addition to their role in the RNAi pathway, siRNAs also act in RNAi-related pathways.

As used herein, "sgRNA" means a class of guide RNA molecules that are involved in CRISPR-Cas9 genome editing, where the sgRNA provides a template for precise genome editing to minimize "off-target" editing and maximize "on-target" editing.

As used herein, "saRNA" means a class of RNA molecules that are "self-amplifying" or "self-replicating" due to the nature of the encoded protein, typically a replicase, that result in multiple copies of the RNA.

As used herein, "RNA" means a molecule comprising at least one ribonucleotide residue, including siRNA, antisense RNA, single stranded RNA, microRNA, mRNA, noncoding RNA, self-amplifying RNA, sgRNA, gRNA and multivalent RNA. "Ribonucleotide" means a nucleotide with a hydroxyl group at the 2' position of a β-D-ribo-furanose moiety, and includes but is not limited to, modified ribonucleotides The terms include double-stranded RNA, single-stranded RNA, isolated RNA such as partially purified RNA, essentially pure RNA, synthetic RNA, recombinantly produced RNA, as well as altered RNA that differs from naturally occurring RNA by the addition, deletion, substitution, and/or alteration of one or more nucleotides.

Cationic POZ

Without being bound by any particular theory, it is believed that cationic POZ is a suitable replacement for ionizable lipid in a stable LNP. As such, without being bound by any particular theory, efficient and therapeutic delivery of RNA and DNA payloads is possible with LNPs made with cationic POZ (and without the conventionally employed ionizable lipid).

For example, it has now been discovered that cationic poly(ethyloxazoline) (cationic PEOZ) makes a stable LNP that demonstrates the characteristic dependence on flow-rate ratios when incorporating an oligonucleotide for therapeutic delivery. In this aspect, LNPs prepared with microfluidic techniques produce large particles at very low flow rates, and a limit-size LNP that is independent of flow rate at slightly higher flow rates. This high efficiency manufacture of LNPs without any ionizable lipid components is not only surprising and unexpected, but also may have profound implications on a range of RNA and DNA therapeutics including vaccines, cancer immunotherapy and gene therapy. Indeed, the cationic POZ LNPs of the present disclosure may have no immunogenicity, or reduced immunogenicity, as compared to corresponding LNPs containing ionizable lipids and PEG-lipids and, as such, may provide a safer method of delivering the payload.

In some embodiments, the cationic POZ may be a POZ-cation of Formula I:

$$R-POZ-cation \tag{I}$$

where R includes an initiating group. In some aspects, R includes a hydrogen, a substituted or unsubstituted alkyl, an alkyne-substituted alkyl, or a substituted or unsubstituted aralkyl group. The POZ may be a polyoxazoline polymer. In some aspects, POZ may be poly(ethyloxazoline). In other aspects, POZ may be a polyoxazoline polymer of the structure $[N(COR_2)CH_2CH_2]_n$ where $R_2$ is ethyl and n ranges from 1 to 1000. The POZ-cation may be any of the cationic POZ synthesized in the examples. For example, in some embodiments, the cationic POZ is PEOZ cholamide.

In other embodiments, the cationic POZ may be a POZ-cation of Formula II:

$$R-\{[NCH_2CH_2]_n[N(COR_2)CH_2CH_2]_m\}_a-T \tag{II}$$
$$\text{cation (attached to N of }[NCH_2CH_2]_n)$$

where R includes an initiating group, n ranges from 1 to 10, $R_2$ is independently selected for each repeating unit from an unsubstituted or substituted alkyl, alkenyl, aralkyl, heterocyclylalkyl, or active functional group, m ranges from 1 to 100, a is ran, which indicates a random copolymer, or block, which indicates a block copolymer, and T includes a terminating group. In some aspects, R includes a hydrogen, a substituted or unsubstituted alkyl, an alkyne-substituted alkyl, a triazole with attached carboxylic acid, or a substituted or unsubstituted aralkyl group.

T may be any nucleophilic group that is capable of terminating the POZ polymer living cationic polymerization. In one embodiment, T is a thioalkyl carboxylic acid, a thiocarboxylic ester, or a hydroxyl. In other embodiments, T includes Z—B-Q, and wherein Z includes S, O, or N, B is an optional linking group, and Q is a terminating nucleophile or a terminating portion of a nucleophile. In some aspects, Z is S. In other aspects, Z is O. In still other aspects, Z is N.

In certain aspects, Q is inert (i.e., does not contain a functional group). In other aspects, Q contains a functional group. When Q contains a functional group, suitable functional groups include, but are not limited to, alkyne, alkene, amine, oxyamine, aldehyde, ketone, acetal, thiol, ketal, maleimide, ester, carboxylic acid, activated carboxylic acid (such as, but not limited to, N-hydroxysuccinimidyl (NHS) and 1-benzotriazine active ester), an active carbonate, a chloroformate, alcohol, azide, vinyl sulfone, or orthopyridyl disulfide (OPSS). Furthermore, when Q contains a functional group, the functional group may be chemically orthogonal to one or more or all other functional groups present on the conjugate. When Q is a non-reactive group, any non-reactive group may be used, including, but not limited to unsubstituted alkyl and $—C_6H_6$.

B may include, but is not limited to, an alkylene group. In one embodiment, B is $—(CH_2)_y—$ where y is an integer selected from 1 to 16. In some aspects, y may an integer selected from 1 to 10, 1 to 8, 1 to 6, or 1 to 4. For example, in one embodiment, y is 2.

In other embodiments, the cationic POZ may be a POZ-cation of Formula III:

$$R—\{[\underset{\text{cation}}{\underset{|}{N}}CH_2CH_2]_n[N(COR_2)CH_2CH_2]_m\}_a—T\text{-cation} \quad \text{(III)}$$

Where R includes an initiating group, n ranges from 1 to 10, $R_2$ is independently selected for each repeating unit from an unsubstituted or substituted alkyl, alkenyl, aralkyl, heterocyclylalkyl, or active functional group, m ranges from 1 to 100, a is ran, which indicates a random copolymer, or block, which indicates a block copolymer, and T includes a terminating group. In some aspects, R includes a hydrogen, a substituted or unsubstituted alkyl, an alkyne-substituted alkyl, a triazole with attached carboxylic acid, or a substituted or unsubstituted aralkyl group. T may be any of the terminating groups discussed above with respect to Formula II.

In other embodiments, the cationic POZ may be a POZ-cation of Formula IV:

$$R\text{-}\{[\underset{\text{cation}}{\underset{|}{N}}CH_2CH_2]_n[N(COR_2)CH_2CH_2]_m\}_a\text{-}T \quad \text{(IV)}$$

where R includes a branching group, n ranges from 1 to 10, $R_2$ is independently selected for each repeating unit from an unsubstituted or substituted alkyl, alkenyl, aralkyl, heterocyclylalkyl, or active functional group, m ranges from 1 to 100, a ranges from 3 to 20, and T includes a terminating group. In some aspects, R includes glycerol, pentaerythritol, polyglycerol, etc. T may be any of the terminating groups discussed above with respect to Formula II.

A nonlimiting example of such a structure IV with a glycerol central branch point is as follows:

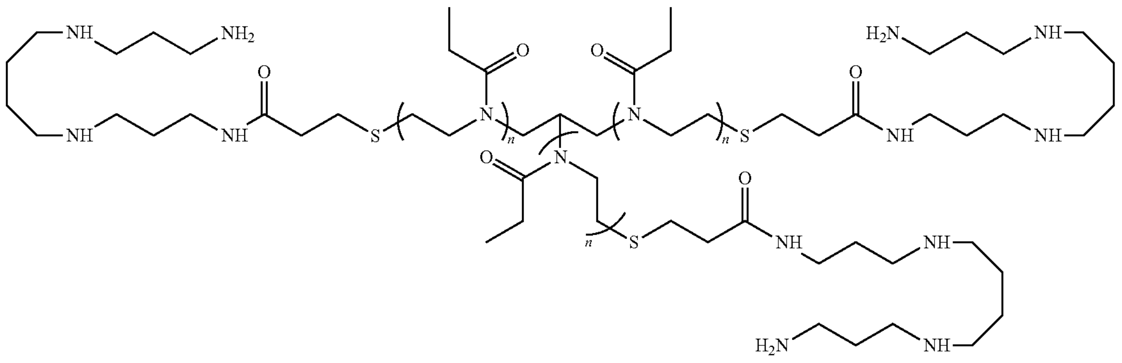

This glycerol-derived cationic POZ can be synthesized by the following route:

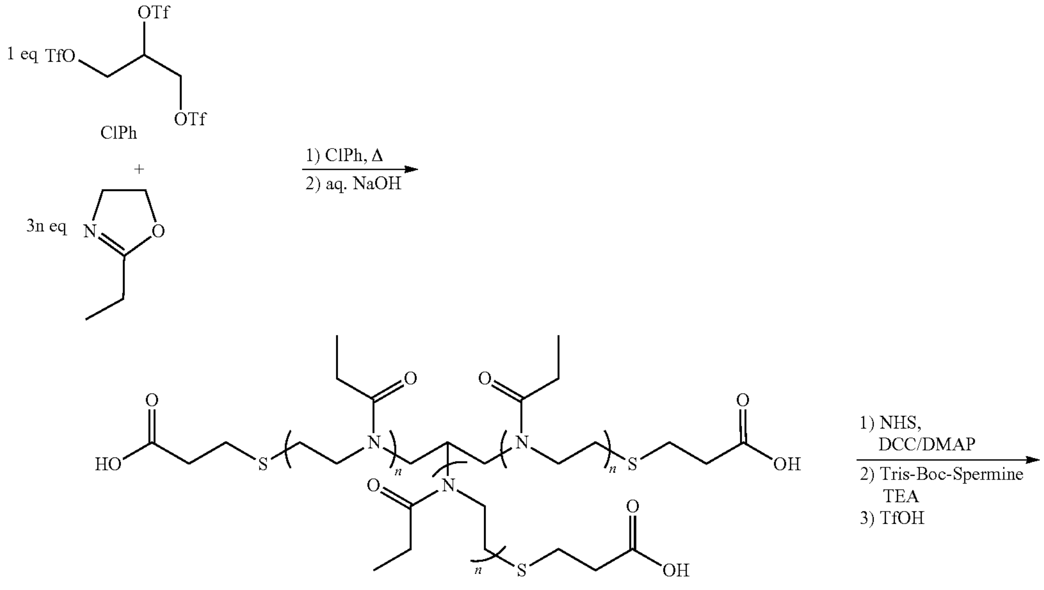

-continued

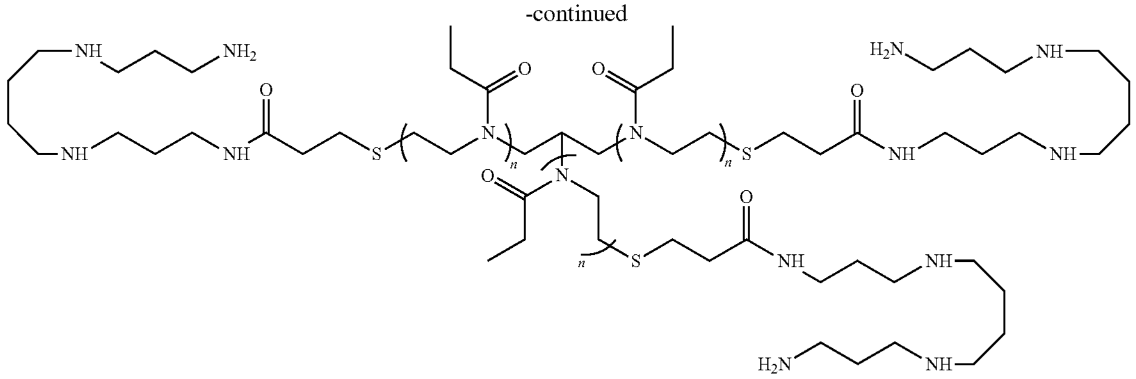

Sterol Lipid

As briefly discussed above, cationic POZ LNPs made in accordance with the present disclosure include a sterol lipid for stability. A suitable sterol lipid for use in accordance with the present disclosure is cholesterol. Another suitable sterol lipid for use in accordance with the present disclosure is phytosterol.

Helper Lipid

Cationic POZ LNPs made in accordance with the present disclosure include a helper lipid to provide structural support and facilitate endocytosis. Helper lipids refer to amphipathic lipids that have hydrophobic and polar head group moieties, and which can form spontaneously into bilayer vesicles in water, as exemplified by phospholipids, or are stably incorporated into lipid bilayers, with the hydrophobic moiety in contact with the interior, hydrophobic region of the bilayer membrane, and the polar head group moiety oriented toward the exterior, polar surface of the membrane. Such helper lipids typically include one or two hydrophobic acyl hydrocarbon chains or a steroid group and may contain a chemically reactive group, such as an amine, acid, ester, aldehyde or alcohol, at the polar head group. Non-limiting examples suitable for use in accordance with the present disclosure include phospholipids, such as phosphatidyl choline (PC), phosphatidyl ethanolamine (PE), phosphatidic acid (PA), phosphatidyl inositol (PI), and sphingomyelin (SM), where the two hydrocarbon chains are typically between about 14-22 carbon atoms in length and have varying degrees of unsaturation. Other suitable helper lipids include, but are limited to, glycolipids, such as cerebrosides and gangliosides. In one aspect, the helper lipid is at least one of 1,2-dioleoyl-sn-glycero-3-phosphoethanolamine (DOPE), 1,2-distearoyl-sn-glycero-3-phosphocholine (DSPC), and POPE (1-palmitoyl-2-oleoylsn-glycero-3-phosphoethanolamine).

Polymer Lipid

In some embodiments, the polymer lipid may be a POZ-lipid of Formula V:

$$R_1\text{—POZ—L—Lipid} \tag{V}$$

wherein $R_1$ includes an initiating group, POZ comprises poly(ethyloxazoline), L includes a physiologically degradable linking group, and Lipid includes a non-charged lipid including at least one hydrophobic moiety. In other embodiments, POZ includes $[N(COR_2)CH_2CH_2]_n$, where $R_2$ is ethyl. In still other embodiments, $R_1$ includes a hydrogen, a substituted or unsubstituted alkyl, an alkyne-substituted alkyl, a triazole with attached carboxylic acid, or a substituted or unsubstituted aralkyl group. In yet other embodiments, L includes ethers, esters, carboxylate esters, carbonate esters, carbamates, amines, amides, urethanes, disulfides, and combinations thereof. In still other embodiments, Lipid includes two hydrophobic moieties. In other embodiments, Lipid includes phospholipid, a glycerolipid, a di-alkyl acetamide, or a combination thereof. In yet other embodiments, Lipid includes 1,2-dimyristoyl-sn-glycerol, 1,2-dilauroyl-sn-glycerol, or a combination thereof.

In other embodiments, the polymer lipid may be a POZ-lipid of Formula VI:

$$\text{Lipid—}L_1\text{—}(\text{POZ})_n^a\text{—T} \tag{VI}$$

wherein Lipid includes a non-charged lipid including at least one hydrophobic moiety, $L_1$ includes a physiologically degradable linking group, POZ includes a polyoxazoline polymer of the structure $[N(COR_2)CH_2CH_2]$, wherein $R_2$ is ethyl, n ranges from 1 to 1,000, a is ran, which indicates a random copolymer, or block, which indicates a block copolymer, and T includes a terminating group.

In some embodiments, $L_1$ includes ethers, esters, carboxylate esters, carbonate esters, carbamates, amines, amides, urethanes, disulfides, and combinations thereof. In other embodiments, $L_1$ includes a triazole.

In yet other embodiments, T includes Z—B-Q, and wherein Z includes S, O, or N, B is an optional linking group, and Q is a terminating nucleophile or portion thereof. In still other embodiments, Lipid includes two hydrophobic moieties. In other embodiments, Lipid includes a phospholipid, a glycerolipid, a di-alkyl acetamide, or a combination thereof. In still other embodiments, Lipid includes 1,2-dimyristoyl-sn-glycerol, 1,2-dilauroyl-sn-glycerol, or a combination thereof.

In still other embodiments, the polymer lipid may be a POZ-lipid of Formula VII:

$$R_1\text{—}(\text{POZ})_n^a\text{—Z—}L_2\text{—Lipid} \tag{VII}$$

wherein $R_1$ includes an initiating group; POZ comprises a polyoxazoline polymer of the structure $[N(COR_2)CH_2CH_2]$, wherein $R_2$ is ethyl; n ranges from 1 to 1,000; a is ran, which indicates a random copolymer, or block, which indicates a block copolymer; Z comprises S, O, or N; $L_2$ includes a physiologically degradable linking group, and Lipid includes a non-charged lipid comprising at least one hydrophobic group.

In some embodiments, $L_2$ includes ethers, esters, carboxylate esters, carbonate esters, carbamates, amines, amides, urethanes, disulfides, and combinations thereof. In other embodiments, Lipid includes two hydrophobic moieties. In still other embodiments, Lipid includes a phospholipid, a glycerolipid, a di-alkyl acetamide, or a combination thereof. In yet other embodiments, Lipid includes 1,2-dimyristoyl-sn-glycerol, 1,2-dilauroyl-sn-glycerol, or a combination thereof. In still other embodiments, $R_1$ includes a hydrogen, or a substituted or unsubstituted alkyl, and n ranges from 15 to 35.

In yet other embodiments, the polymer lipid may be a POZ-lipid of Formula VIII:

$$R-\{[\underset{\substack{|\\ L_3\\ |\\ A}}{N}CH_2CH_2]_n[N(COR_2)CH_2CH_2]_m\}_a-T \qquad \text{(VIII)}$$

wherein $R_1$ includes an initiating group, $L_3$ includes a physiologically degradable linking group, Lipid includes a non-charged lipid comprising at least one hydrophobic moiety, n ranges from 1 to 5, $R_2$ is independently selected for each repeating unit from an unsubstituted or substituted alkyl, alkenyl, aralkyl, heterocyclylalkyl, or active functional group, m ranges from 1 to 100, a is ran, which indicates a random copolymer, or block, which indicates a block copolymer, and T includes a terminating group.

In some embodiments, $L_3$ includes esters, carboxylate esters, carbonate esters, carbamates, amides, and combinations thereof. In other embodiments, $L_3$ includes a triazole. In still other embodiments, T includes Z—B-Q, and wherein Z includes S, O, or N, B is an optional linking group, and Q is a terminating nucleophile or portion thereof. In yet other embodiments, Lipid includes two hydrophobic moieties. In still other embodiments, Lipid includes a phospholipid, a glycerolipid, a di-alkyl acetamide, or a combination thereof. In yet other embodiments, Lipid includes 1,2-dimyristoyl-sn-glycerol, 1,2-dilauroyl-sn-glycerol, or a combination thereof.

More specific embodiments and examples of suitable POZ lipids for use as the polymer lipid in a cationic POZ LNP made in accordance with the present disclosure are provided in U.S. Provisional Patent Application No. 63/440,210, the entire disclosure of which is incorporated by reference herein.

Payload

As briefly discussed above, cationic POZ LNPs formed in accordance with the present disclosure may also include a payload. In this aspect, the payload may be an oligonucleotide, protein, or a combination thereof.

In one embodiment, the oligonucleotide comprises DNA, siRNA, self-replicating mRNA (saRNA), mRNA comprised of modified nucleosides, and mRNA comprised of naturally occurring nucleosides. In one aspect, the oligonucleotide is DNA. In another aspect, the oligonucleotide is siRNA. In still another aspect, the oligonucleotide is saRNA, mRNA comprised of modified nucleosides, or mRNA comprised of naturally occurring nucleosides. In still another aspect, the oligonucleotide is a sgRNA used in genome editing.

The oligonucleotide can be encapsulated into the LNP with high efficiency. In one embodiment, the oligonucleotide is encapsulated into the LNP with an efficiency of at least 90 percent. In another embodiment, the oligonucleotide is encapsulated into the LNP with an efficiency of about 90 to about 99 percent. In still another embodiment, the oligonucleotide is encapsulated into the LNP with an efficiency of about 90 to about 95 percent. In yet another embodiment, the oligonucleotide is encapsulated into the LNP with an efficiency of greater than about 95 percent.

Similarly, polyplexes may be made with the oligonucleotide and POZ polymer with high efficiency. In some embodiments, the oligonucleotide is incorporated into a polyplex with an efficiency of at least 90 percent, about 90 to about 99 percent, about 90 to about 95 percent, or greater than about 95 percent.

Properties of Cationic POZ LNP

The particle size of cationic POZ LNPs made in accordance with the present disclosure can vary. In one embodiment, cationic POZ LNPs formed in accordance with the present disclosure are amphiphilic spherical vesicles formed by one or more lipid bilayers enveloping an aqueous core with size ranging from about 10 nm to about 10 microns. In another embodiment, a cationic POZ LNP formed in accordance with the present disclosure has a particle size of about 25 nm to about 8 microns. In yet another embodiment, a cationic POZ LNP formed in accordance with the present disclosure has a particle size of about 30 nm to about 5 microns. In this aspect, the particle size of the cationic POZ LNP may be between about 20 nm to about 3 microns. In another embodiment, the cationic POZ LNP may be between about 10 nm and about 1000 nm, between about 25 nm and about 500 nm, between about 35 nm and about 250 nm, between about 40 nm and about 150 nm, or between about 45 nm and about 100 nm. Methods of size fractionation are disclosed herein. However, in certain aspects, size fractionation is not required.

Methods of Preparing the Cationic POZ LNP and Polyplexes

The cationic POZ LNP composition of the present disclosure may be prepared by a variety of methods. In one embodiment, the liposomes are prepared by the reverse-phase evaporation method (Szoka et al. PNAS 1978 vol. 75, 4194-4198; Smirnov et al., Byulleten' Éksperimental'noi Biologii i Meditsiny, 1984, Vol. 98, pp. 249-252; U.S. Pat. No. 4,235,871). In this method, an organic solution of liposome-forming lipids, which may include the polymer lipid, either with or without a linked target molecule, is mixed with a smaller volume of an aqueous medium, and the mixture is dispersed to form a water-in-oil emulsion, preferably using pyrogen-free components. The target molecule to be delivered is added either to the lipid solution, in the case of a lipophilic target molecule, or to the aqueous medium, in the case of a water-soluble target molecule. The lipid solvent is removed by evaporation and the resulting gel is converted to liposomes. The reverse phase evaporation vesicles (REVs) have typical average sizes between about 0.2-0.4 microns and are predominantly oligolamellar, that is, contain one or a few lipid bilayer shells. The REVs may be readily sized, as discussed below, by extrusion to give oligolamellar vesicles having a selected size preferably between about 0.05 to 0.2 microns.

In addition, multilamellar vesicles (MLVs) can be created. In this method, a mixture of liposome-forming lipids, which may include the polymer lipid, either with or without a linked target molecule, as described herein are dissolved in a suitable solvent is evaporated in a vessel to form a thin film. The thin film is then covered by an aqueous medium.

The lipid film hydrates to form MLVs. MLVs generally exhibit sizes between about 0.1 to 10 microns. MLVs may be sized down to a desired size range by extrusion and other method described herein.

One effective sizing method for REVs and MLVs involves extruding an aqueous suspension of the liposomes through a polycarbonate membrane having a selected uniform pore size, typically 0.05, 0.08, 0.1, 0.2, or 0.4 microns (Szoka et al. PNAS 1978 vol. 75, 4194-4198). The pore size of the membrane corresponds roughly to the largest sizes of liposomes produced by extrusion through that membrane, particularly where the preparation is extruded two or more times through the same membrane. Process for sizing MLVs of larger sizes is provided by Zhu et al. (PLoS One. 2009; 4 (4):e5009. Epub 2009 Apr. 6).

When small particle sizes are desired, the REV or MLV preparations can be treated to produce small unilamellar vesicles (SUVs) that are characterized by sizes in the 0.04-0.08 micron range. Such particles may be useful in targeting tumor tissue or lung tissue where the particles may be absorbed through capillary walls (particles larger than 0.1 microns may not be absorbed).

The cationic POZ LNP may be treated to remove extraneous components prior to use. For example, if surfactants are used as discussed above, the excess surfactants may be removed prior to use. In addition, where a payload, such as an oligonucleotide discussed above, is entrapped in the cationic POZ LNP composition, excess or non-entrapped payload may be removed prior to use. Separation techniques to accomplish this task are known in the art and the particular method selected may depend on the nature of the component to be removed. Suitable methods include, but are not limited to, centrifugation, dialysis and molecular-sieve chromatography. The composition can be sterilized by filtration through a conventional 0.22 micron filter.

Cationic POZ LNPs can be prepared by the traditional method that involves the hydration of a lipid film containing polymer lipid, cationic POZ, helper lipids, and cholesterol. This process involves the dissolution of these materials in organic solvent such as chloroform or dichloromethane and then evaporating the solvent to produce a thin film. The film is then hydrated with an aqueous buffer containing the drug or nucleic acid to passively encapsulate the payload. LNPs of heterogeneous particles with a low encapsulation are normally formed, which requires size reduction by extrusion or sonication.

Another suitable technique uses rapid mixing with a microfluidizer. Lipid stock solutions are prepared by dissolving the lipids in an organic solvent, such as ethanol. Aqueous stock solutions contain the nucleic acid dissolved in a buffer solution of known pH, ionic strength and buffer capacity. The two stock solutions are passed through a micromixer at a predetermined rate to allow for the cationic lipid to interact with the negatively charged nucleic acid, resulting in higher encapsulation efficiencies (i.e., >90 percent) and homogeneous size distribution. The aqueous-to-organic solvent ratios during the mixing process is important. The organic solvent is removed by dialysis, tangential flow filtration or centrifugation or other technique. LNPs of defined sizes are produced by controlling the microfluidic operating parameters, resulting in LNPs of low polydispersity and uniform particle size. The average particle diameter (<100 nm), polydispersity (<0.40 and, more particularly, <0.20), and zeta potential of the LNPs are three methods used to characterize the preparation.

The ratio of cationic POZ lipid to polymer lipid to cholesterol can be varied in order to allow for optimal size, high payload release and transfection, and improved stability of the hydrated formulation. In one embodiment, the mol percent of cationic POZ in the LNP is about 30 percent to about 70 percent. In some aspects, the mol percent of cationic POZ in the LNP is about 40 percent to about 60 percent. In other aspects, the mol percent of cationic POZ in the LNP is about 45 percent to about 55 percent. In this regard, the remainder of the LNP may be about 30 to about 50 percent sterol lipid, about 0.5 percent to about 20 percent polymer lipid, and about 5 percent to about 15 percent helper lipid. In some embodiments, the mol percent of sterol lipid in the LNP may range from about 35 percent to about 45 percent. In other embodiments, the mol percent of polymer lipid may range from about 0.5 percent to about 10 percent, about 0.5 percent to about 5 percent, or about 1 percent to about 3 percent. In still other embodiments, the mol percent of the helper lipid may range from about 7 percent to about 12 percent, about 8 percent to about 11 percent, or about 6 percent to about 14 percent.

In still other embodiments, the LNP may be about 0.1 percent to about 10 percent cationic POZ, about 30 percent to about 80 percent sterol lipid, about 0.5 percent to about 20 percent polymer lipid, and about 15 percent to about 65 percent helper lipid. In some aspects, the mol percent of cationic POZ in the LNP is about 0.2 percent to about 8 percent. In other aspects, the mol percent of cationic POZ in the LNP is about 0.3 percent to about 5 percent. In still other aspects, the mol percent of sterol lipid in the LNP may range from about 35 percent to about 78 percent, about 30 percent to about 40 percent, about 70 percent to about 80 percent, or about 55 percent to about 65 percent. In yet other aspects, the mol percent of polymer lipid may range from about 0.5 to about 10 percent, about 0.5 to about 5 percent, or about 1 to about 3 percent. In still other embodiments, the mol percent of the helper lipid may range from about 18 percent to about 63 percent, about 17 percent to about 25 percent, about 30 percent to about 40 percent, or about 55 percent to about 65 percent.

Similarly, polyplexes may be made in accordance with the present disclosure using the cationic polymers and payloads disclosed herein. In some embodiments, a solution of the cationic polymer may be mixed with a payload solution.

Administration

The cationic POZ LNPs of the present disclosure may be delivered to any cell. After in vivo administration of the cationic POZ LNPs, the payload is released. In this aspect, the cationic POZ LNPs of the present disclosure may be included a pharmaceutical composition capable of eliciting a treatment for a disorder or disease. For example, pharmaceutical compositions including cationic POZ LNPs made in accordance with the present disclosure may be used to prevent or treat infectious diseases including, but not limited to, SARS-CoV-2, rabies, influenza, and others by specifically targeting certain immune cells other than the antigen-presenting cells. In addition, pharmaceutical compositions including cationic POZ LNPs made in accordance with the present disclosure may be used as therapeutics for cancer and genetic diseases. Such pharmaceutical compositions may also include a pharmaceutically acceptable carrier in addition to the cationic POZ LNPs.

In one embodiment, a pharmaceutical composition including an effective amount of cationic POZ LNP of the present disclosure can be delivered to an animal. In this aspect, delivery of an effective amount of a cationic POZ LNP of the present disclosure may occur via subcutaneous, intravenous, intramuscular, intradermal or aerosol routes. In one embodiment, the animal is a human.

EXAMPLES

The following examples do not limit the invention or the claimed subject-matter. Rather, these examples are intended to further illustrate embodiments of the present disclosure.

Example 1. Synthesis of H-PEOZ-NHS Ester 2K

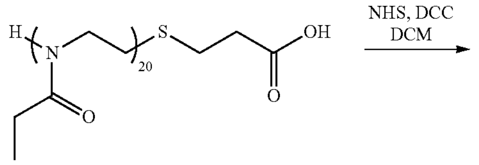

PEOZ-Acid 2K

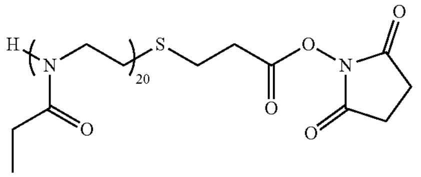

PEOZ-NHS Ester 2K

To a 250-mL round bottomed flask was charged with PEOZ Acid 2K (5.00 g, MW 2271.9 Da, 2.201 mmol, 1.00 equiv.) followed by acetonitrile (50 mL). The solution was evaporated to dryness by rotary evaporation. The residual white solid was dissolved in DCM (50 mL). N-hydroxysuccinimide (284.3 mg, 2.421 mmol, 1.10 eq.) was then added into the clear solution under an atmosphere of Argon. DCC (490.8 mg, 2.355 mmol, 1.07 eq.) was added in one portion, and the resulting solution was allowed to stir for overnight at room temperature. The cloudy reaction mixture was filtered through a sintered glass frit. The resulting filtrate was concentrated to dryness by rotary evaporation. The remaining solid was re-dissolved into DCM (27 mL), then slowly transferred into a beaker containing a stirred solution of MTBE (500 mL). The precipitate was collected via filtration at reduced pressure, the solid was then transferred into a 100 mL round bottomed flask, and dissolved in methanol (15 mL). The solution was evaporated to dryness by rotary evaporation, and the remaining solids were dried under vacuum, which afforded 4.2 g of white solid.

$^1$HNMR analysis showed the standard signals for PEOZ-NHS ester 2K (500 MHz, DMSO-d6): δ 3.32 ($CH_2CH_2$ backbone); 2.34 ($C(O)—CH_2$); 0.97 ($CH_3$). Additional signal was present for the terminal NHS ester at δ 2.81 ($COCH_2CH_2CO$).

Example 2. Synthesis of $(EOZ)_{12}(PrAcidOZ)_8$-OH 2K, POZ-OH 2K 8p Acids

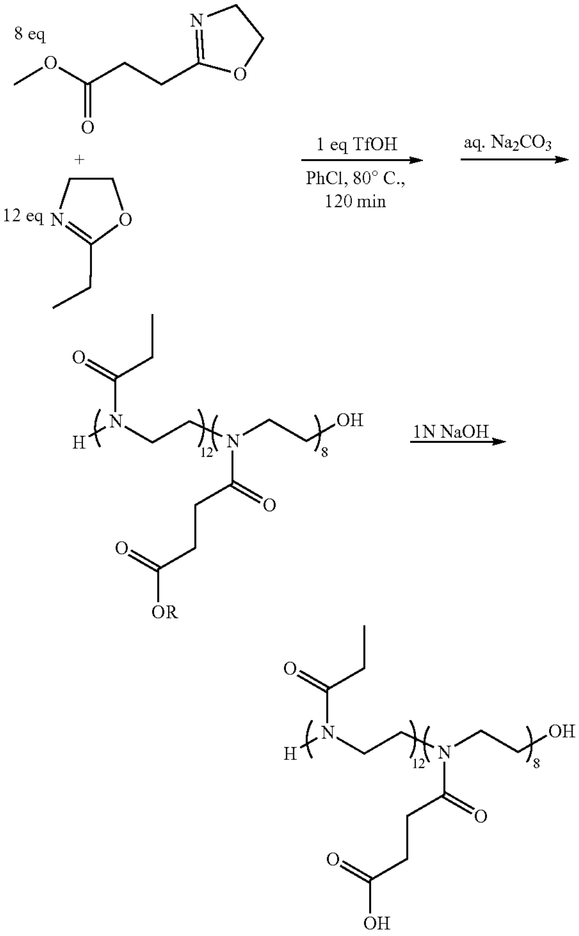

R = —Me or —H

An oven-dried 50 mL round bottomed flask, equipped with a reflux condenser and an argon gas inlet, was charged with MeEstOZ* (2.12 g, 13.5 mmol, 8 equiv) and 2-ethyl-2-oxazoline (2.00 g, 20.2 mmol, 12 equiv) followed by a stir bar and PhCl (17 mL) under an atmosphere of argon. TfOH (148.8 μL, 1.68 mmol, 1.00 equiv) was added dropwise, and the mixture was allowed to stir at room temperature for 5 minutes. The reaction was then warmed to 80° C. and stirred for 120 minutes. The polymerization mixture was then cooled to room temperature and an aqueous solution of $Na_2CO_3$ (0.712 g, 6.72 mmol, 4.00 equiv) in $H_2O$ (17 mL) was added. The reaction mixture was allowed to stir for at least 12 hours. Following this time, PhCl was removed using a rotary evaporator. To the resulting aqueous solution was added 1N NaOH(aq) (6 mL) followed by stirring overnight. The mixture was acidified using 3N HCl(aq) and charged with NaCl (6.5 g, 15 w/v %). DCM (25 mL) was added into the aqueous mixture while stirring and a white sticky chunk of precipitate was formed. All the solution was decanted and the residue was washed by swirling and decanting using DCM (25 mL). The residue was dried under reduced pressure to give 2.6 g (65% yield) of the desired product as a white powder.

$^1$H NMR (Varian, 500 MHz, 10 mg/mL DMSO-$d_6$, δ) analysis showed the standard backbone signals for PEOZ at 7.82 (terminal NH), 3.34 ($CH_2CH_2$ backbone), 3.16 (N—$CH_2$), 2.32-2.27 (C(O)—$CH_2$—), 0.94 (—$CH_3$). Signals for the pendant group were present at 2.51-2.40 ppm (—$CH_2CH_2CO_2H$ pendent). The number of pendant groups was previously calculated from the polymer starting material to be 7.19. MALDI analysis showed Mn 2520 Da and PDI 1.105.

*MeEstOZ has been synthesized under the modified literature procedure: Bouten, P. J. M.; Hertsen, D.; Vergaelen, M.; Monnery, B. D.; Boerman, M. A.; Goossens, H.; Catak, S.; van Hest, J. C. M.; van Speybroeck, V.; Hoogenboom, R. *Polym. Chem.* 2015, 6, 514-518.

Example 3. Synthesis of $(EOZ)_5(PrAcidOZ)_4$-Pip-COOH 1.3K

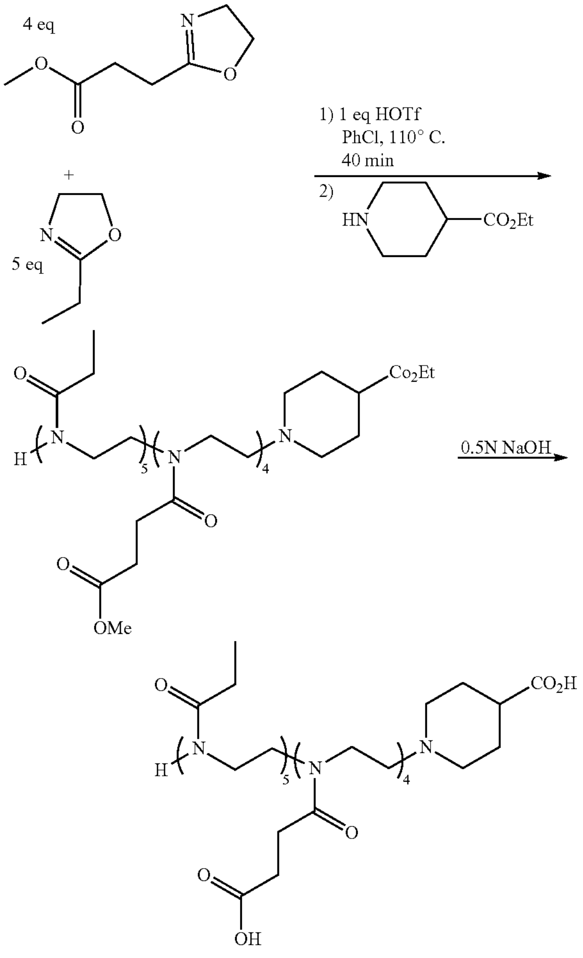

PEOZ-PipEtEster 1.2K 4P MeEster. An oven-dried 50 mL round bottomed flask, equipped with a reflux condenser and an argon gas inlet, was charged with MeEstOZ (1.466 g, 11.5 mmol, 4 equiv) and 2-ethyl-2-oxazoline (1.429 g, 14.4 mmol, 5 equiv) followed by a stir bar and PhCl (13 mL) under an atmosphere of argon. TfOH (255.1 μL, 2.88 mmol, 1.00 equiv) was added dropwise, and the mixture was allowed to stir at room temperature for 5 minutes. The reaction was then heated to 110° C. and stirred for 40 minutes. The polymerization mixture was then cooled to room temperature and ethyl isonipecotate (0.91 mL, 5.77 mmol, 2.00 equiv) was added. The reaction mixture was allowed to stir for at least 12 hours at room temperature. Following this time period, all the volatiles were removed using a rotary evaporator followed by azeotrope using 0.5N HCl(aq) solution (15 mL). The resulting aqueous solution was passed through the amberlite column (IR120H/IRA67) and the collected filtrate was freeze dried using a lyophilizer to give 3.61 g (97.7% yield) of the desired product as a white crystalline.

$^1$H NMR (Varian, 500 MHz, 10 mg/mL DMSO-$d_6$, δ) analysis showed the standard backbone signals for PEOZ at 7.82 (terminal NH), 4.08 (m, C(═O)$OCH_2CH_3$ of terminal piperidine, 2H), 3.64 (m, CH of piperidine, 1H), 3.36 ($CH_2CH_2$ backbone), 3.15 (N—$CH_2$), 2.58 (m, —$NCH_2$— of terminal piperidine, 4H), 2.31 (C(O)—$CH_2$—), 1.84 (m, —$NCH_2CH_2$ of terminal piperidine, 4H), 1.19 (m, —$OCH_2CH_3$ of terminal piperidine), 0.95 (—$CH_3$). Signals for the pendant group were present at 2.96 and 2.58 ppm (—$CH_2CH_2CO_2CH_3$ of pendent). 3.55 ppm (s, —$OCH_3$ of pendent). The ratio of EOZ:MeEstOZ:terminal ester was determined as 5:4.4:0.9. MALDI analysis showed Mn 1239 Da and PDI 1.08.

PEOZ-Pip-acid 1.2K 4P acid. PEOZ-PipEtEster 1.2K 4P MeEster, collected above, was dissolved in 1.0N NaOH(aq) (28.8 mL) to give a solution with pH of 13. The reaction mixture was stirred at room temperature for 18 hours, whereupon the mixture was acidified to pH=3. The resulting solution was washed with DCM (20 mL). The aqueous layer was collected and concentrated using a rotary evaporator to give a thick slush. The residue was dissolved in DMF (14 mL), filtered using a syringe filter, and concentrated using a rotary evaporator. The resulting sticky gel was swirled in THF, sonicated, and decanted. This process was repeated with diethyl ether. The residue was dried in a full vacuum to give 3.47 g of the target product as a white crystalline.

$^1$H NMR (Varian, 500 MHz, 10 mg/mL DMSO-$d_6$, δ) analysis showed the standard backbone signals for PEOZ at 7.82 (terminal NH), 3.36 ($CH_2CH_2$ backbone), 3.15 (N—$CH_2$), 2.05 (m, —$NCH_2$— of terminal piperidine, 4H), 2.28 (C(O)—$CH_2$—), 1.75 (m, —$NCH_2CH_2$ of terminal piperidine), 0.96 (—$CH_3$). Signals for the pendant group were present at 2.53 and 2.41 ppm (—$CH_2CH_2CO_2H$ of pendent). The completion of the hydrolysis was confirmed by the disappearance of peaks for the ester groups at 3.55 ppm (—$OCH_3$) 4.08 (m, C(═O)$OCH_2CH_3$), and 1.19 (m, —$OCH_2CH_3$).

Example 4. Synthesis of PEOZ-Propargylamide 2K

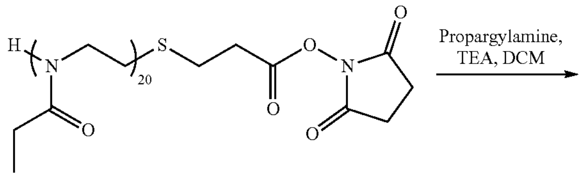

PEOZ-NHS Ester 2K

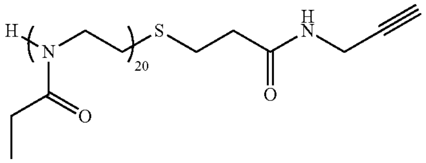

PEOZ-Propargylamide 2K

PEOZ-NHS ester 2K (4.00 g, MW 2369, 1.69 mmol, 1.00 equiv.) was dissolved in DCM (40 mL) in a 100-mL round bottomed flask equipped with a stir bar and under an atmosphere of Argon. The clear solution was then charged with propargylamine (0.22 mL, 3.38 mmol, 2.00 equiv) followed by addition of triethylamine (0.47 mL, 3.38 equiv, 2.00 equiv), and the reaction mixture was allowed to stir for 12 hours at room temperature. The reaction mixture was filtered through a coarse sintered glass frit. The resulting filtrate was concentrated to dryness by rotary evaporation. The remaining solid was re-dissolved into DCM (21 mL), then slowly transferred into a beaker containing a stirred solution of MTBE (150 mL). The precipitate was collected via filtration at reduced pressure, and the remaining solids were dried under vacuum, which afforded 3.9 g of white solid.

$^1$HNMR analysis showed the standard signals for PEOZ-Propargylamide 2K (500 MHz, DMSO-d6): δ 3.32 ($CH_2CH_2$ backbone); 2.34 (C(O)—$CH_2$); 0.97 ($CH_3$). Additional signals were present for the terminal propargylamide at δ 3.85 (N—$CH_2$) and 3.75 (C≡CH).

Example 5. Synthesis of $P[(EOZ)_m(PtynOZ)_n]$-Propargylamide 2K

Step One. Synthesis of NHS Ester

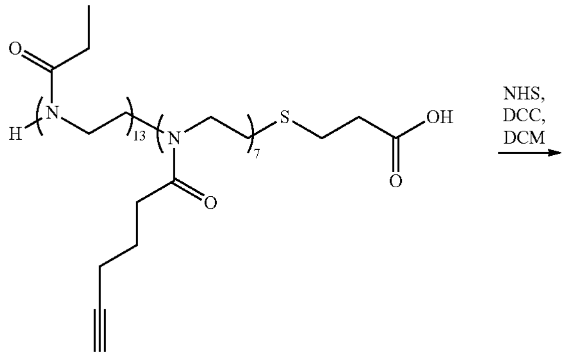

$P[(EOZ)_{13}(PtynOZ)_7]$-Acid

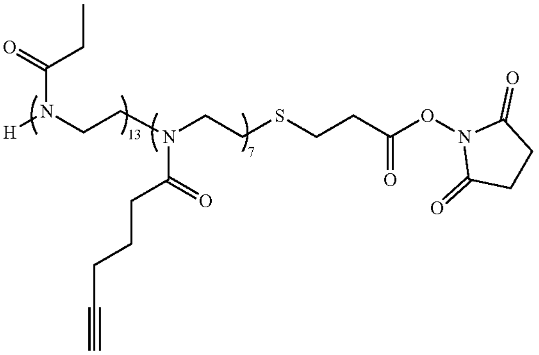

$P[(EOZ)_{13}(PtynOZ)_7]$-NHS Ester

To a 250-mL round bottomed flask with a stir bar was charged with $P[(EOZ)_{13}(PtynOZ)_7]$-Acid 2K (MW 2356 Da, 10.0 g, 4.24 mmol, 1.00 equiv.) followed by DCM (100 mL). N-hydroxysuccinimide (0.82 grams, 4.67 mmol, 1.10 equiv) was then added into the clear solution under an atmosphere of Argon. DCC (0.55 g, 4.54 mmol, 1.07 equiv) was added in one portion, and the resulting solution was allowed to stir for overnight at room temperature. The reaction mixture was filtered through a sintered glass frit. The resulting filtrate was concentrated to dryness by rotary evaporation. The remaining solid was re-dissolved into DCM (55 mL), then slowly transferred into a beaker containing a stirred solution of MTBE (400 mL). The precipitate was collected via filtration at reduced pressure, and the remaining solids were dried under vacuum, which afforded 10.4 g of white solid.

$^1$HNMR analysis showed the standard signals for $P[(EOZ)_{13}(PtynOZ)_7]$-NHS ester 2K (500 MHz, DMSO-d6): δ 3.32 ($CH_2CH_2$ backbone); 2.34 (C(O)—$CH_2$); 1.66 (pendent alkyne-$CH_2$—); 0.97 ($CH_3$). Additional signal was present for the terminal NHS ester at δ 2.81 ($COCH_2CH_2CO$).

Step Two. Synthesis of $P[(EOZ)_{13}(PtynOZ)_7]$-Propargylamide 2K

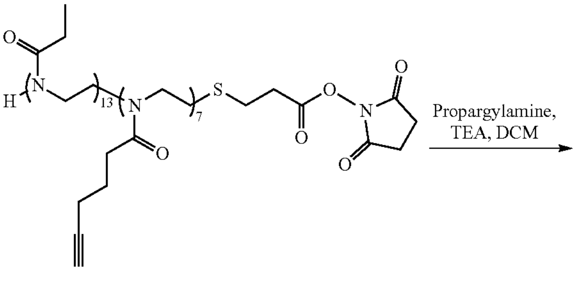

$P[(EOZ)_{13}(PtynOZ)_7]$-NHS Ester

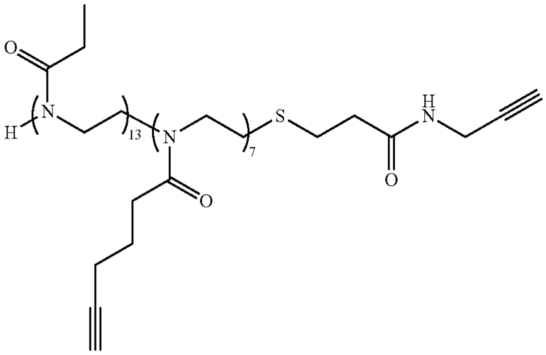

$P[(EOZ)_{13}(PtynOZ)_7]$-Propargylamide 2K $P[(EOZ)_{13}(PtynOZ)_7]$-NHS ester 2K (10.4 g, 4.24 mmol, 1.00 equiv.) was dissolved into DCM (100 mL) in a 250-mL round bottomed flask equipped with a stir bar under an atmosphere of Argon. The clear solution was then charged with propargylamine (0.54 mL, 8.49 mmol, 2.00 equiv) followed by addition of triethylamine (1.18 mL, 8.49 equiv, 2.00 equiv), and the reaction mixture was allowed to stir for 12 hours at room temperature. The reaction mixture was filtered through a coarse sintered glass frit. The resulting filtrate was concentrated to dryness by rotary evaporation. The remaining solid was re-dissolved into DCM (55 mL), then slowly transferred into a beaker containing a stirred solution of MTBE (400 mL). The precipitate was collected via filtration at reduced pressure, and the remaining solids were dried under vacuum, which afforded 9.5 g of white solid.

$^1$HNMR analysis showed the standard signals for P[(EOZ)$_m$(PtynOZ)$_n$]-Propargylamide 2K (500 MHz, DMSO-d6): δ 3.32 ($CH_2CH_2$ backbone); 2.34 (C(O)—$CH_2$); 1.66 (alkyne-$CH_2CH_2$); 0.97 ($CH_3$). Additional signals were present for the terminal propargylamide at δ 3.85 (N—$CH_2$) and 3.75 (C≡CH).

Example 6. Synthesis of PEOZ-N,N-dimethylaminoethylamide 1K (PEOZ DMAEA 1K)

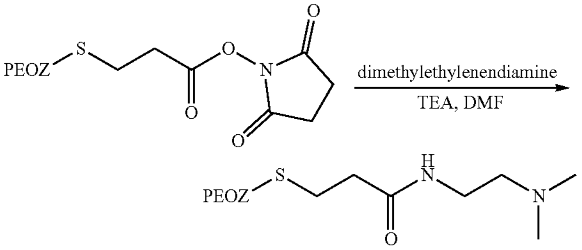

PEOZ-NHS Ester 1K (1.130 g, 1.004 mmol, 1.0 equiv.) in a 50 mL RB flask was dissolved in anhydrous DCM (20 mL). Under Ar, N,N-Dimethylethylenediamine (121.5 μL, 1.090 mmol, 1.05 equiv.) was added the clear solution. The clear solution was allowed to stir at room temperature overnight. The solution was evaporated to dryness. The residual solid was dissolved in water (50 mL). The cloudy solution was filtered. The filtrate was loaded to a Amberlite IRA-67 column (5 gm), followed by elution with water (75 mL). The eluent was collected. The solution pH was adjusted by 1 N NaOH to 12.40. NaCl (18.8 g) was dissolved to the solution. The solution was extracted by DCM (3×75 mL). The DCM phase was dried over anhydrous magnesium sulfate (1.6 g) and anhydrous sodium sulfate (84 g) for one hour. The mixture was filtered, and filtrate was evaporated to dryness. Continue to dry the residual in vacuum overnight, which afforded 945 mg of white solid. The solid was dissolved in water (13.5 mL). The solution pH was adjusted from 9.80 to 6.75 by 1 N HCl. The solution was then lyophilized, which afforded 0.94 g of white solid.

$^1$HNMR analysis showed the standard signals for PEOZ DMAEA 1K (500 MHz, DMSO-d6): δ 3.32 ($CH_2CH_2$ backbone); 2.31 (C(O)—$CH_2$); 0.97 ($CH_3$). Additional signals were present for the terminal DMAEA group at δ 9.84 ($N^+H$), δ 8.18 (CO—NH—), δ 2.70 (N—$(CH_3)_2$).

Example 7. Synthesis of PEOZ-Cholamide 1K

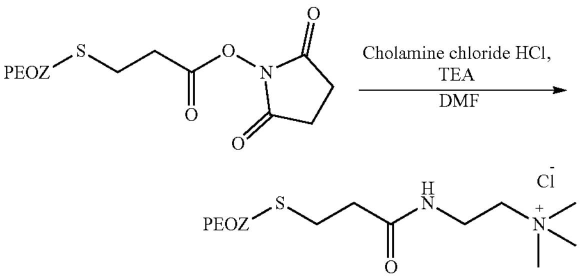

PEOZ-NHS Ester 1K (0.768 g, 0.706 mmol, 1.0 equiv.) in a 100 mL RB flask was dissolved in anhydrous DMF (20 mL). Under Ar atmosphere, cholamine chloride hydrochloride (0.136 g, 0.776 mmol, 1.1 equiv.) was added the clear solution, followed by addition of TEA (0.413 mL, 2.260 mmol, 4.2 equiv.). The clear solution was allowed to stir at room temperature overnight. Following overnight of reaction, the solution was evaporated to dryness by rotary evaporation. The residual solid was dissolved in 2 mM HCl (17 mL). The cloudy solution was filtered through a 0.2 μm GHP syringe filter, the clear filtrate was then purified by reversed phase chromatography using a Biotage SNAP Ultra C18 30 g column. The column was eluted with 2 mM HCl and methanol using a gradient. The elution was monitored using a UV detector. The desired fraction containing the product was collected, and evaporated by rotary evaporation to dryness. The remaining solid was dissolved in water (20 mL), followed by passing through a column packed with Amberlite IRA-67 media (5 gm) twice. The column was then eluted with water. The collected eluent (50 mL) was then lyophilized, which afforded 0.64 g of yellow colored solid.

$^1$HNMR analysis showed the standard signals for PEOZ Cholamide 1K (500 MHz, DMSO-d6): δ 3.32 ($CH_2CH_2$ backbone); 2.31 (C(O)—$CH_2$); 0.97 ($CH_3$). Additional signals were present for the terminal cholamide group at δ 8.41 (CO—NH—), δ 3.10 ($N^+$—$(CH_3)_3$).

Example 8. Synthesis of PEOZ 2K Cholamide

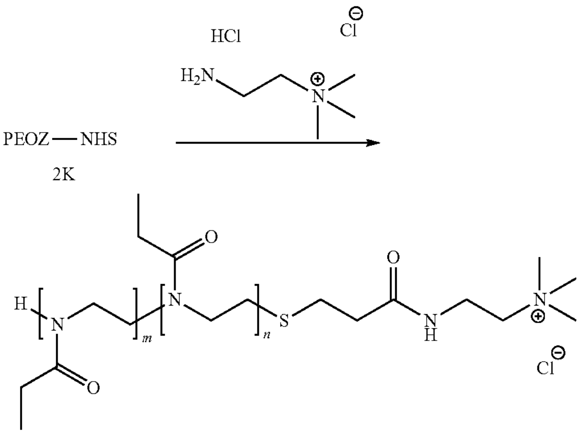

PEOZ-NHS (200.0 mg, 0.10 mmol, 2K Da, 1.0 equiv) and (2-aminoethyl)trimethylammonium chloride-HCl (21.2 mg, 0.120 mmol, 1.2 equiv) were added into a 2-dram vial. 0.1N boric acid (2 mL) was added and the mixture was stirred to dissolve completely. While stirring, pH of the solution was adjusted to 8.5 by addition of 0.1N NaOH(aq) solution dropwise. After the stirring overnight, the resulting mixture (pH 8.42) was passed through the amberlite column (IR120H/IRA67) and DEAE column. After the adjustment of pH as 5.0, the filtrate was freeze dried using a lyophilizer to give 74.0 mg (37% yield) of the desired product as a white crystalline.

$^1$H NMR (Varian, 500 MHz, 10 mg/mL DMSO-$d_6$, δ) analysis showed the standard backbone signals for PEOZ at 7.82 (terminal NH), 3.34 ($CH_2CH_2$ backbone), 3.16 (N—$CH_2$), 3.02 (—S—$CH_2$), 2.32-2.27 (C(O)—$CH_2$—), 0.94 (—$CH_3$). Additional signals were present for the cholamide moiety at 3.09 (s, —$CH_2N^{\oplus}(CH_3)_3$, 9H), 2.73 (m, —$NHCH_2CH_2NMe_3$, 2H), 2.40 (t, J=7.0 Hz, —$NHCH_2CH_2NMe_3$, 2H).

Example 9. Synthesis of $(EOZ)_{12}(CholamideOZ)_{6.5}$-OH 2K, PEOZ-OH 2K 5.8P Cholamide

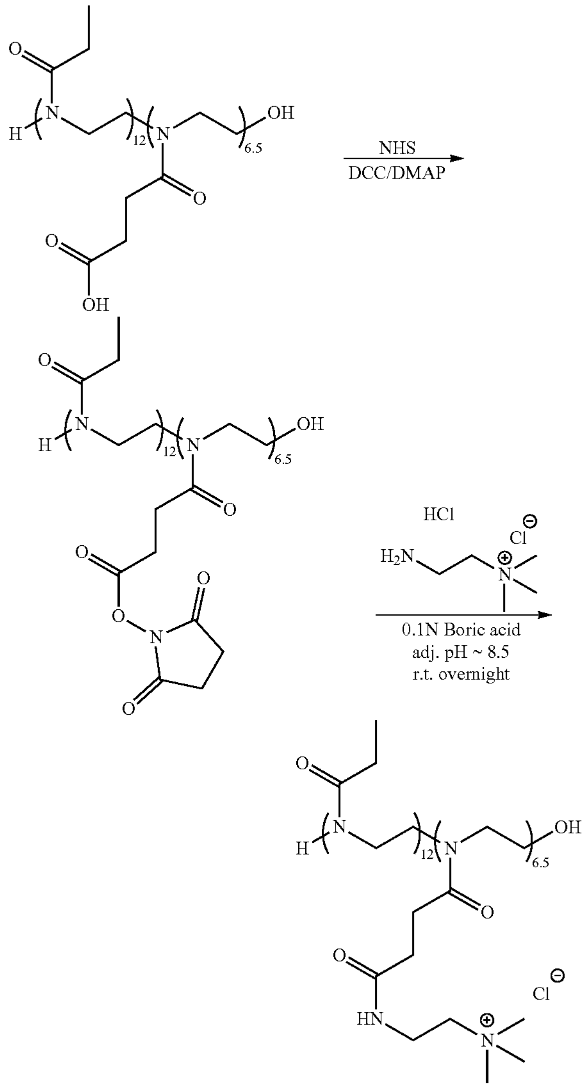

PEOZ-OH 6.5P NHS. PEOZ-OH 6.5P acid (0.499 g, 2460 Da, 0.203 mmol, 1.0 equiv) was added into a 25-mL flask, and dried by azeotrope using DMF (0.5 mL) and MeCN (10 mL). The residue was dissolved in 1.5 mL of DMF and then diluted with 9 mL of DCM to give a slightly cloudy solution. To the solution were added NHS (0.172 g, 1.462 mmol, 7.2 equiv) and DCC (0.305 g, 1.462 mmol, 7.2 equiv) followed by stirring for 18 hours. The reaction mixture was filtered using a syringe filter and the filtrate was concentrated using a rotary evaporator to give a thick oily crude. The crude product was dissolved in DCM and precipitated by adding into diethyl ether while stirring. The precipitate was filtered, collected and dried under a reduced pressure to give 0.63 g of the desired product as a white powder.

$^1H$ NMR (Varian, 500 MHz, 10 mg/mL DMSO-$d_6$, δ) analysis showed the standard backbone signals for PEOZ at 7.82 (terminal NH), 3.34 ($CH_2CH_2$ backbone), 3.16 (N—$CH_2$), 2.32-2.27 (C(O)—$CH_2$—), 0.94 (—$CH_3$). Signals for the pendant group were present at 2.88-2.55 ppm (—$CH_2CH_2CO_2H$ pendent), shifted down from 2.51-2.40 ppm due to the NHS ester formation. Additional signals were present for the NHS moiety at 2.78 ppm (—$CH_2CH_2$—NHS ring). The number of pendant groups was determined from the $^1H$ NMR analysis to be 6.5.

PEOZ-OH 2K 5.8P Cholamide (Calcd Mn 3370 Da). PEOZ-OH 2K 6.5P NHS (200.0 mg, 0.0646 mmol, 3100K Da, 1.0 equiv) and (2-aminoethyl)trimethylammonium chloride-HCl (85.0 mg, 0.485 mmol, 7.2 equiv) were added into a 20-mL vial. 0.1N boric acid (4 mL) was added and the mixture was stirred to dissolve completely. While stirring, pH of the solution was adjusted to 8.5 by addition of 0.1N NaOH(aq) solution dropwise. After the stirring overnight, the resulting mixture (pH 8.39) was passed through the amberlite column (IR120H/IRA67). The filtrate was freeze dried using a lyophilizer to give 156.4 mg (71.8% yield) of the desired product as a white crystalline.

$^1H$ NMR (Varian, 500 MHz, 10 mg/mL DMSO-$d_6$, δ) analysis showed the standard backbone signals for PEOZ at 3.30 ($CH_2CH_2$ backbone), 2.32-2.27 (C(O)—$CH_2$—), 0.95 (—$CH_3$). Additional signals were present for the cholamide moiety at 3.10 (s, —$CH_2N^{\oplus}(CH_3)_3$, 9H), 3.47 (m, —$NHCH_2CH_2NMe_3$, 2H), 2.40 (t, J=7.0 Hz, —$NHCH_2CH_2NMe_3$, 2H). The number of pendant cholamide groups was determined from the H NMR analysis to be 5.8.

Example 10. Synthesis of $(EOZ)_5(CholineEsterOZ)_5$-Pip-CholineEster

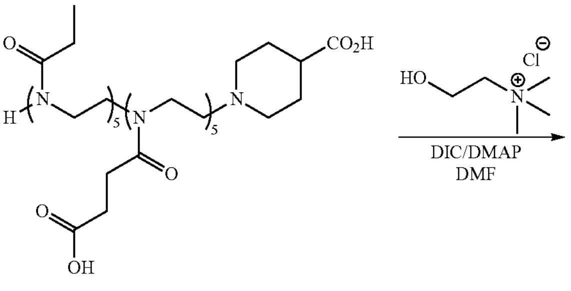

$P(EOZ)_5(PrAcidOZ)_5$-PipAcid

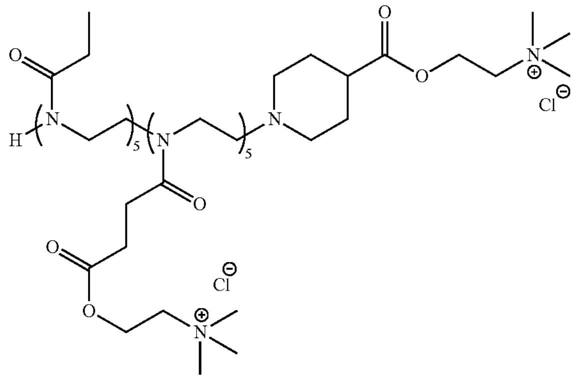

$P(EOZ)_5(PrChEOZ)_5$-PipChE

A 2-dram vial was charged with $(EOZ)_5(PrAcidOZ)_5$-Pip-COOH 1.3K (200.0 mg, 0.149 mmol, 1340 Da, 1.0 equiv), choline chloride (145.9 mg, 1.045 mmol, 7.0 equiv), and DMAP (18.6 mg, 0.152 mmol, 0.1 equiv) followed by a stir bar and DMF (3 mL) under an atmosphere of argon. After the addition of DIC (0.162 mL, 1.045 mmol, 7 equiv), the mixture was allowed to stir for 18 hours at room temperature. The reaction mixture was filtered using a syringe filter and the filtrate was concentrated down to around 1.5 mL followed by the precipitation using 18 mL of diethyl ether. Ether solution was decanted and the residue was stirred with a freshly added diethyl ether (15 mL). The white precipitate was filtered, collected, and dried in vacuo to give 208 mg (67% yield) of the desired product as a white crystalline.

$^1$H NMR (Varian, 500 MHz, 10 mg/mL DMSO-$d_6$, δ) analysis showed the standard backbone signals for PEOZ at 3.34 ($CH_2CH_2$ backbone), 3.15 (N—$CH_2$), 2.31 (—C(O)—$CH_2CH_3$), 2.05-1.53 (m, —$CH_2CH_2$— of terminal piperidine), 0.96 (—C(O)$CH_2CH_3$). Signals for the pendent and terminal choline moieties were present at 4.44 (br s, —$OCH_2CH_2N^{\oplus}(CH_3)_3$), 3.68 (br s, —$OCH_2CH_2N^{\oplus}(CH_3)_3$), 3.15 (br s, —$OCH_2CH_2N^{\oplus}(CH_3)_3$), 2.71 and 2.53 (—$CH_2CH_2C(O)O$— of pendent). The number of pendant choline groups was determined from the $^1$H NMR analysis to be 4.8.

Example 11. Synthesis of $(EOZ)_5(MePipEsterOZ)_n$-Pip-MePipEster 1.2K

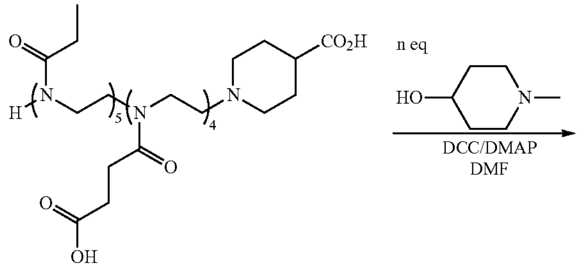

P(EOZ)5(PrAcidOZ)4-PipAcid

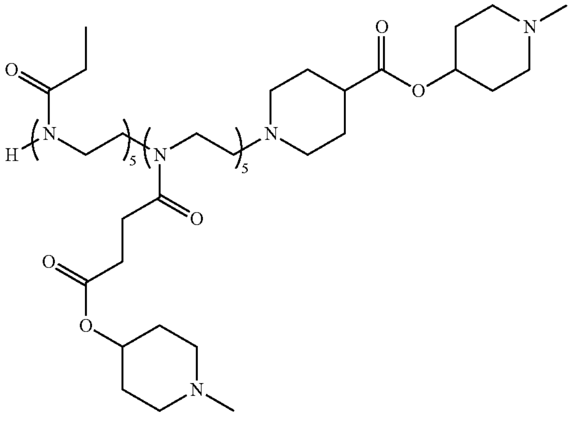

P(EOZ)5(MePipEOZ)n-MePipE

A 2-dram vial was charged with $(EOZ)_5(PrAcidOZ)_4$-Pip-COOH 1.2K, N-methyl-4-piperidinol, and DMAP followed by a stir bar and DMF under an atmosphere of argon. After the addition of DCC, the mixture was allowed to stir for 18 hours at room temperature. The reaction mixture was filtered using a syringe filter and the filtrate was concentrated. The residue was stirred with diethyl ether and then the solution was decanted. After the drying in vacuo, the resulting material dissolved in DCM and precipitated by adding into diethyl ether while stirring. The white precipitate was filtered, collected, and dried in vacuo to give the desired product as a white crystalline.

PEOZ-Pip 1.3K 1P MePipEster was synthesized using $(EOZ)_5(PrAcidOZ)_4$-Pip-COOH 1.2K (0.300 g, 0.212 mmol, 84.7 wt %, 1.0 equiv), N-methyl-4-piperidinol (0.035 g, 0.300 mmol, 1.42 equiv), DMAP (0.0061 g, 0.050 mmol, 0.24 equiv), DCC (0.0625 g, 0.300 mmol, 1.42 equiv), and DMF (3 mL), yielding 0.254 g (91% yield) of the desired product.

$^1$H NMR (Varian, 500 MHz, 10 mg/mL DMSO-$d_6$, δ) analysis showed the standard backbone signals for PEOZ at 3.34 ($CH_2CH_2$ backbone), 3.15 (N—$CH_2$), 2.31 (—C(O)—$CH_2CH_3$), 2.05-1.22 (m, —$CH_2CH_2$— of terminal piperidine), 0.94 (—C(O)$CH_2CH_3$). Signals for the pendent and terminal methyl piperidine moieties were present at 4.63 (br s, —OCH< of MePip), 2.03 (>$NCH_3$ of MePip), 2.84 and 2.49 (—$CH_2CH_2C(O)O$— of pendent). The number of pendent N-methyl piperidine groups was determined from the $^1$H NMR analysis to be 1.0.

PEOZ-Pip 1.3K 5P MePipEster was synthesized using $(EOZ)_5(PrAcidOZ)_4$-Pip-COOH 1.2K (0.312 g, 0.220 mmol, 84.7 wt %, 1.0 equiv), N-methyl-4-piperidinol (0.168 g, 1.431 mmol, 6.5 equiv), DMAP (0.0054 g, 0.044 mmol, 0.2 equiv), DCC (0.298 g, 1.431 mmol, 6.5 equiv), and DMF (3 mL), yielding 0.228 g (61% yield) of the desired product.

$^1$H NMR (Varian, 500 MHz, 10 mg/mL DMSO-$d_6$, δ) analysis showed the standard backbone signals for PEOZ at 3.34 ($CH_2CH_2$ backbone), 3.15 (N—$CH_2$), 2.31 (—C(O)—$CH_2CH_3$), 2.05-1.22 (m, —$CH_2CH_2$— of terminal piperidine), 0.94 (—C(O)$CH_2CH_3$). Signals for the pendent and terminal methyl piperidine moieties were present at 4.75 (br s, —OCH< of MePip). The number of pendent N-methyl piperidine groups was determined from the $^1$H NMR analysis to be 3.0.

Example 12. Synthesis of (N-methyl-4-piperidyl)-3-azidopropionate

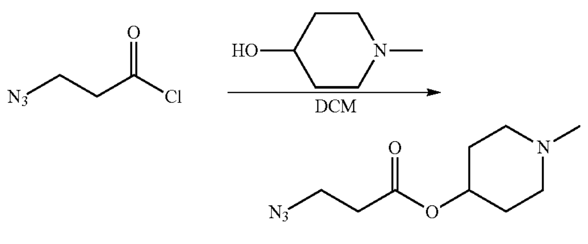

To a solution of N-methyl-4-piperidinol (0.14 g, 1.19 mmol, 1 equiv) in DCM (8 mL) was added 3-azidopropionyl chloride (0.330 g, 2.38 mmol, 96.5 wt %, 2 equiv) slowly at room temperature. After stirring for 18 hours, the reaction mixture was quenched with aqueous $NaHCO_3$, extracted with additional DCM, and the organic layer was collected, dried over $Na_2SO_4$, filtered, and concentrated under reduced pressure. Further purification was performed by Flash chromatography (DCM/MeOH, 9/1) yielding (N-methyl-4-piperidyl)-3-azidopropionate.

$^1$H NMR (Varian, 500 MHz, 10 mg/mL $CDCl_3$, 6) analysis showed the signals at 5.00 (br s, —OCH< of piperidine, 1H), 3.55 (t, $N_3CH_2CH_2$—, 2H), 2.96 (m, $CH_3NCH_2CH_2CHO$— of piperidine, 4H), 2.60 (t, $N_3CH_2CH_2$—, 2H), 2.60 (s, $CH_3$—Piperidine, 3H), 2.14 (m, $CH_3NCH_2CH_2CHO$— of piperidine, 2H), 1.95 (m, $CH_3NCH_2CH_2CHO$— of piperidine, 2H).

Example 13. Synthesis of (3-azidopropyl) N-methylpiperidinoate

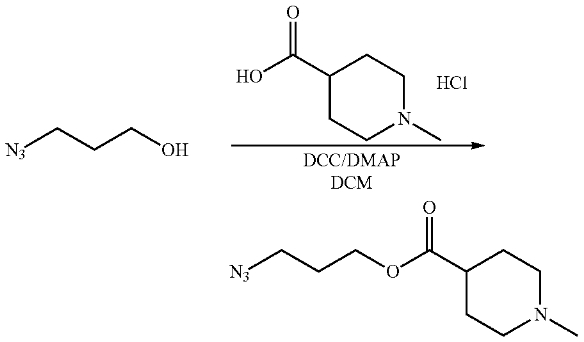

(3-azidopropyl) N-methylpiperidinoate

To a 100-mL round-bottom flask were added 3-azido-1-propanol (1.49 g, 14.2 mmol, 96+%, 1.0 eq.), 1-methylpiperidine-4-carboxylic acid HCl (2.80 g, 15.6 mmol, 1.0 eq.), anhydrous DCM (56 mL), and DMAP (0.173 g, 0.1 eq., 1.42 mmol). DCC (3.25 g, 1.1 eq., 15.6 mmol, 99%) was added into the solution and the resulting solution was allowed to stir for 18 hours at room temperature. The reaction mixture was filtered through a medium sintered glass frit, followed by rinsing the frit with additional DCM. The resulting solution was stirred for 5 minutes with saturated $NaHCO_3$ (25 mL). The organic phase was collected, dried over $Na_2SO_4$, filtered, and concentrated using a rotary evaporator. The residue purified by silica-gel column chromatography using Biotage, with a mixture of DCM and methanol as an eluting solvent to provide the desired product as a clear light yellow oil (2.95 g, 92% yield).

$^1H$ NMR (Varian, 500 MHz, 10 mg/mL $CDCl_3$, 6) analysis showed the signals at 4.17 (t, J=6.0 Hz, $N_3CH_2CH_2CH_2O$—, 2H), 3.38 (t, J=6.5 Hz, $N_3CH_2$—, 2H), 2.81 (br d, J=11.0 Hz, Pip(-CHH)$_2$CH—C(═O)O—, 2H), 2.28 (m, Pip(-$CH_2$)$_2$CH—C(═O)O—, 1H), 2.26 (s, Pip N—$CH_3$, 3H), 1.98 (t, J=11.3 Hz, Pip(-CHH)$_2$CH—C(═O)O—, 2H), 1.92 (t, J=6.5 Hz, $N_3CH_2CH_2$—, 2H), 1.91 (t, J=6.3 Hz, Pip(-CHH)$_2$N—$CH_3$, 2H), 1.78 (m, Pip(-CHH)$_2$N—$CH_3$, 2H).

Example 14. Synthesis of (Choline Iodide)-3-azidopropionate

Step 1: Synthesis of (2-dimethylamino)ethyl 3-azidopropionate

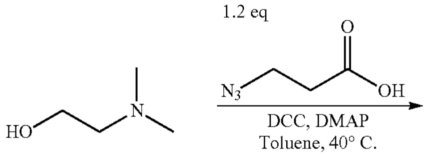

-continued

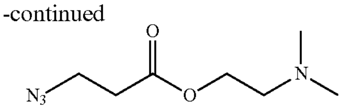

(2-dimethylamino)ethyl 3-azidopropionate

To a 250-mL round-bottom flask were added 2-dimethylaminoethanol (5.70 mL, 1.0 eq., 56.0 mmol, >99.5%), 3-azidopropionic acid (6.38 mL, 1.2 eq., 67.2 mmol, 97 wt %), anhydrous toluene (150 mL), and DMAP (0.68 g, 0.1 eq., 5.60 mmol). DCC (14.0 g, 1.2 eq., 67.2 mmol, 99%) was added into the solution and the resulting solution was allowed to stir for 18 hours at room temperature. The reaction mixture was filtered through a medium sintered glass frit, followed by rinsing the frit with additional toluene. The resulting solution was concentrated using a rotary evaporator, and the residue purified by silica-gel column chromatography using Biotage, with a mixture of ethyl acetate and methanol as an eluting solvent to provide the desired product as a clear yellow oil (4.68 g, 45% yield).

$^1H$ NMR (Varian, 500 MHz, 10 mg/mL DMSO-$d_6$, δ): 4.13 (t, 2H, J=6.00 Hz, —$OCH_2CH_2N(CH_3)_2$), 3.53 (t, 2H, J=6.25 Hz, $N_3CH_2CH_2$(C(═O)O—), 2.59 (t, 2H, J=6.25 Hz, $N_3CH_2CH_2$(C(═O)O—), 2.46 (t, 2H, J=6.00 Hz, —$OCH_2CH_2N(CH_3)_2$), 2.15 (s, 6H, —$N(CH_3)_2$).

Step 2: Synthesis of (Choline Iodide)-3-azidopropionate

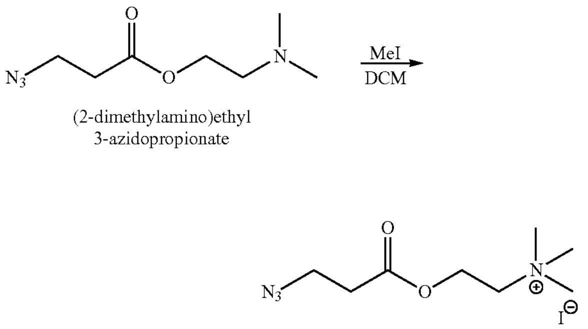

(2-dimethylamino)ethyl 3-azidopropionate (Choline iodide)-3-azidopropionate

To a solution of (2-Dimethylamino)ethyl3-azidopropionate (5.15 g, 27.7 mmol, 1.0 eq) in anhydrous DCM (40 mL) was slowly added methyl iodide (1.74 mL, 27.7 mmol, 1.0 eq). After the stirring for 18 hours, the reaction mixture (with pale yellow precipitate) was poured slowly into diethyl ether (500 mL) with vigorous stirring. The precipitate was isolated by filtration using a medium sintered glass frit, followed by rinsing with 200 mL of diethyl ether. The filtered white precipitate was transferred into a 50-mL bottle and dried in vacuo to give the desired product (8.39 g, 92.4% yield) as a pale-yellow powder.

$^1H$ NMR (Varian, 500 MHz, 10 mg/mL DMSO-$d_6$, δ): 4.48 (t, 2H, J=2.00 Hz, —$OCH_2CH_2N^{\oplus}(CH_3)_3$), 3.65 (t, 2H, J=2.25 Hz, —$OCH_2CH_2N^{\oplus}(CH_3)_3$), 3.58 (t, 2H, J=6.25 Hz, $N_3CH_2CH_2$(C(═O)O—), 3.11 (s, 9H, —$N^{\oplus}(CH_3)_3$), 2.65 (t, 2H, J=6.25 Hz, $N_3CH_2CH_2$(C(═O)O—).

Example 15. Synthesis of (Choline Iodide)-2-azidopropionate

Step 1: Synthesis of (2-dimethylamino)ethyl 2-azidopropionate

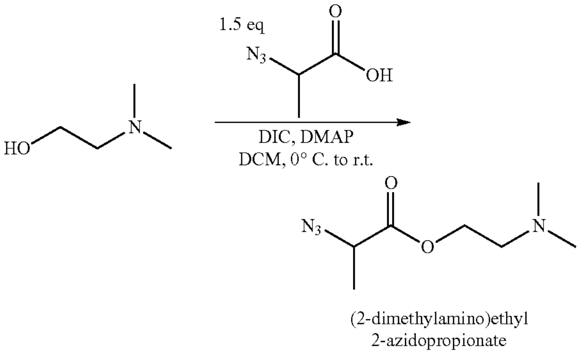

(2-dimethylamino)ethyl 2-azidopropionate

To a 250-mL round-bottom flask were added 2-dimethylaminoethanol (1.13 mL, 1.0 eq., 11.2 mmol, >99.5%), 2-azidopropionic acid (1.937 g, 1.5 eq., 16.8 mmol, 97 wt %), anhydrous DCM (25 mL), and DMAP (0.137 g, 0.1 eq., 1.12 mmol). DIC (2.63 mL, 1.5 eq., 16.8 mmol, 99%) was added into the solution and the resulting solution was allowed to stir for 18 hours at room temperature. The reaction mixture was filtered through a medium sintered glass frit, followed by rinsing the frit with additional toluene. The resulting solution was concentrated using a rotary evaporator, and the residue purified by silica-gel column chromatography using Biotage, with a mixture of ethyl acetate and methanol as an eluting solvent to provide the desired product as a clear yellow oil (1.34 g, 64% yield).

$^1$H NMR (Varian, 500 MHz, 10 mg/mL DMSO-$d_6$, δ): 4.29 (q, 1H, J=7.0 Hz, $N_3CH(CH_3)$ (C(═O)O—), 4.20 (m, 2H, —$OCH_2CH_2N(CH_3)_2$), 2.50 (t, 2H, J=5.5 Hz, —$OCH_2CH_2N(CH_3)_2$), 2.16 (s, 6H, —$N(CH_3)_2$), 1.33 (d, 3H, J=7.0 Hz, —$N_3CH(CH_3)$(C(═O)O—).

Step 2: Synthesis of (Choline Iodide)-3-azidopropionate

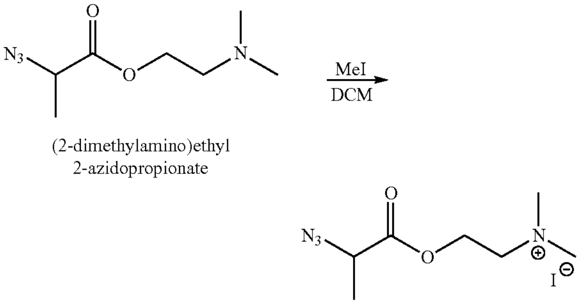

(2-dimethylamino)ethyl 2-azidopropionate (Choline iodide)-2-azidopropionate

To a solution of (2-Dimethylamino)ethyl 2-azidopropionate (1.30 g, 6.96 mmol, 1.0 eq) in anhydrous DCM (13 mL) was slowly added methyl iodide (0.44 mL, 6.96 mmol, 1.0 eq). After the stirring for 18 hours, the reaction mixture (with pale yellow precipitate) was poured slowly into diethyl ether (180 mL) with vigorous stirring. The precipitate was isolated by filtration using a medium sintered glass frit, followed by rinsing with 200 mL of diethyl ether. The filtered white precipitate was transferred into a 20-mL vial and dried in vacuo to give the desired product (1.76 g, 77.3% yield) as a pale-yellow powder.

$^1$H NMR (Varian, 500 MHz, 10 mg/mL DMSO-$d_6$, δ): 4.55 (m, 2H, —$OCH_2CH_2N^{\oplus}(CH_3)_3$), 4.38 (q, 1H, J=7.0 Hz, $N_3CH(CH_3)$(C(═O)O—), 3.69 (m, 2H, —$OCH_2CH_2N^{\oplus}(CH_3)_3$), 3.12 (s, 9H, —$N^{\oplus}(CH_3)_3$), 1.37 (d, 3H, J=7.0 Hz, $N_3CH(CH_3)$(C(═O)O—).

Example 16. Synthesis of $(PEOZ)_{13}(PtynOZ)_{9.5}$-OH 2.6K, (a.k.a. PEOZ-OH 2.6K 9.5p)

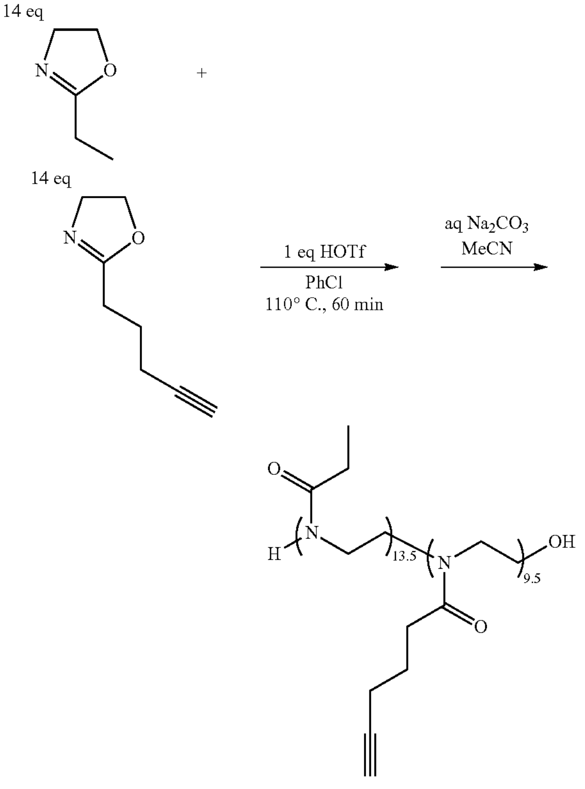

PEOZ—OH 2.6K 9.5p

An oven-dried 250-mL round bottomed flask, equipped with a reflux condenser and an argon gas inlet, was charged with 2-ethyl-2-oxazoline (15.680 g, 158.2 mmol, 14 equiv.) and 2-pentynyl-2-oxazoline (15.50 g, 113.0 mmol, 10 equiv.) followed by a stir bar and PhCl (135 mL) under argon atmosphere. TfOH (1.00 mL, 11.298 mmol, 1.00 equiv.) was added dropwise, and the mixture was allowed to stir at room temperature for 5 minutes. The reaction was then warmed to 110° C. over 20 minutes and stirred at that temperature for 40 minutes. After cooling to room temperature, the polymerization mixture was transferred to an oven-dried 1000-mL round bottomed flask and concentrated using a rotary evaporator to provide a sticky residue. After addition of $Na_2CO_3$ aqueous solution (452 mL, 0.2M, 2.00 equiv.), residual chlorobenzene was co-evaporated by azeotrope (total~100 mL). The resulting aqueous solution was diluted with MeCN (250 mL) and stirred overnight. After removing the MeCN and some of water using a rotary evaporator, the resulting aqueous solution was charged with NaCl (30.4 g, 10% w/w) and then product was extracted into DCM (2×300 mL). The combined organic phases were dried over $Na_2SO_4$, filtered, concentrated, and further dried in vacuo at 50° C. to provide the desired product (27.4 g, 92% yield) as a white crystalline.

$^1H$ NMR (Varian, 500 MHz, 10 mg/mL DMSO-$d_6$, δ) analysis showed the usual backbone peaks at 7.99 (br m, 1H, terminal NH), 3.34 (m, 4H, —$NCH_2CH_2N$-backbone), 3.16 (m, 2H, —N—$CH_2$), 2.32 and 2.27 (m, total area 2H, —C(═O)$CH_2CH_3$), and 0.96 (m, 3H, —C(═O)$CH_2CH_3$). The pendent pentynyl group peaks appear at 2.74 (br s, 1H, —$CH_2CH_2C$≡CH), 2.37 (m, 2H, —$CH_2CH_2CH_2C$≡CH), 2.15 (m, 2H, —$CH_2CH_2CH_2C$≡CH), and 1.64 (m, 2H, —$CH_2CH_2CH_2C$≡CH). The ratio of EOZ:PtynOZ was determined as 13.5:9.5. MALDI analysis showed Mn 2633 Da.

Example 17. Synthesis of PEOZ 2.6K 9p (Choline Iodide)-3-propionate

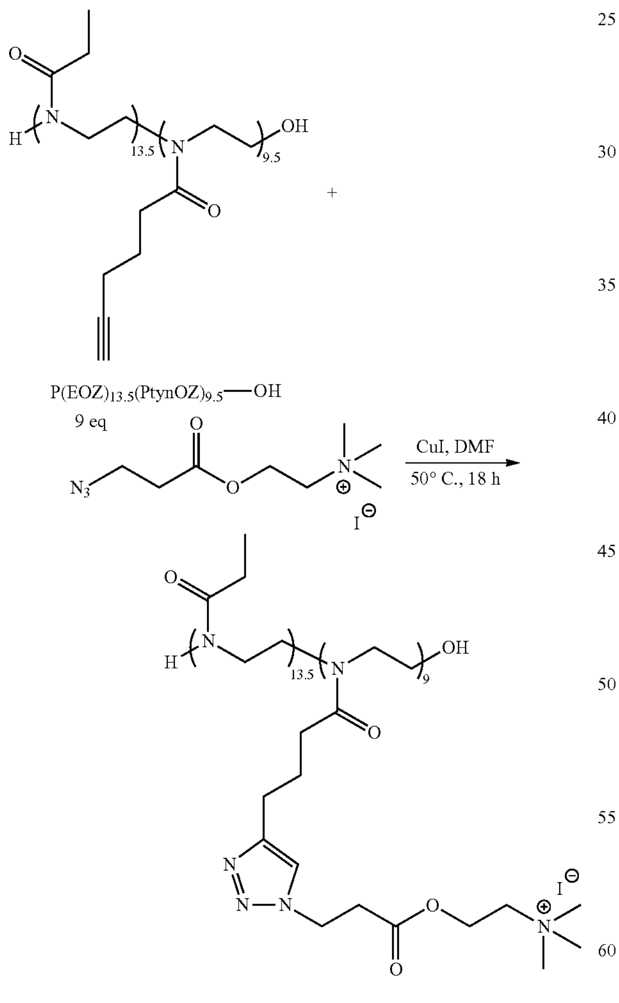

PEOZ—OH 2.6K 9p Choline ester

An oven-dried 25-mL round bottomed flask, equipped with a reflux condenser and an argon gas inlet, was charged with PEOZ-OH 2.6K 9.5p (0.100 g, 0.0380 mmol, 1.0 eq, Mn 2633 Da) and (choline iodide)-3-azidopropionate (0.112 g, 0.342 mmol, 9 eq) followed by a stir bar and DMF (3 mL) under argon atmosphere. After addition of CuI (0.0145 g, 0.0760 mmol, 2 eq), the resulting mixture was stirred for 5 minutes at room temperature and then allowed to stir for 18 hours at 50° C. After cooling down to room temperature, the reaction mixture was quenched by adding 0.5 N aqueous HCl (1 mL) followed by stirring for 5 minutes. The mixture was passed through the Dowex® M4195 column and the column was eluted with a mixture of DMF and water (9:1). The resulting solution was concentrated using a rotary evaporator at 34° C. The residue was purified by silica-gel column chromatography using a Biotage (SNAP Ultra C18 cartridge), with a mixture of water and methanol as an eluting solvent. After removing MeOH, the resulting aqueous solution was freeze-dried using a lyophilizer to provide the desired product (0.18 g, 90% yield) as a pale-yellow powder.

$^1H$ NMR (Varian, 500 MHz, 10 mg/mL DMSO-$d_6$, δ) analysis showed the standard backbone signals for PEOZ at 7.99 (br m, 1H, terminal NH), 3.34 (m, 4H, —$NCH_2CH_2N$-backbone), 3.16 (m, 2H, —N—$CH_2$), 2.32 and 2.27 (m, total area 2H, —C(═O)$CH_2CH_3$), and 0.94 (m, 3H, —C(═O)$CH_2CH_3$). Signals for the pendant group were present at 7.91 (br s, 1H, triazole ring, resulted by 'click' reaction), 4.55 (m, 2H, triazole N—$CH_2CH_2C$(═O)O—), 4.46 (m, 2H, —$OCH_2CH_2N^{\oplus}(CH_3)_3$), 3.65 (m, 2H, —$OCH_2CH_2N^{\oplus}(CH_3)_3$), 3.12 (s, 9H, —$N^{\oplus}(CH_3)_3$), and 2.62-2.58 (m, 2H, triazole N—$CH_2CH_2C$(═O)O—). Additionally, two types of pendant pentynyl group peaks appear at 1.78 (m, 2H, backbone-$CH_2CH_2CH_2$-triazole ring, 'clicked') and 1.64 (m, 2H, backbone-$CH_2CH_2CH_2C$≡CH, intact). The number of pendant groups was determined from the $^1H$ NMR analysis to be 8.15 by comparing the integrations of pendant group protons and polymer backbone protons, and the calculated molecular weight was 5307 Da.

Example 18. Synthesis of PEOZ 2.6K 9p NMPOH

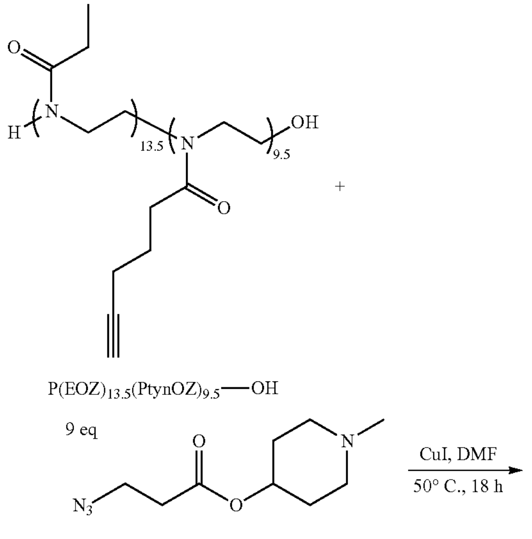

N-methylpiperidyl azidopropionate

-continued

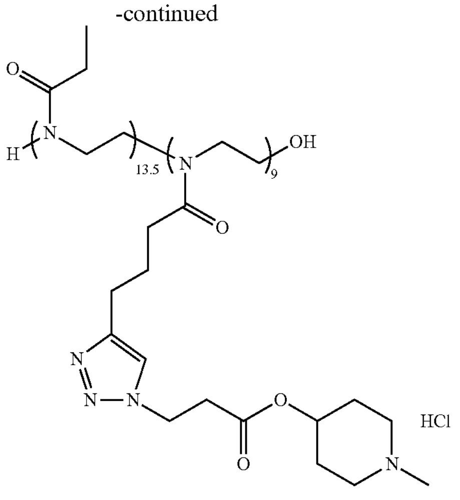

PEOZ—OH 2K 9p MPOH

An oven-dried 25-mL round bottomed flask, equipped with a reflux condenser and an argon gas inlet, was charged with PEOZ-OH 2.6K 9.5p (0.793 g, 0.301 mmol, 1.0 eq, Mn 2633 Da) and (N-methyl-4-piperidyl)-3-azidopropionate (0.576 g, 2.710 mmol, 9 eq) followed by a stir bar and THE (8 mL) under argon atmosphere. After addition of CuI (0.115 g, 0.602 mmol, 2 eq), the resulting mixture was stirred for 5 minutes at room temperature and then allowed to stir for 18 hours at 50° C. After cooling down to room temperature, the reaction mixture was quenched by adding 0.5 N aqueous HCl (6 mL) followed by stirring for 5 minutes. The mixture was passed through the Dowex® M4195 column and the column was eluted with a mixture of THE and water (9:1). The resulting solution was concentrated using a rotary evaporator at 34° C. The residue was purified by dissolving in MeOH and precipitation by addition to MTBE. After filtration, the resulting precipitate was freeze-dried using a lyophilizer to provide the desired product (1.11 g, 83% yield) as a pale-yellow powder.

$^1$H NMR (Varian, 500 MHz, 10 mg/mL DMSO-$d_6$, δ) analysis showed the standard backbone signals for PEOZ at 7.93 (br m, 1H, terminal NH), 3.34 (m, 4H, —$NCH_2CH_2N$— backbone), 3.16 (m, 2H, —N—$CH_2$), 2.31 and 2.27 (m, total area 2H, —C(═O)$CH_2CH_3$), and 0.93 (m, 3H, —C(═O)$CH_2CH_3$). Signals for the pendant group were present at 7.93 (br s, 1H, triazole ring, resulted by 'click' reaction), 4.83 (br s, —OCH< of piperidine, 1H), 4.55 (m, 2H, triazole N—$CH_2CH_2C$(═O)O—), 2.96 (m, $CH_3NCH_2CH_2CHO$— of piperidine, 4H), and 2.60 (m, 2H, triazole N—$CH_2CH_2C$(═O)O—), 2.60 (br s, $CH_3$—Piperidine, 3H), 1.95 (m, $CH_3NCH_2CH_2CHO$— of piperidine, 2H), and 1.62 (m, $CH_3NCH_2CH_2CHO$— of piperidine, 2H). Additionally, two types of pendant pentynyl group peaks appear at 1.76 (m, 2H, backbone-$CH_2CH_2CH_2$-triazole ring, 'clicked') and 1.62 (m, 2H, backbone-$CH_2CH_2CH_2C$≡CH, intact). The number of pendant groups was determined from the $^1$H NMR analysis to be 8.3 by comparing the integrations of pendant group protons and polymer backbone protons, and the calculated molecular weight was 4700 Da.

Example 19. Synthesis of PEOZ 2.6K 9p NMPCA

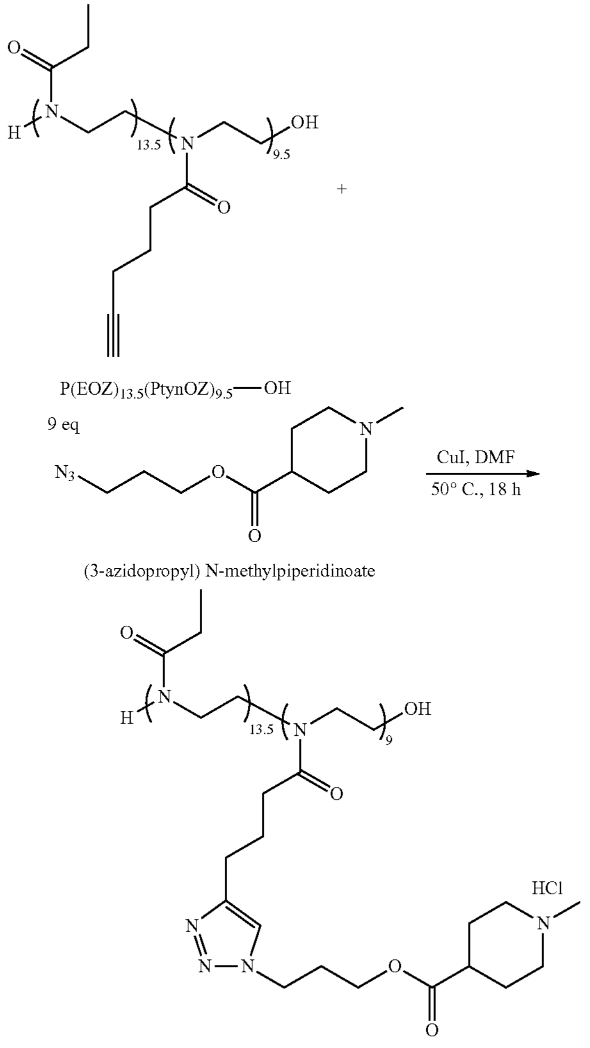

PEOZ—OH 2.6K 9p NMPCA

An oven-dried 25-mL round bottomed flask, equipped with a reflux condenser and an argon gas inlet, was charged with PEOZ-OH 2.6K 9.5p (1.00 g, 0.380 mmol, 1.0 eq, Mn 2633 Da) and (3-azidopropyl) N-methylpiperidinoate (0.774 g, 3.418 mmol, 9 eq) followed by a stir bar and THE (10 mL) under argon atmosphere. After addition of CuI (0.145 g, 0.760 mmol, 2 eq), the resulting mixture was stirred for 5 minutes at room temperature and then allowed to stir for 18 hours at 50° C. After cooling down to room temperature, the reaction mixture was quenched by adding 2 N aqueous HCl (1.7 mL) followed by stirring for 5 minutes. The mixture was passed through the Dowex® M4195 column and the column was eluted with a mixture of THE and water (9:1). The resulting solution was concentrated using a rotary evaporator at 34° C. The residue was purified by dissolving in MeOH and precipitation by addition to MTBE. After filtration, the resulting precipitate was freeze-dried using a lyophilizer to provide the desired product (1.73 g, 91% yield) as a pale-yellow powder.

$^1$H NMR (Varian, 500 MHz, 10 mg/mL DMSO-$d_6$, δ) analysis showed the standard backbone signals for PEOZ at 7.93 (br m, 1H, terminal NH), 3.34 (m, 4H, $—NCH_2CH_2N$-backbone), 3.16 (m, 2H, $—N—CH_2$), 2.31 and 2.27 (m, total area 2H, $—C(=O)CH_2CH_3$), and 0.93 (m, 3H, $—C(=O)CH_2CH_3$). Signals for the pendant group were present at 7.87 (br s, 1H, triazole ring, resulted by 'click' reaction), 4.37 (m, 2H, triazole $N—CH_2CH_2CH_2CO—$), 4.01 (m, 2H, $N_3CH_2CH_2CH_2O—$), 2.90 (m, 2H, Pip($-CHH)_2CH—C(=O)O—$), 2.65 (m, 2H Pip($-CHH)_2CH—C(=O)O—$), 2.65 (m, 1H, Pip($-CH_2)_2CH—C(=O)O—$, 1H), 2.57 (s, 3H, Pip $N—CH_3$), 1.97 (m, 2H, triazole $N—CH_2CH_2—$, 2H), and 1.84-1.77 (m, 4H, $CH_3NCH_2—$ of piperidine). Additionally, two types of pendant pentynyl group peaks appear at 1.77 (m, 2H, backbone-$CH_2CH_2CH_2$-triazole ring, 'clicked') and 1.62 (m, 2H, backbone-$CH_2CH_2CH_2C{\equiv}CH$, intact). The number of pendant groups was determined from the $^1H$ NMR analysis to be 9.0 by comparing the integrations of pendant group protons and polymer backbone protons, and the calculated molecular weight was 5000 Da.

Example 20. Synthesis of $(PEOZ)_{15}(PtynOZ)_5$-OH 2.3K, (a.k.a. PEOZ-OH 2.3K 5p)

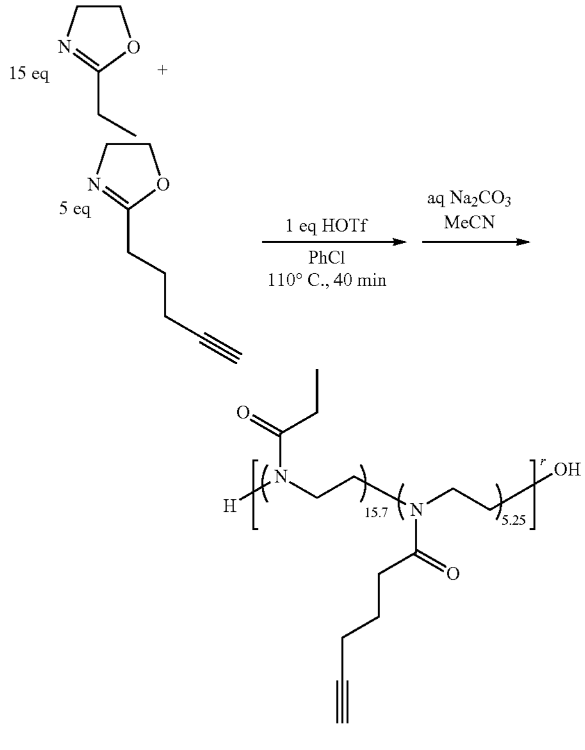

PEOZ—OH 2.3K 5.25p

An oven-dried 250-mL round bottomed flask, equipped with a reflux condenser and an argon gas inlet, was charged with 2-ethyl-2-oxazoline (16.845 g, 169.6 mmol, 15 equiv.) and 2-pentynyl-2-oxazoline (7.735 g, 56.49 mmol, 5 equiv.) followed by a stir bar and PhCl (118 mL) under argon atmosphere. TfOH (1.00 mL, 11.298 mmol, 1.00 equiv.) was added dropwise, and the mixture was allowed to stir at room temperature for 5 minutes. The reaction was then warmed to 110° C. over 20 minutes and stirred at that temperature for 40 minutes. After cooling to room temperature, the polymerization mixture was transferred to an oven-dried 1000-mL round bottomed flask and concentrated using a rotary evaporator to provide a sticky residue. After addition of $Na_2CO_3$ aqueous solution (452 mL, 0.2M, 2.00 equiv.), residual chlorobenzene was co-evaporated by azeotrope (total~100 mL). The resulting aqueous solution was diluted with MeCN (250 mL) and stirred overnight. After removing the MeCN and some of water using a rotary evaporator, the resulting aqueous solution (304 g) was charged with NaCl (30.4 g, 10% w/w) and then product was extracted into DCM (2×300 mL). The combined organic phases were dried over $Na_2SO_4$, filtered, concentrated, and further dried in vacuo at 50° C. to provide the desired product (23.2 g, 94.5% yield) as a white crystalline.

$^1H$ NMR (Varian, 500 MHz, 10 mg/mL DMSO-$d_6$, δ) analysis showed the usual backbone peaks at 7.99 (br m, 1H, terminal NH), 3.34 (m, 4H, $—NCH_2CH_2N$-backbone), 3.16 (m, 2H, $—N—CH_2$), 2.32 and 2.27 (m, total area 2H, $—C(=O)CH_2CH_3$), and 0.96 (m, 3H, $—C(=O)CH_2CH_3$). The pendent pentynyl group peaks appear at 2.74 (br s, 1H, $—CH_2CH_2C{\equiv}CH$), 2.37 (m, 2H, $—CH_2CH_2CH_2C{\equiv}CH$), 2.15 (m, 2H, $—CH_2CH_2CH_2C{\equiv}CH$), and 1.64 (m, 2H, $—CH_2CH_2CH_2C{\equiv}CH$). The ratio of EOZ:PtynOZ was determined as 15.73:5.25. MALDI analysis showed Mn 2279 Da and PDI 1.04.

Example 21. Synthesis of $(PrOZ)_{15}(PtynOZ)_5$-OH 2.6K, (a.k.a. PPOZ-OH 2.6K 5p)

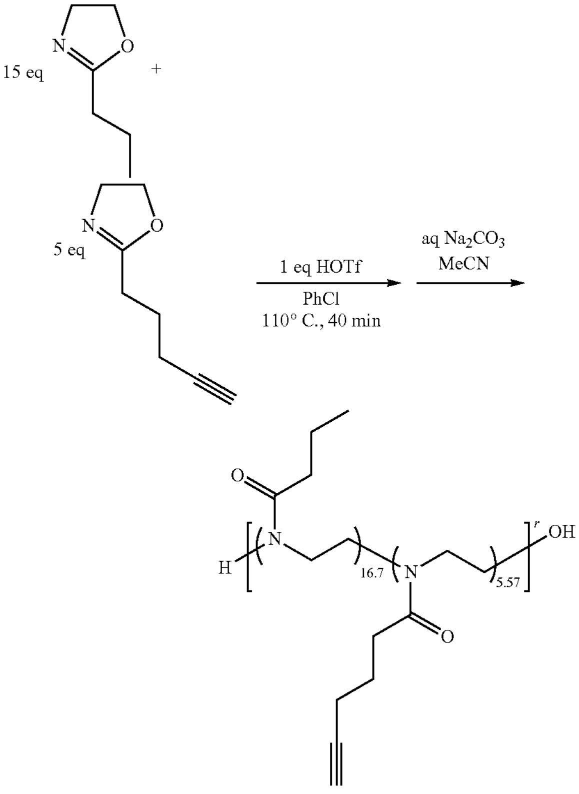

PPOZ—OH 2.6K 5.57p

An oven-dried 100-mL round bottomed flask, equipped with a reflux condenser and an argon gas inlet, was charged with 2-propyl-2-oxazoline (7.129 g, 63.0 mmol, 15 equiv.) and 2-pentynyl-2-oxazoline (2.881 g, 14.4 mmol, 5 equiv.) followed by a stir bar and PhCl (13 mL) under argon atmosphere. TfOH (371.2 μL, 4.20 mmol, 1.00 equiv.) was added dropwise, and the mixture was allowed to stir at room temperature for 5 minutes. The reaction was then warmed to 110° C. over 20 minutes and stirred at that temperature for 40 minutes. The polymerization mixture was then cooled to room temperature and most of the solvent was removed using a rotary evaporator. After addition of $Na_2CO_3$ aqueous solution (42 mL, 0.4M, 4.00 equiv.), residual chlorobenzene was co-evaporated by azeotrope. The resulting aqueous solution was diluted with MeCN (40 mL) and stirred overnight. After removing the MeCN using a rotary evaporator, the product was extracted into DCM. The combined organic phases were dried over $Na_2SO_4$, filtered, concentrated, and further dried in vacuo to provide the desired product (9.7 g, 97% yield) as a white crystalline.

$^1$H NMR (Varian, 500 MHz, 10 mg/mL DMSO-$d_6$, δ) analysis showed the usual backbone peaks at 7.99 (br m, 1H, terminal NH), 3.34 (m, 4H, —$NCH_2CH_2N$— backbone), 3.16 (m, 2H, —N—$CH_2$), 2.27 and 2.22 (m, total area 2H, —C(═O)$CH_2CH_2CH_3$), 1.48 (m, 2H, —C(═O)$CH_2CH_2CH_3$), and 0.84 (m, 3H, —C(═O)$CH_2CH_2CH_3$). The pendent pentynyl group peaks appear at 2.73 (br s, 1H, —$CH_2CH_2C{\equiv}CH$), 2.36 (m, 2H, —$CH_2CH_2CH_2C{\equiv}CH$), 2.15 (m, 2H, —$CH_2CH_2CH_2C{\equiv}CH$), and 1.64 (m, 2H, —$CH_2CH_2CH_2C{\equiv}CH$). The ratio of PrOZ:PtynOZ was determined as 16.7:5.57. MALDI analysis showed Mn 2670 Da and PDI 1.05.

Example 22. Synthesis of PEOZ 2.3K 1.4p (Choline Iodide)-2-propionate

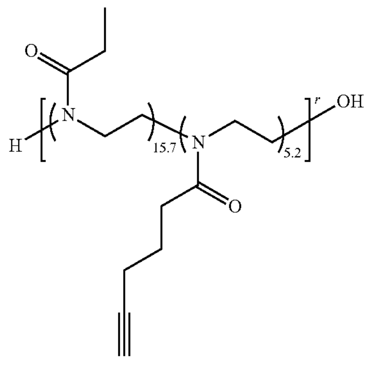

+

$P(EOZ)_{15.7}(PtynOZ)_{5.2}$—OH

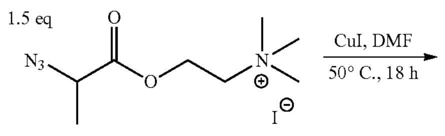

(Choline iodide)-2-azidopropionate

-continued

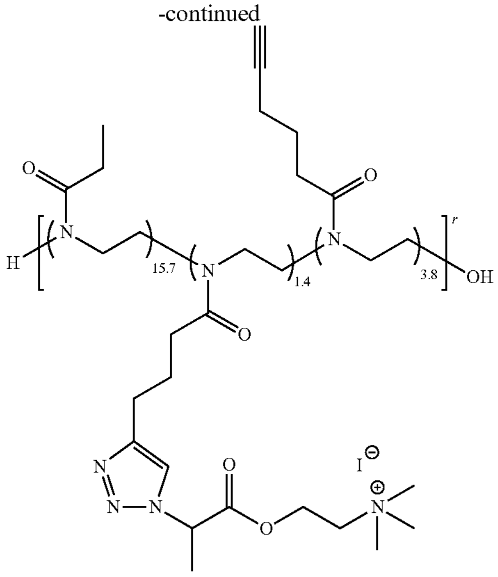

PEOZ—OH 2.3K 1.4p (choline iodide)-2-propionate Mn 2738 Da

An oven-dried 25-mL round bottomed flask, equipped with a reflux condenser and an argon gas inlet, was charged with PEOZ-OH 2.3K 5.2p (1.00 g, 0.439 mmol, 1.0 eq, Mn 2279 Da) and (choline iodide)-2-azidopropionate (0.216 g, 0.658 mmol, 1.5 eq) followed by a stir bar and DMF (10 mL) under argon atmosphere. After addition of CuI (0.042 g, 0.219 mmol, 0.5 eq), the resulting mixture was stirred for 5 minutes at room temperature and then allowed to stir for 18 hours at 50° C. After cooling down to room temperature, the reaction mixture was quenched by adding 1.0 N aqueous HCl (2.5 mL) followed by stirring for 5 minutes. The mixture was passed through the Dowex® M4195 column and the column was eluted with a mixture of DMF and water (4:1). The resulting solution was concentrated using a rotary evaporator at 34° C. The residue was purified by silica-gel column chromatography using a Biotage (SNAP Ultra C18 cartridge), with a mixture of water and methanol as an eluting solvent. After removing MeOH, the resulting aqueous solution was freeze-dried using a lyophilizer to provide the desired product (1.04 g, 85% yield) as a pale-yellow powder.

$^1$H NMR (Varian, 500 MHz, 10 mg/mL DMSO-$d_6$, δ) analysis showed the standard backbone signals for PEOZ at 7.99 (br m, 1H, terminal NH), 3.34 (m, 4H, —$NCH_2CH_2N$— backbone), 3.16 (m, 2H, —N—$CH_2$), 2.75 (br s, 1H, —$CH_2CH_2C{\equiv}CH$, intact), 2.32 and 2.27 (m, total area 2H, —C(═O)$CH_2CH_3$), and 0.94 (m, 3H, —C(═O)$CH_2CH_3$). Signals for the pendant group were present at 7.92 (br s, 1H, triazole ring, resulted by 'click' reaction), 5.64 (m, 2H, triazole N—CH($CH_3$)C(═O)O—), 4.52 (m, 2H, —$OCH_2CH_2N^{\oplus}(CH_3)_3$), 3.66 (m, 2H, —$OCH_2CH_2N^{\oplus}(CH_3)_3$), 3.05 (s, 9H, —$N^{\oplus}(CH_3)_3$), and 1.75 (d, 3H, J=7.0 Hz, triazole N—CH($CH_3$)(C(═O)O—). Additionally, two types of pendant pentynyl group peaks appear at 1.79 (m, 2H, backbone-$CH_2CH_2CH_2$-triazole ring, 'clicked') and 1.64 (m, 2H, backbone-$CH_2CH_2CH_2C{\equiv}CH$, intact). The number of pendant groups was determined from the $^1$H NMR analysis to be 1.4 by comparing the integrations of pendant group protons and polymer backbone protons, and the calculated molecular weight was 2738 Da.

Synthesis of PEOZ-OH 2.3K np Choline 3-propionate

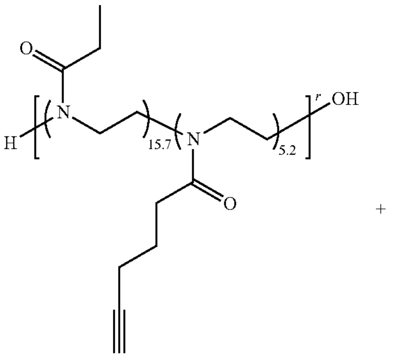

PEOZ—OH 2.3K 5.2 p

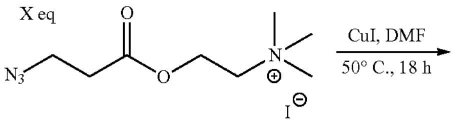

(Choline iodide)-2-azidopropionate

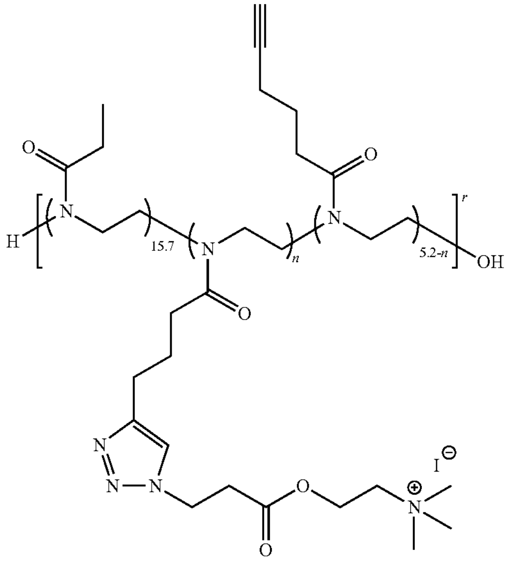

PEOZ—OH 2.3K np (Choline iodide)-3-propionate

Example 23. Synthesis of PEOZ 2.3K 1p (Choline Iodide)-3-propionate, (where n=1)

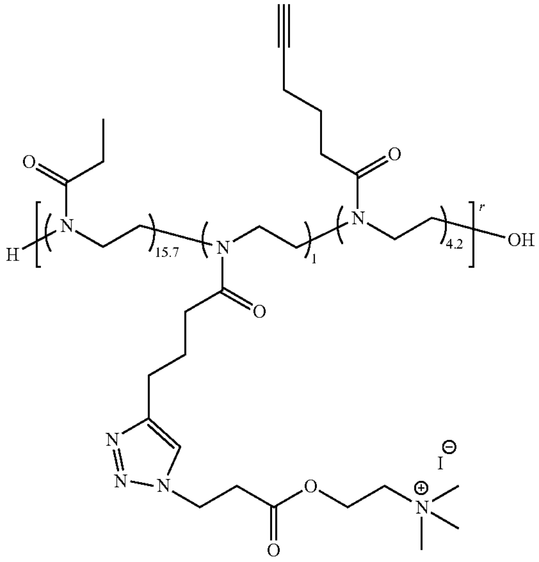

PEOZ—OH 2.3K 1p (Choline iodide)-3-propionate

An oven-dried 25-mL round bottomed flask, equipped with a reflux condenser and an argon gas inlet, was charged with PEOZ-OH 2.3K 5.2p (0.80 g, 0.351 mmol, 1.0 eq, Mn 2279 Da) and (choline iodide)-3-azidopropionate (0.138 g, 0.421 mmol, 1.2 eq) followed by a stir bar and DMF (8 mL) under argon atmosphere. After addition of CuI (0.167 g, 0.878 mmol, 2.5 eq), the resulting mixture was stirred for 5 minutes at room temperature and then allowed to stir for 18 hours at 50° C. After cooling down to room temperature, the reaction mixture was quenched by adding 1.0 N aqueous HCl (2.5 mL) followed by stirring for 5 minutes. The mixture was passed through the Dowex® M4195 column and the column was eluted with a mixture of DMF and water (4:1). The resulting solution was concentrated using a rotary evaporator at 34° C. The residue was purified by silica-gel column chromatography using a Biotage (SNAP Ultra C18 cartridge), with a mixture of water and methanol as an eluting solvent. After removing MeOH, the resulting aqueous solution was freeze-dried using a lyophilizer to provide the desired product (0.76 g, 83% yield) as a pale-yellow powder.

$^1H$ NMR (Varian, 500 MHz, 10 mg/mL DMSO-$d_6$, δ) analysis showed the standard backbone signals for PEOZ at 7.99 (br m, 1H, terminal NH), 3.34 (m, 4H, —$NCH_2CH_2N$— backbone), 3.16 (m, 2H, —N—$CH_2$), 2.32 and 2.27 (m, total area 2H, —C(═O)$CH_2CH_3$), and 0.94 (m, 3H, —C(═O)$CH_2CH_3$). Signals for the pendant group were present at 7.91 (br s, 1H, triazole ring, resulted by 'click' reaction), 4.55 (m, 2H, triazole N—$CH_2CH_2$C(═O)O—), 4.46 (m, 2H, —$OCH_2CH_2N^{\oplus}(CH_3)_3$), 3.65 (m, 2H, —$OCH_2CH_2N^{\oplus}(CH_3)_3$), 3.12 (s, 9H, —$N^{\oplus}(CH_3)_3$), and 2.62-2.58 (m, 2H, triazole N—$CH_2CH_2$C(═O)O—). Additionally, two types of pendant pentynyl group peaks appear at 1.78 (m, 2H, backbone-$CH_2CH_2CH_2$-triazole ring, 'clicked') and 1.64 (m, 2H, backbone-$CH_2CH_2CH_2C{\equiv}CH$, intact). The number of pendant groups was determined from the $^1H$ NMR analysis to be 1.0 by comparing the integrations of pendant group protons and polymer backbone protons, and the calculated molecular weight was 2607 Da.

Example 24. Synthesis of PEOZ 2.3K 3p (Choline Iodide)-3-propionate, (where n=3)

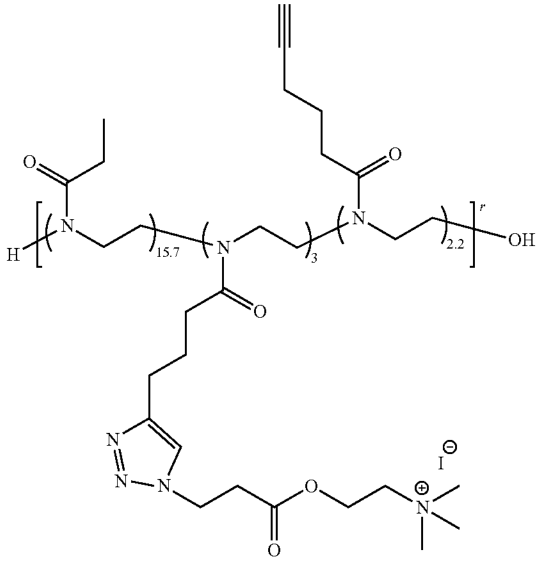

PEOZ—OH 2.3K 3p (Choline iodide)-3-propionate

An oven-dried 25-mL round bottomed flask, equipped with a reflux condenser and an argon gas inlet, was charged with PEOZ-OH 2.3K 5.2p (0.80 g, 0.351 mmol, 1.0 eq, Mn 2279 Da) and (choline iodide)-3-azidopropionate (0.363 g, 1.106 mmol, 3.15 eq) followed by a stir bar and DMF (14 mL) under argon atmosphere. After addition of CuI (0.167 g, 0.878 mmol, 2.5 eq), the resulting mixture was stirred for 5 minutes at room temperature and then allowed to stir for 18 hours at 50° C. After cooling down to room temperature, the reaction mixture was quenched by adding 1.0 N aqueous HCl (4 mL) followed by stirring for 5 minutes. The mixture was passed through the Dowex® M4195 column and the column was eluted with a mixture of DMF and water (4:1). The resulting solution was concentrated using a rotary evaporator at 34° C. The residue was purified by silica-gel column chromatography using a Biotage (SNAP Ultra C18 cartridge), with a mixture of water and methanol as an eluting solvent. After removing MeOH, the resulting aqueous solution was freeze-dried using a lyophilizer to provide the desired product (0.93 g, 81% yield) as a pale-yellow powder.

The attachment of (choline iodide)-3-azidopropionate was proved by $^1H$ NMR (Varian, 500 MHz, 10 mg/mL DMSO-d6) that showed the peaks at 7.90 (br s, 1H, triazole ring, resulted by 'click' reaction), 4.56 (m, 2H, triazole N—$CH_2CH_2C$(=O)O—), 4.45 (m, 2H, —$OCH_2CH_2N^{\oplus}(CH_3)_3$), 3.68 (m, 2H, —$OCH_2CH_2N^{\oplus}(CH_3)_3$), 3.12 (s, 9H, —$N^{\oplus}(CH_3)_3$), and 2.57 (m, 2H, triazole N—$CH_2CH_2C$(=O)O—), besides the usual polymer backbone peaks. Additionally, two types of pendant pentynyl group peaks appear at 1.76 (m, 2H, backbone-$CH_2CH_2CH_2$— triazole ring, 'clicked') and 1.63 (m, 2H, backbone-$CH_2CH_2CH_2C{\equiv}CH$, intact). The number of pendant groups was determined from the $^1H$ NMR analysis to be 3.07 by comparing the integrations of pendant group protons and polymer backbone protons, and the calculated molecular weight was 3263 Da.

Example 25. Synthesis of PEOZ 2.3K 5p (Choline Iodide)-3-propionate, (where n=5)

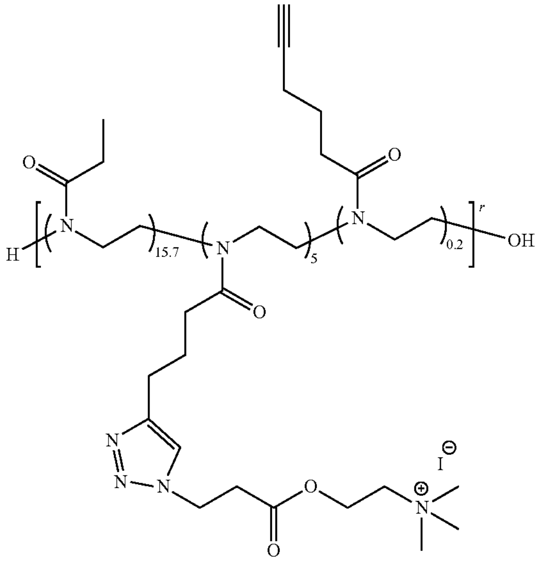

PEOZ—OH 2.3K 5p (Choline iodide)-3-propionate

An oven-dried 50-mL round bottomed flask, equipped with a reflux condenser and an argon gas inlet, was charged with PEOZ-OH 2.3K 5.2p (0.80 g, 0.351 mmol, 1.0 eq, Mn 2279 Da) and (choline iodide)-3-azidopropionate (0.599 g, 1.825 mmol, 5.2 eq) followed by a stir bar and DMF (16 mL) under argon atmosphere. After addition of CuI (0.167 g, 0.878 mmol, 2.5 eq), the resulting mixture was stirred for 5 minutes at room temperature and then allowed to stir for 18 hours at 50° C. After cooling down to room temperature, the reaction mixture was quenched by adding 1.0 N aqueous HCl (8 mL) followed by stirring for 5 minutes. The mixture was passed through the Dowex® M4195 column and the column was eluted with a mixture of DMF and water (4:1). The resulting solution was concentrated using a rotary evaporator at 34° C. The residue was purified by silica-gel column chromatography using a Biotage (SNAP Ultra C18 cartridge), with a mixture of water and methanol as an eluting solvent. After removing MeOH, the resulting aqueous solution was freeze-dried using a lyophilizer to provide the desired product (1.27 g, 82% yield) as a pale-yellow powder.

The attachment of (choline iodide)-3-azidopropionate was proved by $^1H$ NMR (Varian, 500 MHz, 10 mg/mL DMSO-d6) that showed the peaks at 7.90 (br s, 1H, triazole ring, resulted by 'click' reaction), 4.56 (m, 2H, triazole N—$CH_2CH_2C$(=O)O—), 4.46 (m, 2H, —$OCH_2CH_2N^{\oplus}(CH_3)_3$), 3.68 (m, 2H, —$OCH_2CH_2N^{\oplus}(CH_3)_3$), 3.12 (s, 9H, —$N^{\oplus}(CH_3)_3$), and 2.57 (m, 2H, triazole N—$CH_2CH_2C$(=O)O—), besides the usual polymer backbone peaks. Additionally, two types of pendant pentynyl group peaks appear at 1.76 (m, 2H, backbone-$CH_2CH_2CH_2$— triazole ring, 'clicked') and 1.63 (m, 2H, backbone-$CH_2CH_2CH_2C{\equiv}CH$, intact). The number of pendant groups was determined from the $^1H$ NMR analysis to be 5.03 by comparing the integrations of pendant group protons and polymer backbone protons, and the calculated molecular weight was 3920 Da.

Synthesis of PEOZ-OH 2.3K np NMPCA

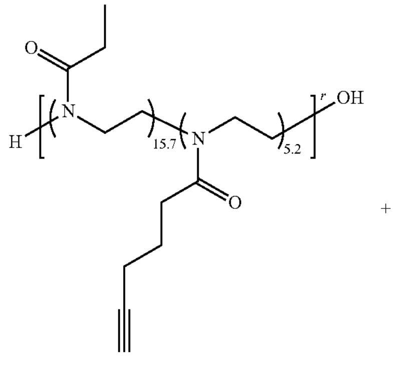

+

PEOZ—OH 2.3K 5.2p

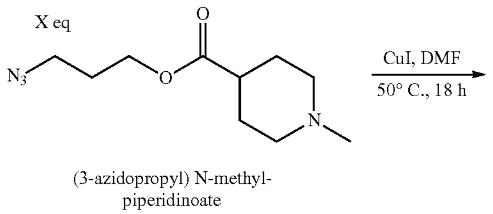

(3-azidopropyl) N-methyl-piperidinoate

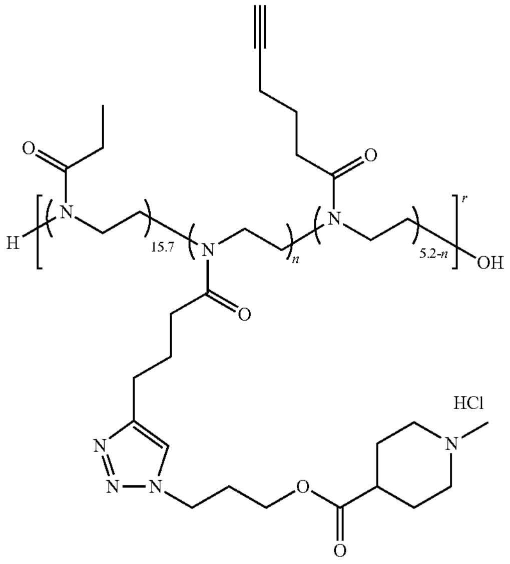

PEOZ—OH 2.3K np NMPCA

Example 26. Synthesis of PEOZ 2.6K 1.5p NMPCA, (where n=1.5)

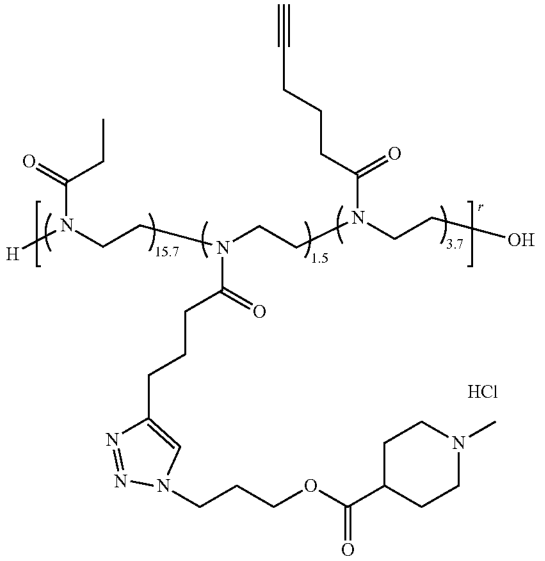

PEOZ—OH 2.3K 1.5p NMPCA

An oven-dried 25-mL round bottomed flask, equipped with a reflux condenser and an argon gas inlet, was charged with PEOZ-OH 2.3K 5.2p (1.00 g, 0.439 mmol, 1.0 eq, Mn 2279 Da) and (3-azidopropyl)-N-methylpiperidinoate (0.149 g, 0.658 mmol, 1.5 eq) followed by a stir bar and THE (10 mL) under argon atmosphere. After addition of CuI (0.0140 g, 0.073 mmol, 0.17 eq), the resulting mixture was stirred for 5 minutes at room temperature and then allowed to stir for 18 hours at 50° C. After cooling down to room temperature, the reaction mixture was quenched by adding 0.5 N aqueous HCl (5 mL) followed by stirring for 5 minutes. The mixture was passed through the Dowex® M4195 column and the column was eluted with a mixture of THE and 2 mN HCl (2:1). The resulting solution was concentrated using a rotary evaporator at 34° C. The residue was purified by silica-gel column chromatography using a Biotage (SNAP Ultra C18 cartridge), with a mixture of 2 mN HCl and methanol as an eluting solvent. After removing MeOH, the resulting aqueous solution was freeze-dried using a lyophilizer to provide the desired product (1.06 g, 90% yield) as a pale-yellow powder.

$^1H$ NMR (Varian, 500 MHz, 10 mg/mL DMSO-$d_6$, δ) analysis showed the standard backbone signals for PEOZ at 7.99 (br m, 1H, terminal NH), 3.34 (m, 4H, —$NCH_2CH_2N$— backbone), 3.16 (m, 2H, —N—$CH_2$), 2.32 and 2.27 (m, total area 2H, —C(═O)$CH_2CH_3$), and 0.95 (m, 3H, —C(═O)$CH_2CH_3$). Signals for the pendant group were present at 7.89 (br s, 1H, triazole ring, resulted by 'click' reaction), 4.37 (m, 2H, triazole N—$CH_2CH_2CH_2$—O—), 4.01 (m, 2H, triazole N—$CH_2CH_2CH_2$—O—), 2.66 and 2.57 (m, total area 6H, piperidyl), 2.14 (br s, 3H, pip-N—$CH_3$), 2.03 (m, 1H, pip-CH—C(O)O—), 1.99 (m, 2H, -piperidyl (CHH)N—$CH_3$), and 1.78 (m, 2H, triazole N—$CH_2CH_2CH_2$—O—). Additionally, two types of pendant pentynyl group peaks appear at 1.78 (m, 2H, backbone-$CH_2CH_2CH_2$-triazole ring, 'clicked') and 1.63 (m, 2H, backbone-$CH_2CH_2CH_2C$≡CH, intact). The number of pendant groups was determined from the $^1$H NMR analysis to be 1.5 by comparing the integrations of pendant group protons and polymer backbone protons, and the calculated molecular weight was 2673 Da.

Example 27. Synthesis of PEOZ 2.3K 3.3p NMPCA, (where n=3.3)

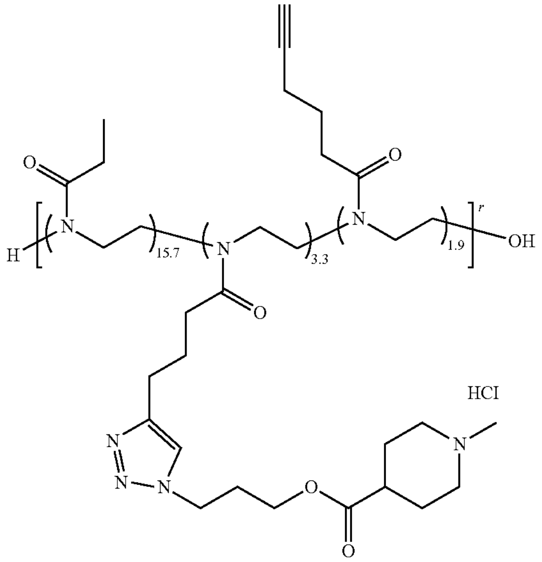

PEOZ—OH 2.3K 3.3p NMPCA

An oven-dried 25-mL round bottomed flask, equipped with a reflux condenser and an argon gas inlet, was charged with PEOZ-OH 2.3K 5.2p (0.995 g, 0.436 mmol, 1.0 eq, Mn 2279 Da) and (3-azidopropyl)-N-methylpiperidinoate (0.326 g, 1.440 mmol, 3.3 eq) followed by a stir bar and THE (10 mL) under argon atmosphere. After addition of CuI (0.0416 g, 0.218 mmol, 0.5 eq), the resulting mixture was stirred for 5 minutes at room temperature and then allowed to stir for 18 hours at 50 C. After cooling down to room temperature, the reaction mixture was quenched by adding 0.4 N aqueous HCl (5 mL) followed by stirring for 5 minutes. The mixture was passed through the Dowex® M4195 column and the column was eluted with a mixture of THE and 2 mN HCl (2:1). The resulting solution was concentrated using a rotary evaporator at 34° C. The residue was purified by silica-gel column chromatography using a Biotage (SNAP Ultra C18 cartridge), with a mixture of 2 mN HCl and methanol as an eluting solvent. After removing MeOH, the resulting aqueous solution was freeze-dried using a lyophilizer to provide the desired product (1.31 g, 95% yield) as a pale-yellow powder.

The attachment of (3-azidopropyl)-N-methylpiperidinoate was proved by 1H NMR (Varian, 500 MHz, 10 mg/mL DMSO-d6) that showed the peaks at 7.89 (br s, 1H, triazole ring, resulted by 'click' reaction), 4.37 (m, 2H, triazole N—CH2CH2CH2-O—), 4.01 (m, 2H, triazole N—CH2CH2CH2-O—), 2.58 (m, total area 6H, piperidyl), 2.13 (br s, 3H, pip-N—CH3), 2.03 (m, 1H, pip-CH—C(O)O—), 1.95 (m, 2H, -piperidyl (CHH)N—CH3), and 1.77 (m, 2H, triazole N—CH2CH2CH2-O—), besides the usual polymer backbone peaks. Additionally, two types of pendant pentynyl group peaks appear at 1.77 (m, 2H, backbone-CH2CH2CH2-triazole ring, 'clicked') and 1.63 (m, 2H, backbone-CH2CH2CH2C CH, intact). The number of pendant groups was determined from the 1H NMR analysis to be 3.3 by comparing the integrations of pendant group protons and polymer backbone protons, and the calculated molecular weight was 3146 Da.

Example 28. Synthesis of PEOZ 2.3K 4.5p NMPCA, (where n=4.5)

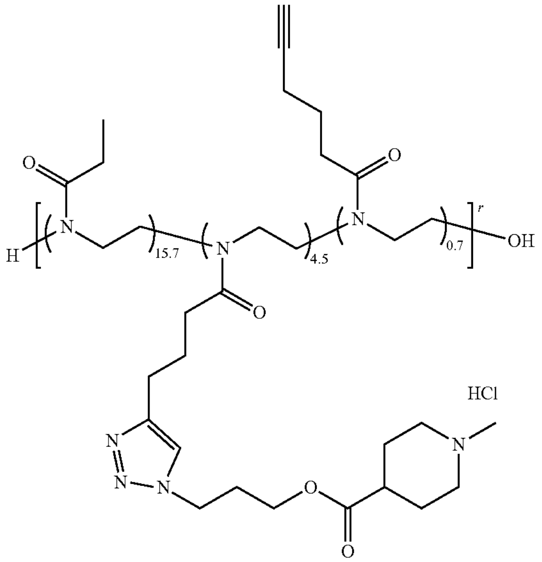

PEOZ—OH 2.3K 4.5p NMPCA

An oven-dried 25-mL round bottomed flask, equipped with a reflux condenser and an argon gas inlet, was charged with PEOZ-OH 2.3K 5.2p (0.995 g, 0.436 mmol, 1.0 eq, Mn 2279 Da) and (3-azidopropyl)-N-methylpiperidinoate (0.447 g, 1.96 mmol, 4.5 eq) followed by a stir bar and THE (10 mL) under argon atmosphere. After addition of CuI (0.0374 g, 0.196 mmol, 0.45 eq), the resulting mixture was stirred for 5 minutes at room temperature and then allowed to stir for 18 hours at 50° C. After cooling down to room temperature, the reaction mixture was quenched by adding 0.5 N aqueous HCl (5 mL) followed by stirring for 5 minutes. The mixture was passed through the Dowex® M4195 column and the column was eluted with a mixture of THE and 2 mN HCl (5:4). The resulting solution was concentrated using a rotary evaporator at 34° C. The residue was purified by silica-gel column chromatography using a Biotage (SNAP Ultra C18 cartridge), with a mixture of 2 mN HCl and methanol as an eluting solvent. After removing MeOH, the resulting aqueous solution was freeze-dried using a lyophilizer to provide the desired product (1.31 g, 95% yield) as a pale-yellow powder.

The attachment of (3-azidopropyl)-N-methylpiperidinoate was proved by $^1$H NMR (Varian, 500 MHz, 10 mg/mL DMSO-d6) that showed the peaks at 7.87 (br s, 1H, triazole ring, resulted by 'click' reaction), 4.37 (m, 2H, triazole N—$CH_2CH_2CH_2$—O—), 4.01 (m, 2H, triazole N-$CH_2CH_2CH_2$—O—), 2.63 and 2.58 (m, total area 6H, piperidyl), 2.12 (br s, 3H, pip-N—$CH_3$), 2.03 (m, 1H, pip-CH—C(O)O—), 1.98 (m, 2H, -piperidyl (CHH)N—$CH_3$), and 1.78 (m, 2H, triazole N—$CH_2CH_2CH_2$—O—), besides the usual polymer backbone peaks. Additionally, two types of pendant pentynyl group peaks appear at 1.78 (m, 2H, backbone-$CH_2CH_2CH_2$-triazole ring, 'clicked') and 1.64 (m, 2H, backbone-$CH_2CH_2CH_2C{\equiv}CH$, intact). The number of pendant groups was determined from the $^1H$ NMR analysis to be 4.5 by comparing the integrations of pendant group protons and polymer backbone protons, and the calculated molecular weight was 3461 Da.

Synthesis of PPOZ-OH 2.6K np Choline

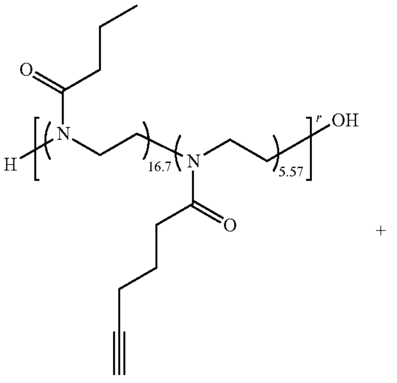

PPOZ—OH 2.6K 5.57p

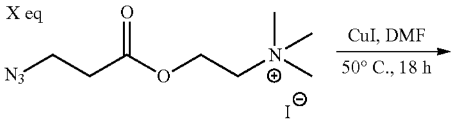

(Choline iodide)-3-azidopropionate

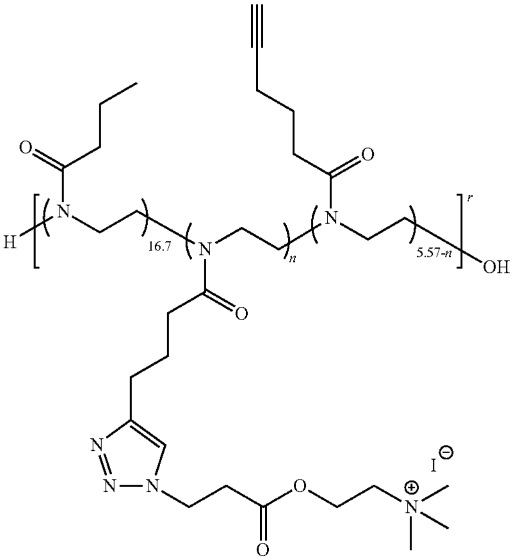

PPOZ—OH 2.6K np (Choline iodide)-3-propionate

Example 29. Synthesis of PPOZ 2.6K 1p (Choline Iodide)-3-propionate, (where n=1)

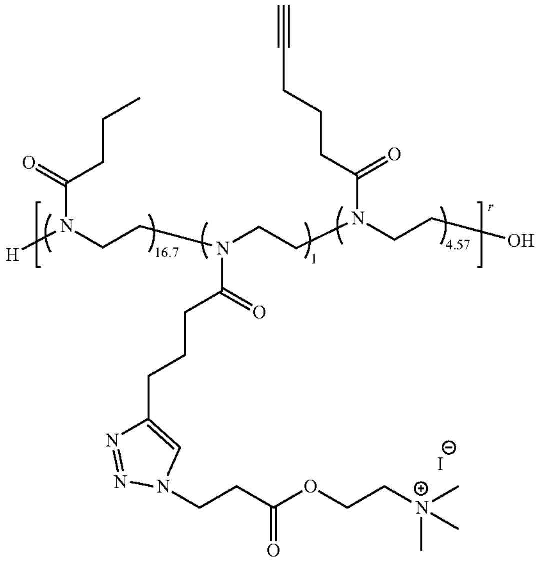

PPOZ—OH 2.6K 1p (Choline iodide)-3-propionate

An oven-dried 25-mL round bottomed flask, equipped with a reflux condenser and an argon gas inlet, was charged with PPOZ-OH 2.6K 5.6p (1.00 g, 0.377 mmol, 1.0 eq, Mn 2654 Da) and (choline iodide)-3-azidopropionate (0.153 g, 0.452 mmol, 1.2 eq, 97 wt %) followed by a stir bar and DMF (12 mL) under argon atmosphere. After addition of CuI (0.179 g, 0.942 mmol, 2.5 eq), the resulting mixture was stirred for 5 minutes at room temperature and then allowed to stir for 18 hours at 50° C. After cooling down to room temperature, the reaction mixture was quenched by adding 1.0 N aqueous HCl (3 mL) followed by stirring for 5 minutes. The mixture was passed through the Dowex® M4195 column and the column was eluted with a mixture of DMF and water (4:1). The resulting solution was concentrated using a rotary evaporator at 34° C. The residue was purified by silica-gel column chromatography using a Biotage (SNAP Ultra C18 cartridge), with a mixture of water and methanol as an eluting solvent. After removing MeOH, the resulting aqueous solution was freeze-dried using a lyophilizer to provide the desired product (0.98 g, 85% yield) as a pale-yellow powder.

$^1H$ NMR (Varian, 500 MHz, 10 mg/mL DMSO-$d_6$, δ) analysis showed the standard backbone signals for PPOZ at 7.99 (br m, 1H, terminal NH), 3.34 (m, 4H, —$NCH_2CH_2N$— backbone), 3.16 (m, 2H, —N—$CH_2$), 2.27 and 2.21 (m, total area 2H, —C(═O)$CH_2CH_2CH_3$), 1.48 (m, 2H, —C(═O)$CH_2CH_2CH_3$), and 0.84 (m, 3H, —C(═O)$CH_2CH_2CH_3$). Signals for the pendant group were present at 7.91 (br s, 1H, triazole ring, resulted by 'click' reaction), 4.55 (m, 2H, triazole N—$CH_2CH_2C$(═O)O—), 4.46 (m, 2H, —$OCH_2CH_2N^{\oplus}(CH_3)_3$), 3.64 (m, 2H, —$OCH_2CH_2N^{\oplus}(CH_3)_3$), 3.10 (s, 9H, —$N^{\oplus}(CH_3)_3$), and 2.57 (m, 2H, triazole N—$CH_2CH_2C$(═O)O—). Additionally, two types of pendant pentynyl group peaks appear at 1.78 (m, 2H, backbone-$CH_2CH_2CH_2$-triazole ring, 'clicked') and 1.64 (m, 2H, backbone-$CH_2CH_2CH_2C{\equiv}CH$, intact). The number of pendant groups was determined from the $^1H$ NMR analysis to be 1.0 by comparing the integrations of pendant group protons and polymer backbone protons, and the calculated molecular weight was 2982 Da.

Example 30. Synthesis of PPOZ 2.6K 3p (Choline Iodide)-3-propionate, (where n=3)

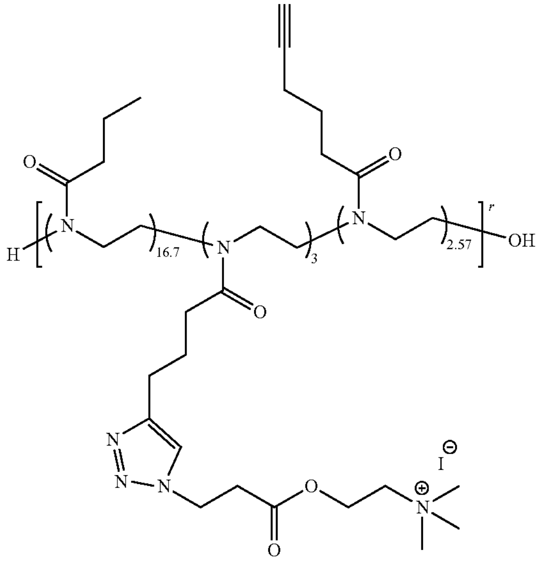

PPOZ—OH 2.6K 3p (Choline iodide)-3-propionate

An oven-dried 25-mL round bottomed flask, equipped with a reflux condenser and an argon gas inlet, was charged with PPOZ-OH 2.6K 5.6p (1.00 g, 0.377 mmol, 1.0 eq, Mn 2654 Da) and (choline iodide)-3-azidopropionate (0.402 g, 1.187 mmol, 3.15 eq, 97 wt %) followed by a stir bar and DMF (10 mL) under argon atmosphere. After addition of CuI (0.179 g, 0.942 mmol, 2.5 eq), the resulting mixture was stirred for 5 minutes at room temperature and then allowed to stir for 18 hours at 50° C. After cooling down to room temperature, the reaction mixture was quenched by adding 1.0 N aqueous HCl (3 mL) followed by stirring for 5 minutes. The mixture was passed through the Dowex® M4195 column and the column was eluted with a mixture of DMF and water (4:1). The resulting solution was concentrated using a rotary evaporator at 34° C. The residue was purified by silica-gel column chromatography using a Biotage (SNAP Ultra C18 cartridge), with a mixture of water and methanol as an eluting solvent. After removing MeOH, the resulting aqueous solution was freeze-dried using a lyophilizer to provide the desired product (1.14 g, 83% yield) as a pale-yellow powder.

The attachment of (choline iodide)-3-azidopropionate was proved by $^1$H NMR (Varian, 500 MHz, 10 mg/mL DMSO-$d_6$, δ) analysis that showed the peaks at 7.91 (br s, 1H, triazole ring, resulted by 'click' reaction), 4.55 (m, 2H, triazole N—$CH_2CH_2C$(=O)O—), 4.46 (m, 2H, —$OCH_2CH_2N^{\oplus}(CH_3)_3$), 3.66 (m, 2H, —$OCH_2CH_2N^{\oplus}(CH_3)_3$), 3.12 (s, 9H, —$N^{\oplus}(CH_3)_3$), and 2.57 (m, 2H, triazole N—$CH_2CH_2C$(=O)O—), besides the usual polymer backbone peaks. Additionally, two types of pendant pentynyl group peaks appear at 1.77 (m, 2H, backbone-$CH_2CH_2CH_2$— triazole ring, 'clicked') and 1.64 (m, 2H, backbone-$CH_2CH_2CH_2C{\equiv}CH$, intact). The number of pendant groups was determined from the $^1$H NMR analysis to be 2.98 by comparing the integrations of pendant group protons and polymer backbone protons, and the calculated molecular weight was 3638 Da.

Example 31. Synthesis of PPOZ 2.6K 4.7p (Choline Iodide)-3-propionate, (where n=4.7)

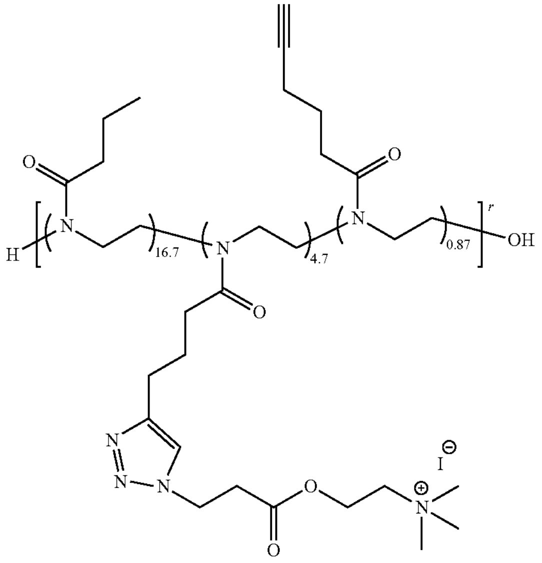

PPOZ—OH 2.6K 4.7p (Choline iodide)-3-propionate

An oven-dried 25-mL round bottomed flask, equipped with a reflux condenser and an argon gas inlet, was charged with PPOZ-OH 2.6K 5.6p (1.00 g, 0.377 mmol, 1.0 eq, Mn 2654 Da) and (choline iodide)-3-azidopropionate (0.701 g, 2.07 mmol, 5.5 eq, 97 wt %) followed by a stir bar and DMF (10 mL) under argon atmosphere. After addition of CuI (0.179 g, 0.942 mmol, 2.5 eq), the resulting mixture was stirred for 5 minutes at room temperature and then allowed to stir for 18 hours at 50° C. After cooling down to room temperature, the reaction mixture was quenched by adding 1.0 N aqueous HCl (2 mL) followed by stirring for 5 minutes. The mixture was passed through the Dowex® M4195 column and the column was eluted with a mixture of DMF and water (4:1). The resulting solution was concentrated using a rotary evaporator at 34° C. The residue was purified by silica-gel column chromatography using a Biotage (SNAP Ultra C18 cartridge), with a mixture of water and methanol as an eluting solvent. After removing MeOH, the resulting aqueous solution was freeze-dried using a lyophilizer to provide the desired product (1.27 g, 80% yield) as a pale-yellow powder.

The attachment of (choline iodide)-3-azidopropionate was proved by $^1$H NMR (Varian, 500 MHz, 10 mg/mL DMSO-$d_6$, δ) analysis that showed the peaks at 7.91 (br s, 1H, triazole ring, resulted by 'click' reaction), 4.56 (m, 2H, triazole N—$CH_2CH_2C$(=O)O—), 4.45 (m, 2H, —$OCH_2CH_2N^{\oplus}(CH_3)_3$), 3.69 (m, 2H, —$OCH_2CH_2N^{\oplus}(CH_3)_3$), 3.12 (s, 9H, —$N^{\oplus}(CH_3)_3$), and 2.57 (m, 2H, triazole N—$CH_2CH_2C$(=O)O—), besides the usual polymer backbone peaks. Additionally, two types of pendant pentynyl group peaks appear at 1.76 (m, 2H, backbone-$CH_2CH_2CH_2$— triazole ring, 'clicked') and 1.64 (m, 2H, backbone-$CH_2CH_2CH_2C{\equiv}CH$, intact). The number of pendant groups was determined from the $^1$H NMR analysis to be 4.7 by comparing the integrations of pendant group protons and polymer backbone protons, and the calculated molecular weight was 4200 Da.

Synthesis of PPOZ-OH 2.6K np NMPCA

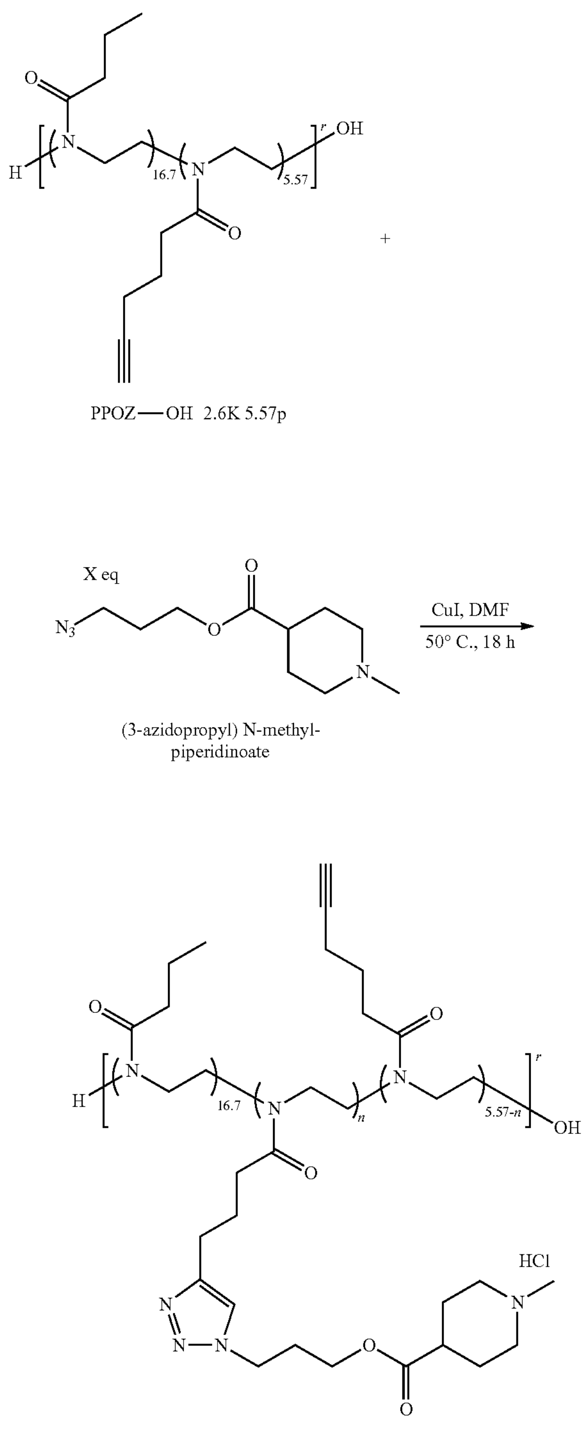

PPOZ—OH 2.6K 5.57p

+

(3-azidopropyl) N-methyl-piperidinoate

PPOZ—OH 2.6K np NMPCA

Example 32. Synthesis of PPOZ 2.6K 1p NMPCA, (where n=1)

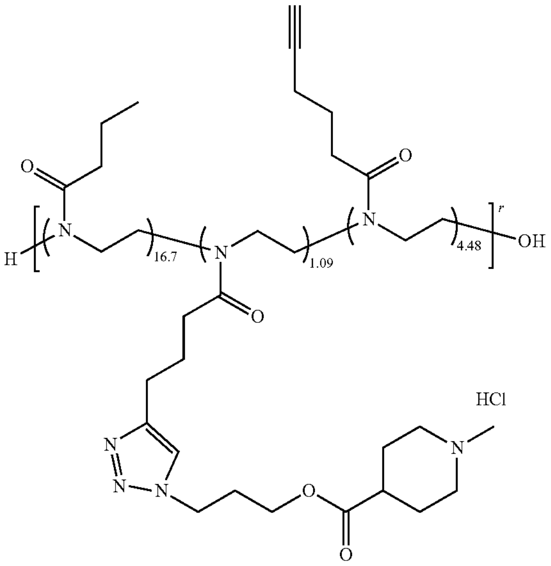

PPOZ—OH 2.6K 1.09p NMPCA

An oven-dried 25-mL round bottomed flask, equipped with a reflux condenser and an argon gas inlet, was charged with PPOZ-OH 2.6K 5.6p (1.00 g, 0.377 mmol, 1.0 eq, Mn 2654 Da) and (3-azidopropyl)-N-methylpiperidinoate (0.102 g, 0.452 mmol, 1.2 eq) followed by a stir bar and THF (10 mL) under argon atmosphere. After addition of CuI (0.0359 g, 0.188 mmol, 0.5 eq), the resulting mixture was stirred for 5 minutes at room temperature and then allowed to stir for 18 hours at 50° C. After cooling down to room temperature, the reaction mixture was quenched by adding 0.5 N aqueous HCl (3 mL) followed by stirring for 5 minutes. The mixture was passed through the Dowex® M4195 column and the column was eluted with a mixture of THF and 2 mN HCl (3:1). The resulting solution was concentrated using a rotary evaporator at 34° C. The residue was purified by silica-gel column chromatography using a Biotage (SNAP Ultra C18 cartridge), with a mixture of 2 mN HCl and methanol as an eluting solvent. After removing MeOH, the resulting aqueous solution was freeze-dried using a lyophilizer to provide the desired product (1.00 g, 91% yield) as a pale-yellow powder.

$^1$H NMR (Varian, 500 MHz, 10 mg/mL DMSO-$d_6$, δ) analysis showed the standard backbone signals for PPOZ at 7.91 (br m, 1H, terminal NH), 3.34 (m, 4H, —$NCH_2CH_2N$— backbone), 3.16 (m, 2H, —N—$CH_2$), 2.27 and 2.21 (m, total area 2H, —C(═O)$CH_2CH_2CH_3$), 1.48 (m, 2H, —C(═O)$CH_2CH_2CH_3$), and 0.84 (m, 3H, —C(═O)$CH_2CH_2CH_3$). Signals for the pendant group were present at 7.85 (br s, 1H, triazole ring, resulted by 'click' reaction), 4.37 (m, 2H, triazole N—$CH_2CH_2CH_2$—O—), 4.01 (m, 2H, triazole N—$CH_2CH_2CH_2$—O—), 2.58 (m, total area 6H, piperidyl), 2.15 (br s, 3H, pip-N—$CH_3$), 2.01 (m, 2H, -piperidyl (CHH)N—$CH_3$), 1.95 (m, 1H, pip-CH—C(O)O—), and 1.64 (m, 2H, triazole N—$CH_2CH_2CH_2$—O—). Additionally, two types of pendant pentynyl group peaks appear at 1.77 (m, 2H, backbone-$CH_2CH_2CH_2$-triazole ring, 'clicked') and 1.63 (m, 2H, backbone-$CH_2CH_2CH_2C{\equiv}CH$, intact). The number of pendant groups was determined from the $^1H$ NMR analysis to be 1.09 by comparing the integrations of pendant group protons and polymer backbone protons, and the calculated molecular weight was 2940 Da.

Example 33. Synthesis of PPOZ 2.6K 3p NMPCA, (where n=3)

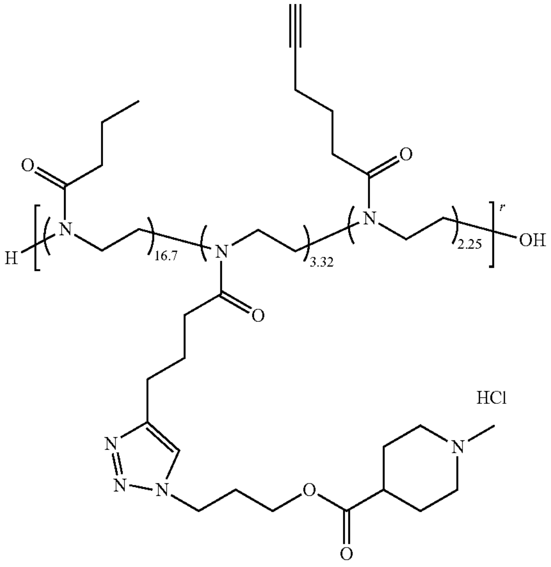

PPOZ—OH 2.6K 3.32p NMPCA

An oven-dried 25-mL round bottomed flask, equipped with a reflux condenser and an argon gas inlet, was charged with PPOZ-OH 2.6K 5.6p (1.00 g, 0.377 mmol, 1.0 eq, Mn 2654 Da) and (3-azidopropyl)-N-methylpiperidinoate (0.281 g, 1.243 mmol, 3.3 eq) followed by a stir bar and THE (10 mL) under argon atmosphere. After addition of CuI (0.0359 g, 0.188 mmol, 0.5 eq), the resulting mixture was stirred for 5 minutes at room temperature and then allowed to stir for 18 hours at 50° C. After cooling down to room temperature, the reaction mixture was quenched by adding 0.5 N aqueous HCl (3 mL) followed by stirring for 5 minutes. The mixture was passed through the Dowex® M4195 column and the column was eluted with a mixture of THE and 2 mN HCl (4:1). The resulting solution was concentrated using a rotary evaporator at 34° C. The residue was purified by silica-gel column chromatography using a Biotage (SNAP Ultra C18 cartridge), with a mixture of 2 mN HCl and methanol as an eluting solvent. After removing MeOH, the resulting aqueous solution was freeze-dried using a lyophilizer to provide the desired product (1.12 g, 86% yield) as a pale-yellow powder.

The attachment of (3-azidopropyl)-N-methylpiperidinoate was proved by $^1H$ NMR (Varian, 500 MHz, 10 mg/mL DMSO-d6) that showed the peaks at 7.86 (br s, 1H, triazole ring, resulted by 'click' reaction), 4.37 (m, 2H, triazole N—$CH_2CH_2CH_2$—O—), 4.01 (m, 2H, triazole N—$CH_2CH_2CH_2$—O—), 2.58 (m, total area 6H, piperidyl), 2.13 (br s, 3H, pip-N—$CH_3$), 2.01 (m, 2H, -piperidyl (CHH)N—$CH_3$), 1.95 (m, 1H, pip-CH—C(O)O—), and 1.77 (m, 2H, triazole N—$CH_2CH_2CH_2$—O—), besides the usual polymer backbone peaks. Additionally, two types of pendant pentynyl group peaks appear at 1.77 (m, 2H, backbone-$CH_2CH_2CH_2$-triazole ring, 'clicked') and 1.64 (m, 2H, backbone-$CH_2CH_2CH_2C{\equiv}CH$, intact). The number of pendant groups was determined from the $^1H$ NMR analysis to be 3.32 by comparing the integrations of pendant group protons and polymer backbone protons, and the calculated molecular weight was 3526 Da.

Example 34. Synthesis of PPOZ 2.6K 5p NMPCA, (where n=5)

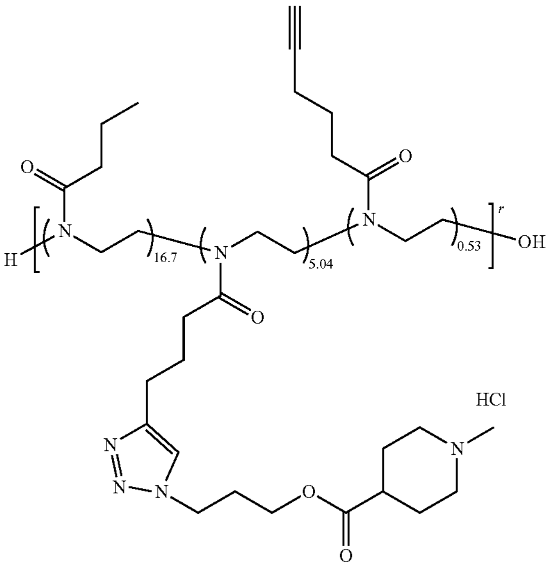

PPOZ—OH 2.6K 5.04p NMPCA

An oven-dried 25-mL round bottomed flask, equipped with a reflux condenser and an argon gas inlet, was charged with PPOZ-OH 2.6K 5.6p (1.00 g, 0.377 mmol, 1.0 eq, Mn 2654 Da) and (3-azidopropyl)-N-methylpiperidinoate (0.40 g, 1.768 mmol, 4.7 eq) followed by a stir bar and THE (10 mL) under argon atmosphere. After addition of CuI (0.0359 g, 0.188 mmol, 0.5 eq), the resulting mixture was stirred for 5 minutes at room temperature and then allowed to stir for 18 hours at 50° C. After cooling down to room temperature, the reaction mixture was quenched by adding 0.5 N aqueous HCl (6 mL) followed by stirring for 5 minutes. The mixture was passed through the Dowex® M4195 column and the column was eluted with a mixture of THE and 2 mN HCl (1:1). The resulting solution was concentrated using a rotary evaporator at 34° C. The residue was purified by silica-gel column chromatography using a Biotage (SNAP Ultra C18 cartridge), with a mixture of 2 mN HCl and methanol as an eluting solvent. After removing MeOH, the resulting aqueous solution was freeze-dried using a lyophilizer to provide the desired product (1.26 g, 84% yield) as a pale-yellow powder.

The attachment of (3-azidopropyl)-N-methylpiperidinoate was proved by $^1H$ NMR (Varian, 500 MHz, 10 mg/mL DMSO-d6) that showed the peaks at 7.86 (br s, 1H, triazole ring, resulted by 'click' reaction), 4.37 (m, 2H, triazole N—$CH_2CH_2CH_2$—O—), 4.01 (m, 2H, triazole N—$CH_2CH_2CH_2$—O—), 2.59 (m, total area 6H, piperidyl), 2.13 (br s, 3H, pip-N—$CH_3$), 1.98 (m, 2H, -piperidyl (CHH)N—$CH_3$), 1.98 (m, 1H, pip-CH—C(O)O—), and 1.77 (m, 2H, triazole N—$CH_2CH_2CH_2$—O—), besides the usual polymer backbone peaks. Additionally, two types of pendant pentynyl group peaks appear at 1.77 (m, 2H, backbone-$CH_2CH_2CH_2$-triazole ring, 'clicked') and 1.64 (m, 2H, backbone-$CH_2CH_2CH_2C{\equiv}CH$, intact). The number of pendant groups was determined from the $^1H$ NMR analysis to be 5.04 by comparing the integrations of pendant group protons and polymer backbone protons, and the calculated molecular weight was 3978 Da.

Example 35. Synthesis of PPOZ 2.6K 1p Spermine

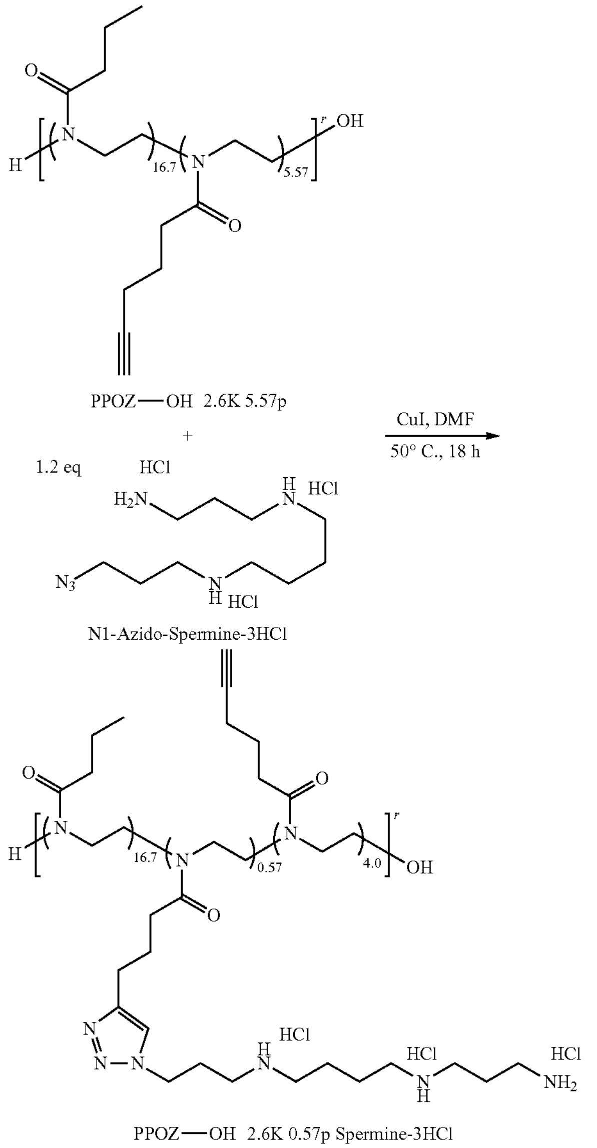

PPOZ—OH 2.6K 5.57p

+

N1-Azido-Spermine-3HCl

PPOZ—OH 2.6K 0.57p Spermine-3HCl

An oven-dried 25-mL round bottomed flask, equipped with a reflux condenser and an argon gas inlet, was charged with PPOZ-OH 2.6K 5.6p (0.20 g, 0.075 mmol, 1.0 eq, Mn 2654 Da) and N1-azido-spermine-3HCl (0.0364 g, 0.106 mmol, 1.4 eq) followed by a stir bar and DMF (2 mL) under argon atmosphere. After addition of TEA (63.1 uL, 0.452 mmol, 6 eq) and CuI (0.0359 g, 0.188 mmol, 0.5 eq), the resulting mixture was stirred for 5 minutes at room temperature and then allowed to stir for 18 hours at 50° C. After cooling down to room temperature, the reaction mixture was quenched by adding 1.0 N aqueous HCl (2 mL) followed by stirring for 5 minutes. The mixture was passed through the Dowex® M4195 column and the column was eluted with a mixture of DMF and 2 mN HCl (1:1). The resulting solution was concentrated using a rotary evaporator at 34° C. The residue was purified by silica-gel column chromatography using a Biotage (SNAP Ultra C18 cartridge), with a mixture of 2 mN HCl and methanol as an eluting solvent. After removing MeOH, the resulting aqueous solution was freeze-dried using a lyophilizer to provide the desired product (0.15 g, 70% yield) as a pale-yellow powder.

$^1H$ NMR (Varian, 500 MHz, 10 mg/mL DMSO-$d_6$, δ) analysis showed the standard backbone signals for PPOZ at 7.94 (br m, 1H, terminal NH), 3.34 (m, 4H, —$NCH_2CH_2N$— backbone), 3.17 (m, 2H, —N—$CH_2$), 2.27 and 2.21 (m, total area 2H, —C(=O)$CH_2CH_2CH_3$), 1.48 (m, 2H, —C(=O)$CH_2CH_2CH_3$), and 0.84 (m, 3H, —C(=O)$CH_2CH_2CH_3$). Signals for the pendant group were present at 7.80 (br s, 1H, triazole ring, resulted by 'click' reaction), 4.42 (m, 2H, triazole N—$CH_2CH_2CH_2$—NH—), 2.95 (m, 2H, spermine —$CH_2NH_2$), 2.88 (m, 8H, —$CH_2NHCH_2$—), and 1.64 (m, 2H, triazole N—$CH_2CH_2CH_2$—NH—). Additionally, two types of pendant pentynyl group peaks appear at 1.78 (m, 2H, backbone-$CH_2CH_2CH_2$-triazole ring, 'clicked') and 1.64 (m, 2H, backbone-$CH_2CH_2CH_2C{\equiv}CH$, intact). The number of pendant groups was determined from the $^1H$ NMR analysis to be 0.57 by comparing the integrations of pendant group protons and polymer backbone protons, and the calculated molecular weight was 2487 Da.

Example 36. Gel Shift Assay for pDNA/PEOZ Cholamide 1K and 2K Polyplexes with Different Number of Charges on Polymer Backbone A gel shift assay was performed to assess the binding ability of two PEOZ cationic polymers with the choline charged groups to form complexes with plasmid DNA (pDNA). They were PEOZ 1K Cholamide (Example 7) and PEOZ 2K 5.8p Cholamide (Example 9). Various ratios of polymer to pDNA (w/w) were prepared and tested on a 1% agarose gel (E-Gel Agarose gel, Invitrogen).

The plasmid DNA (pDNA) used was the gWiz Green Fluorescent Protein encoded with the GFP gene (Aldevron). The plasmid has 5757 bps and is supplied at 5.05 μg/μL in water. The plasmid was diluted with 10 mM citrate buffer, pH 4, to prepare a solution at 0.1 μg/μL. A stock solution containing PEOZ cholamide polymers was prepared in Ethanol (Supelco, EX0276-1) to 31.53 mg/mL for PEOZ 1K Cholamide 1K and 36.75 mg/mL for PEOZ 2K Cholamide. To evaluate the amount of PEOZ polymers that would completely bind to pDNA and retard the DNA band mobility, 1 μg of pDNA was mixed with various μg concentrations of PEOZ Cholamide polymers and allowed to form a complex at room temperature for 10-15 minutes. The complex mixture was diluted in Ethanol to 5 ng/μL pDNA and 20 μL was loaded onto an agarose 1% E-gel EX with SYBR Gold II (Invitrogen) and run for 10 min. The gel was analyzed on a gel imaging system (E-Gel Power Snap Electrophoresis System, Invitrogen) to detect the shift of the pDNA band.

Figure 3A:
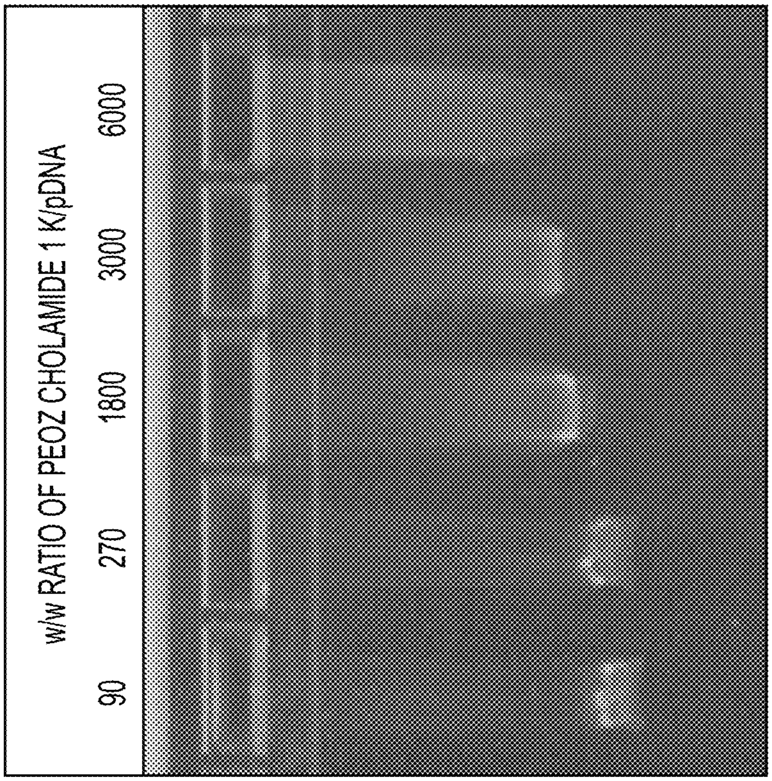
FIGS. 3A-3B show payload binding to cationic POZ at increasing polymer concentration in accordance with embodiments of the present disclosure.
Figure 3B:
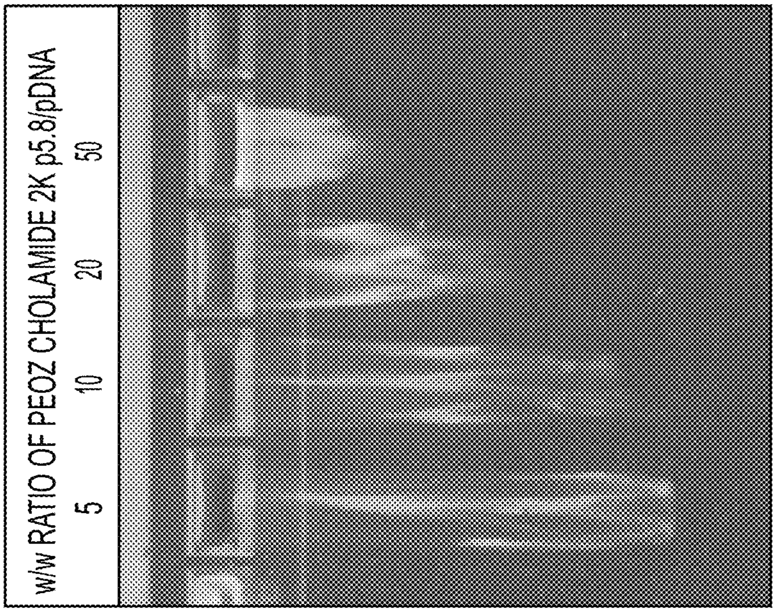

FIG. 3A shows the pDNA binding to PEOZ cholamide 1K with increasing polymer concentrations from 90 to 6000 μg and FIG. 3B shows the pDNA binding to PEOZ cholamide 2K with increasing polymer concentrations from 5 to 50 μg. The gel shifts compare PEOZ cholamide 1K with one cationic charge with the PEOZ Cholamide 2K with approximately 5.8 cationic charges. When the number of cationic charges on the polymer backbone are increased, less amount of PEOZ polymer is required to bind a fixed ratio of DNA.

Example 37. Gel Shift Assay for pDNA/PEOZ Polyplexes with Same Number of Charges on Polymer Backbone but Different Types of Attachment Chemistries Gel shift assay was performed to assess the binding ability of PEOZ 2.3K 1.4p (Choline-Iodide)-2-proprionate (Example 22) and PEOZ-OH 2.3K 1p (Choline-Iodide)-3-proprionate (Example 23) to form complexes with pDNA. Various ratios of polymer to pDNA (w/w) were prepared and analyzed on the agarose gel (E-Gel EX Agarose gel, Invitrogen).

The plasmid DNA (pDNA) used was the gWiz Green Fluorescent Protein encoded with the GFP gene (Aldevron). The plasmid has 5757 bps and is supplied at 5.05 μg/μL in water. The plasmid was diluted with 10 mM citrate buffer, pH 4, to prepare a solution of 0.1 μg/μL. A stock solution containing ionizable PEOZ cholamide polymers was prepared in molecular biology grade quality water (Corning, 46-000-CM) to various concentrations from 10 to 25 μg/μL.

Figure 4B:
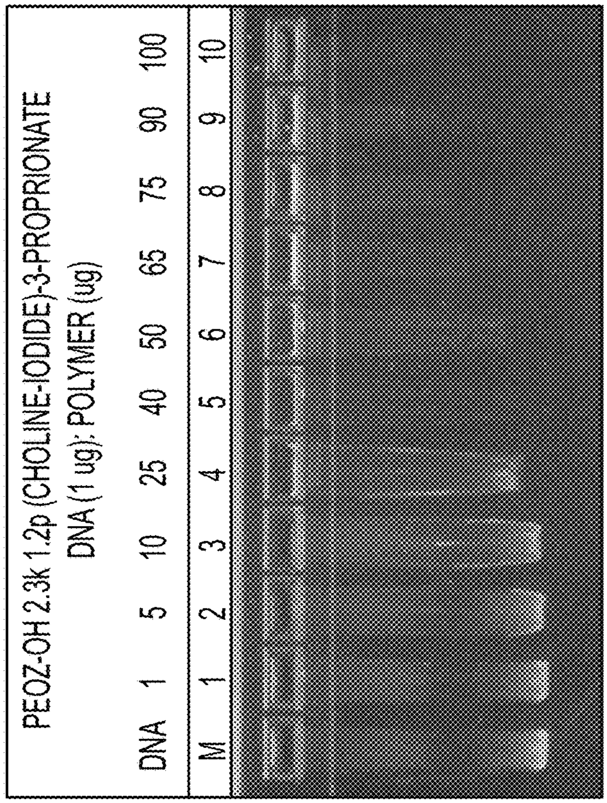
FIGS. 4A-4B shows payload binding to cationic POZ with different linkers and at increasing polymer concentration in accordance with embodiments of the present disclosure.
Figure 4A:
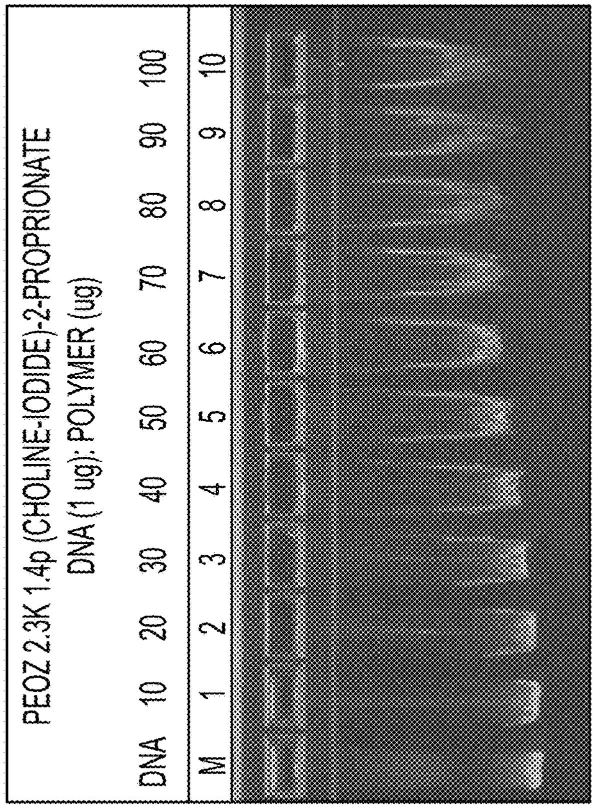

To evaluate the amount of PEOZ polymer that would completely bind to pDNA and retard the DNA band mobility, 1 μg of pDNA was mixed with various concentrations of PEOZ polymers and allowed to form a complex at room temperature for 10-15 minutes. The complex mixture diluted in TE buffer pH 7.4 to 5 ng/μL pDNA and 20 μL was loaded onto a 1% E-gel EX with SYBR Gold II (Invitrogen) and run for 10 min. The gel was analyzed on a gel imaging system (E-Gel Power Snap Electrophoresis System, Invitrogen) to detect the shift of the pDNA band. FIG. 4A shows pDNA binding to the PEOZ polymer with the 2-propionate linker and FIG. 4B shows pDNA binding to the PEOZ polymer with the 3-propionate linker, with increasing polymer concentration from 10 to 100 μg. The first lane contained a pDNA control. Comparison of the two PEOZ 2.3K polymers with a single cationic charge in the figures, show that the 3-propionate linker binds to DNA at lower concentration than the one with the 2-propionate linker. The 3-propionate linker has an extra carbon in the linear chain between the triazole ring and the choline charge and is not hindered.

Example 38. Gel Shift Assay for pDNA Polyplexes Made with PEOZ and PPOZ N-Methylpiperidinoate (NMPCA) Compounds Gel shift assay was performed to assess the binding ability of PEOZ 2.3K 1.5p NMPCA (Example 26), PEOZ 2.3K 4.5p NMPCA (Example 28), PEOZ 2.6K 9p NMPCA (Example 19) and PPOZ 2.6K 5p NMPCA (Example 34) with pDNA. Various ratios of polymer to pDNA (w/w) were prepared and analyzed on the agarose gel (E-Gel EX Agarose gel, Invitrogen). The plasmid DNA (pDNA) used was the gWiz Green Fluorescent Protein encoded with the GFP gene (Aldevron). The plasmid has 5757 bps and is supplied at 5.05 μg/μL in water. The plasmid was diluted with 10 mM citrate buffer, pH 4, to prepare a solution of 0.1 μg/μL. A stock solution containing either PEOZ or PPOZ polymer with NMPCA was prepared in molecular biology grade quality water (Corning, 46-000-CM) to various concentrations from 10 to 25 μg/μL. To evaluate the amount of PEOZ or PPOZ polymer that would completely bind to pDNA and retard the DNA band mobility, 1 μg of pDNA was mixed with various concentrations of PEOZ/PPOZ NMPCA polymers and allowed to form a complex at room temperature for 10-15 minutes.

Figure 5A:
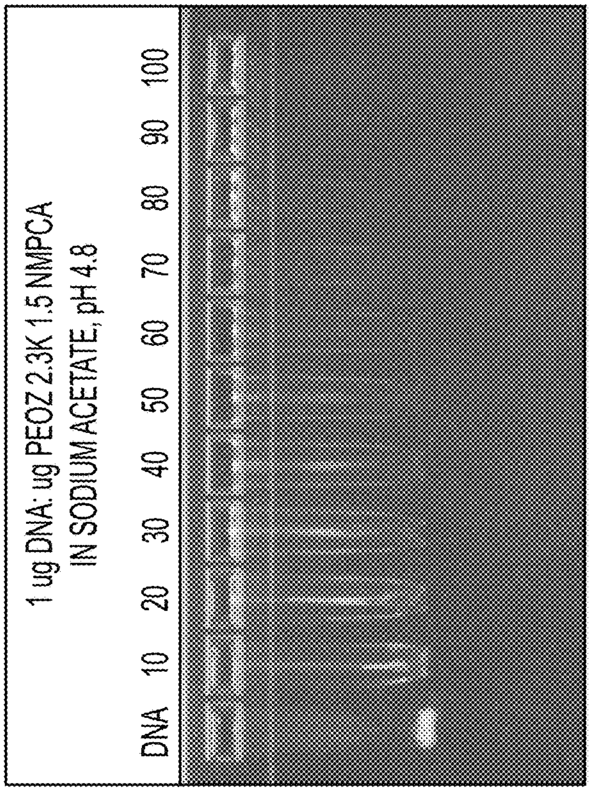
FIGS. 5A-5B shows payload binding to cationic POZ at increasing polymer concentration in accordance with embodiments of the present disclosure.
Figure 5B:
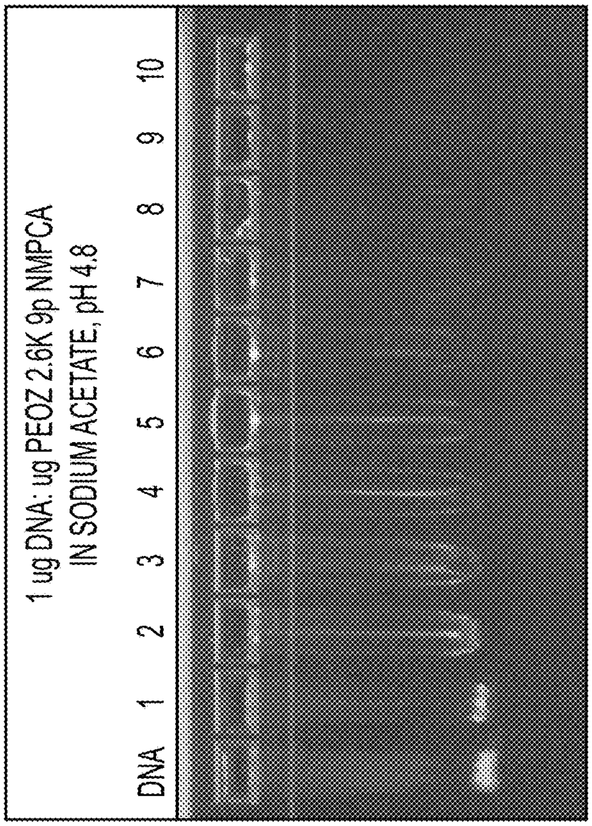
Figure 6A:
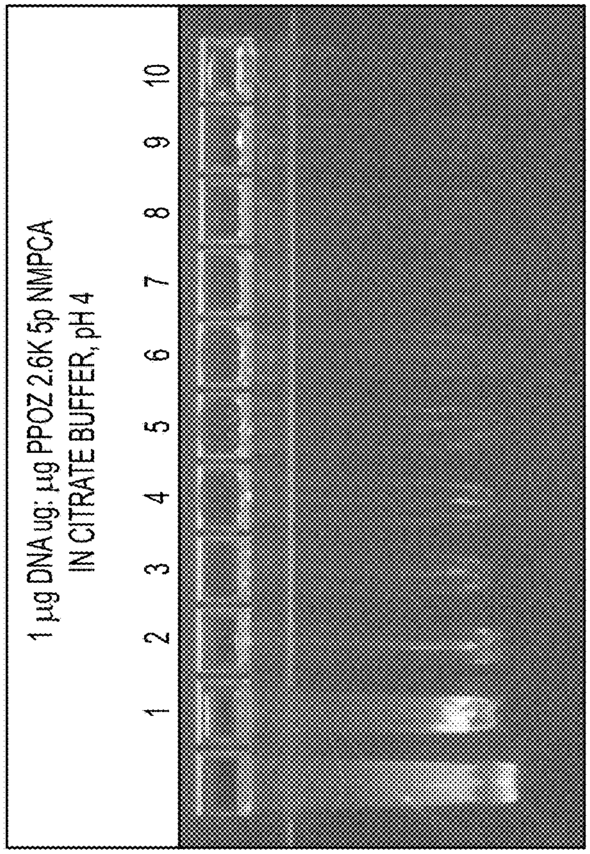
FIGS. 6A-6B shows payload binding to cationic POZ with different linkers and at increasing polymer concentration in accordance with embodiments of the present disclosure.
Figure 6B:
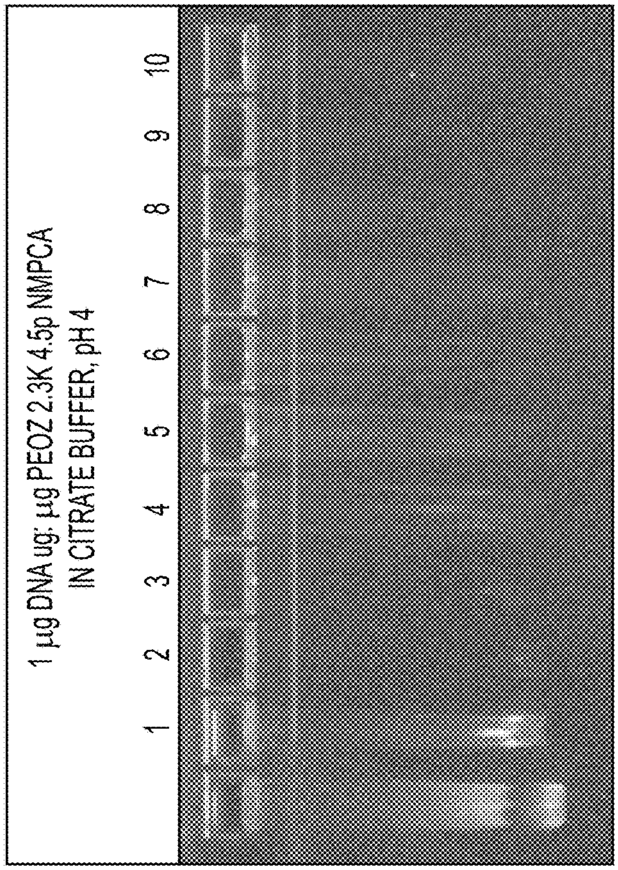

The complex mixture was diluted in 25 mM Sodium Acetate buffer, pH 4.8 (FIGS. 5A-5B) or 10 mM citrate buffer, pH 4.0 (FIGS. 6A-6B) to 5 ng/μL pDNA and 20 μL was loaded onto a 1% E-gel EX with SYBR Gold II (Invitrogen) and run for 10 min. The gel was analyzed on a gel imaging system (E-Gel Power Snap Electrophoresis System, Invitrogen) to detect the shift of the pDNA band.

As the number of charges increase from 1 to 4.5 and to 9, the μg amount of PEOZ polymer required to bind 1 μg of DNA decreases.

Example 39. Preparation of Lipid Nanoparticles Containing pDNA and PEOZ-cholamide Polymers with Different Charges—By Hand Mixing Method The plasmid DNA (pDNA) used in this example was the pWiz GFP plasmid DNA (Aldevron). The plasmid has 5757 bps and is supplied at 5.05 μg/μL in water was diluted with 10 mM citrate buffer, pH 4.5, to prepare a solution of 0.1 mg/mL concentration. Individual lipid stock solutions were made for PEOZ Cholamide 1K (Example 7), PEOZ DMAEA 1K (Example 6), and PEOZ-OH 2K 5.8p Cholamide (Example 9) by dissolving each in Ethanol. Each Lipid stock was mixed with 1,2-distearoyl-sn-glycero-3-phosphocholine (DSPC, Bachem 4005619)/Cholesterol (VWR 0433) and PEOZ 2K DMA (Ser-24) stock solutions in Ethanol at molar ratios of 50/10/38.5/1.5 for each PEOZ polymer in ethanol (EMD Millipore EX0276-4) at various lipid mix stock concentrations (organic lipid mix solution) for various LNP N/P ratios (Table 1) The lipid mix stock solutions were mixed with the pDNA (aqueous mixture) at a 3 parts aqueous to 1 part organic while slowly mixing on a vortex at a low speed. The prepared lipid nanoparticle solutions were diluted in citrate buffer pH 4, PBS buffer pH 7.5, or a 20 mM HEPES/5% Dextrose to reduce the ethanol content in the formulations to less than 6%.

The size of the formulated PEOZ LNPs was measured using dynamic light scattering (DLS) (Zetasizer Ultra, Malvern Panalytical). The particle size and polydispersity of the PEOZ LNP formulations have measurements values typical of LNP complexes (Table 1).

TABLE 1

| POZ | Molar Ratio | | | | | | Particle | Poly- | Zeta |
|---|---|---|---|---|---|---|---|---|---|
| cationic Polymer | POZ cationic | 1,2 DSPC | Cholesterol | POZ DMA | N/P ratio | Buffer | Size (nm) | dispersity (PDI) | Potential (mV) |
| PEOZ Cholamide 1K | 50 | 10 | 38.5 | 1.5 | 6:1 | Citrate buffer | 87.66 | 0.184 | −12.46 |

TABLE 1-continued

| POZ cationic Polymer | Molar Ratio POZ cationic | 1,2 DSPC | Cholesterol | POZ DMA | N/P ratio | Buffer | Particle Size (nm) | Poly-dispersity (PDI) | Zeta Potential (mV) |
|---|---|---|---|---|---|---|---|---|---|
| PEOZ DMAEA 1K | 50 | 10 | 38.5 | 1.5 | 6:1 | Citrate buffer | 78.59 | 0.215 | −8.715 |
| PEOZ Cholamide 2K 5.8 p | 50 | 10 | 38.5 | 1.5 | 2.4 | Citrate buffer | 155.5 | 0.176 | −12.2 |
| | | | | | 4.9 | | 224.2 | 0.317 | −5.5 |
| | | | | | 9.7 | | 296.3 | 0.510 | −1.5 |
| | | | | | 28.4 | | 402.0 | 0.345 | 4.7 |
| | | | | | 36.7 | | 357.0 | 0.336 | 6.3 |
| PEOZ-OH 2.3K 1 p (Choline-Iodide)-3-proprionate | 50 | 10 | 38.5 | 1.5 | 8.94 | Citrate buffer | 92.67 | 0.3352 | |
| | | | | | | PBS | 83.68 | 0.171 | −6.5 |
| | | | | | | HEPES/5% Dextrose | 90.75 | 0.3365 | −8.96 |

Example 40. Preparation of Lipid Nanoparticles Containing pDNA and PEOZ-NMP Polymers by Microfluidics Method The plasmid DNA (pDNA) used in this example was the phMGFP plasmid DNA (phMGFP-Promega E6421). The plasmid has 4707 bps and is supplied at 1 µg/µL in 10 mM Tris-HCl (pH 7.4), 1 mM EDTA and was diluted with 10 mM citrate buffer, pH 4.5, to prepare an aqueous solution of 0.1 mg/mL concentration.

Organic Lipid mix stock solutions of PEOZ 2.6K 9p NMPCA (Example 19) and PEOZ 2.6K 9p NMPOH (Example 18) (organic solutions were prepared at molar ratio of 50/10/38.5/1.5 for each PEOZ/1,2-distearoyl-sn-glycero-3-phosphocholine (DSPC, Bachem 4005619)/cholesterol (VWR 0433) and PEOZ 2K DMA lipid mixture in ethanol (EMD Millipore EX0276-4). A microfluidic mixing system equipped with a cartridge (Nunchuck, Unchained Labs) was used to mix the pDNA aqueous solutions and the lipid organic solutions at a ratio of 3 parts aqueous to 1 part organic for N/P ratios of 15:1 and 14.7 for the two polymers. Varying flow rates (TFR) of 15, 20, 25 and 30 mL/min were selected and 0.25 mL fractions of LNP mixture were collected. Each fraction was diluted in 10 mM citrate buffer to reduce the EtOH percent from 25% to less than 6%. The size, polydispersity, and zeta potential of the formulated LNPs was measured using dynamic light scattering (DLS) (Zetasizer Ultra, Malvern Panalytical). The particle sizes of the LNPs were less than 100 nm and the polydispersity values were closer to 0.2, values that are typically seen when microfluidic devices are used. (Table 2).

TABLE 2

| POZ cationic Polymer | Molar Ratio POZ cationic | 1,2 DSPC | Cholesterol | PEOZ DMA | N/P ratio | TFR (mL/min) | Particle Size (nm) | Poly-dispersity (PDI) | Zeta Potential (mV) |
|---|---|---|---|---|---|---|---|---|---|
| PEOZ 2.6K 9 p NMPCA | 50 | 10 | 38.5 | 1.5 | 15:1 | 30 | 67.2 | 0.24 | −9.20 |
| | | | | | | 25 | 59.8 | 0.21 | −5.73 |
| | | | | | | 20 | 51.4 | 0.24 | −1.94 |
| | | | | | | 15 | 56.0 | 0.19 | −7.87 |
| PEOZ 2.6K 9 p NMPOH | 50 | 10 | 38.5 | 1.5 | 14.7:1 | 30 | 54.5 | 0.22 | −2.57 |
| | | | | | | 25 | 47.4 | 0.11 | −3.87 |
| | | | | | | 20 | 81.7 | 0.29 | −2.72 |
| | | | | | | 15 | 56.6 | 0.27 | 0.14 |

Example 41. In-Vitro Transfection of LNP Formulation Made from PEOZ Cationic Polymers and Containing a DNA GFP Payload, Using HEK293 Cells Human Embryonic Kidney (HEK) 293 cells (ATCC) were seeded in a 96 well cell treated plate (Corning) at a density of 5,000-10,000 cells/well in 200 µL of DMEM media (Corning) with 10% FBS (Corning). The HEK293 plate was incubated at 37° C./5% $CO_2$ overnight to a confluency of ~60-70%. Media was removed from each well, cells were washed with DPBS and replaced with a selected screening buffer. Formulation dose amounts of LNP formulations were calculated based on pDNA GFP concentration and were added to the plate wells at various doses. The plate was returned to the incubator to allow for cellular uptake of the formulations. After 3-4 hours, 120 uL DMEM with 10% FBS was added to the transfected wells and the plate was returned to incubator for 24-72 hours. Cells were analyzed on an EVOS-M7000 microscope (Invitrogen) at 4× and 20× magnification for cellular vitality and expression of Green Fluorescent Protein (GFP) signal.

LNP formulations with cationic polymers PEOZ 2.3K 1.2p (Choline-Iodide)-3-proprionate (Example 23), PEOZ 2.3K 1.5p NMPCA (Example 26), and PEOZ 2.6K 9p NMPCA (Example 19) were prepared as described above using the microfluidic instrument.

They were prepared in selected buffers and screened in-vitro for positive cell GFP transfection and expression.

The selected buffers used:

1) 10 mM Citrate Buffer, pH 4, CB
2) Tris-EDTA Buffer, pH 7.4
3) PBS, pH 7.5

4) 20 mM HEPES-5% Dextrose, pH 7.5, HBD5%

5) 20 mM MES, pH 6.1.

Figure 7:
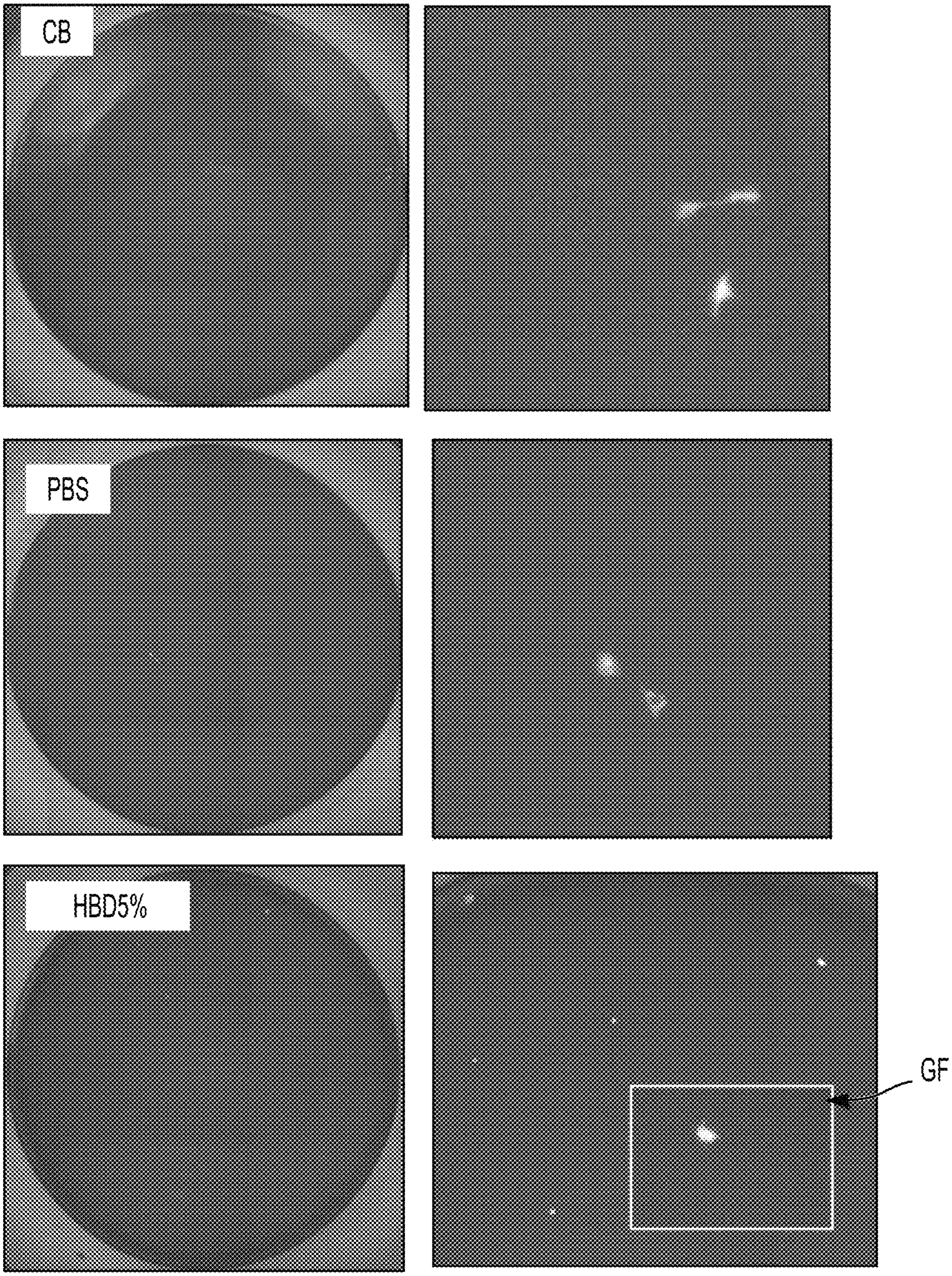
FIGS. 7-8 show the transfection of HEK293 cells (by way of with LNPs of various ratios, dose amounts, and buffers made in accordance with the present disclosure.
Figure 8:
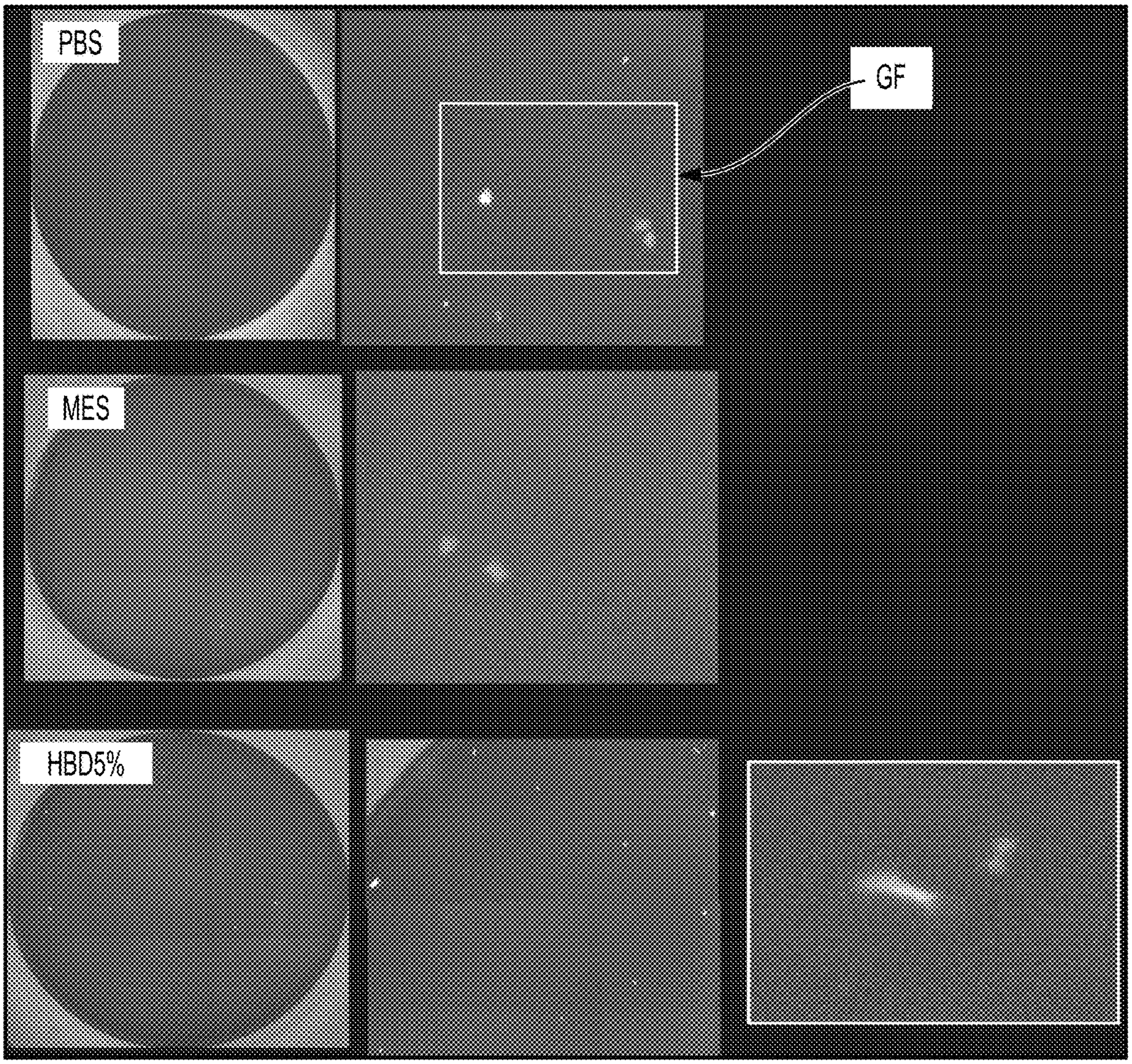

Several of the LNPs of various ratios, dose amounts, and buffers were able to transfect HEK293 cells. The positive Green Fluorescent cells (as demonstrated in FIG. 7 (PEOZ 2.6K 9p NMPCA—1:7 w/w=N/P ratio of 3.9 (4×—left, 20×—right)) and FIG. 8 (PEOZ 2.3K 1.2p (Choline-Iodide)-3-proprionate—1:70 w/w=N/P ratio of 8.8 (4×—left, 20×—right)) by GF) indicate cellular uptake and expression.

Example 42. Gel Shift Assay for saRNA/PPOZ-OH 2.6K NMPCA Polyplexes

Gel shift assay was performed to assess the binding ability of ionizable PPOZ 2.6K NMPCA polymers (Examples 32-34) to form complexes with saRNA. Various ratios of PPOZ 2.6K NMPCA to saRNA (w/w) were prepared and analyzed on the agarose gel (E-Gel EX Agarose gel, Invitrogen).

The self-amplifying RNA (saRNA) was the Enhanced Green Fluorescent Protein encoded with the EGFP gene from the jellyfish, Aequorea victoria (Creative Biogene, PMSAR-0001). The single-stranded RNA has 8528 bp and the EGFP has a molecular weight of 27 kDa. The supplied solution of 1.106 μg/μL in water, was diluted with 10 mM sodium acetate buffer, pH 4.5, to prepare a solution of 0.05 μg/μL. A stock solution containing ionizable PPOZ 2.6K NMPCA polymers was prepared in sterile filtered WFI quality water (OmniPur Millipore) at 1.0 μg/μL and then diluted with water to various concentrations from 0 to 1.0 μg/μL.

To evaluate the amount of PPOZ polymers that completely binds to saRNA and retards the saRNA mobility, 0.05 μg/μL of saRNA was mixed with various concentrations of PPOZ polymers ranging from 0 to 0.5 μg/μL or 1.0 μg/μL. The saRNA and PPOZ polymer were mixed in a 1:1 volume ratio. The resulting mixture was incubated for 10 min at room temperature and 0.5 μg of saRNA in polyplex was loaded into precast 1% agarose gel. Electrophoresis was set up and run for 10 min. saRNA retardation was analyzed on a gel imaging system (E-Gel Power Snap Electrophoresis System, Invitrogen) to detect the shift of saRNA band.

Figure 9A:
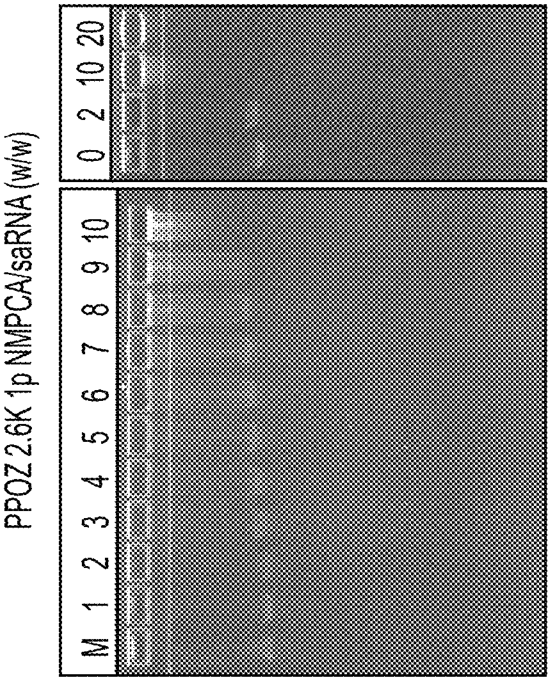
FIGS. 9A-9C show payload binding to cationic POZ at increasing polymer concentration in accordance with embodiments of the present disclosure.
Figure 9B:
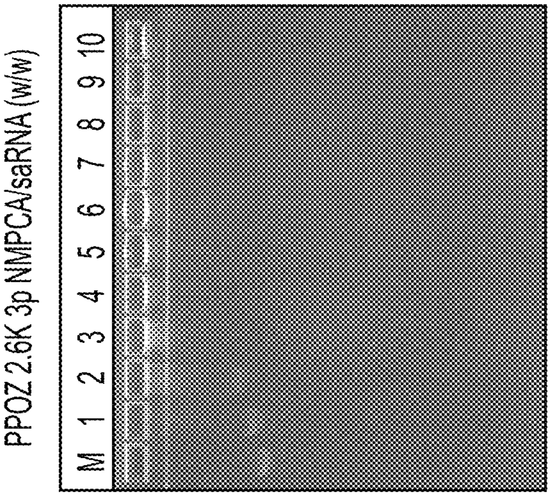
Figure 9C:
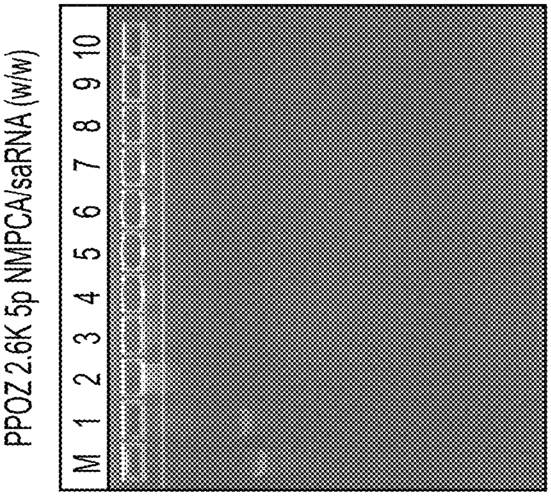

FIGS. 9A-9C show saRNA binding to PPOZ 2.6K NMPCA polymers as increasing each polymer concentration. The first lane M contained naked saRNA and was run as a control. Complete binding of saRNA was observed higher than PPOZ 2.6K 1p, 3p, 5p NMPCA to saRNA ratios of 10:1, 3:1, and 2:1 (w/w), respectively.

Example 43. Preparation of Lipid Nanoparticles Containing saRNA and PPOZ-OH 2.6K NMPCA The self-amplifying RNA (saRNA) was the Enhanced Green Fluorescent Protein encoded with the EGFP gene from the jellyfish, Aequorea victoria (Creative Biogene, PMSAR-0001). The single-stranded RNA has 8528 bp and the EGFP has a molecular weight of 27 kDa. The supplied solution of 1.106 μg/μL in water, was diluted with 10 mM sodium acetate buffer, pH 4.5, to prepare a solution of appropriate concentration. A 10 mL sterile disposable BD syringe was filled with 1.0 mL of the aqueous solution of the saRNA.

Each stock solution of PPOZ-OH 2.6K NMPCA (from Examples 32-34), 1,2-distearoyl-sn-glycero-3-phosphocholine (DSPC, Bachem 4005619), cholesterol (VWR 0433) and PEOZ 2K DMA (as described in co-pending U.S. patent application Ser. No. 17/665,190, filed Feb. 4, 2022, the entire disclosure of which is incorporated by reference herein) were prepared in ethanol (ENID Millipore EX0276-4). The stock solutions were mixed so that the two concentrations of lipid mixture were prepared as high lipid concentration, 10 mg/mL, and low lipid concentration, 1.5-3.5 mg/mL, with varying mol % of DSPC and N/P ratios as shown in Table 3 below.

TABLE 3

| Formulation ID | PPOZ | PPOZ/DSPC/Chol/DMA-POZ 2K | DSPC mol % | PPOZ/saRNA w/w ratios | N/P ratios |
|---|---|---|---|---|---|
| D-1 p | PPOZ 1 p | 3.4:19.5:75.1:2.0 | 20 | 10:1 | 1.09 |
| D-3 p | PPOZ 3 p | 0.9:20.0:77.1:2.0 | 20 | 3:1 | 0.83 |
| D-5 p | PPOZ 5 p | 0.5:20.1:77.4:2.0 | 20 | 2:1 | 0.77 |
| E-1 p | PPOZ 1 p | 3.0:35.2:59.8:2.0 | 35 | 10:1 | 1.09 |
| E-3 p | PPOZ 3 p | 0.8:36.0:61.2:2.0 | 35 | 3:1 | 0.83 |
| E-5 p | PPOZ 5 p | 0.5:36.1:61.4:2.0 | 35 | 2:1 | 0.77 |
| F-1 p | PPOZ 1 p | 2.1:58.5:37.3:2.0 | 60 | 10:1 | 1.09 |
| F-3 p | PPOZ 3 p | 0.5:59.5:37.9:2.0 | 60 | 3:1 | 0.83 |
| F-5 p | PPOZ 5 p | 0.3:59.6:38.0:2.0 | 60 | 2:1 | 0.77 |

A 5 mL sterile disposable BD syringe was filled with 0.3 mL of the organic solution of the lipid mix containing the ionizable PPOZ 2.6K NMPCA polymer, DSPC, Cholesterol and PEOZ 2K DMA.

Figure 10:
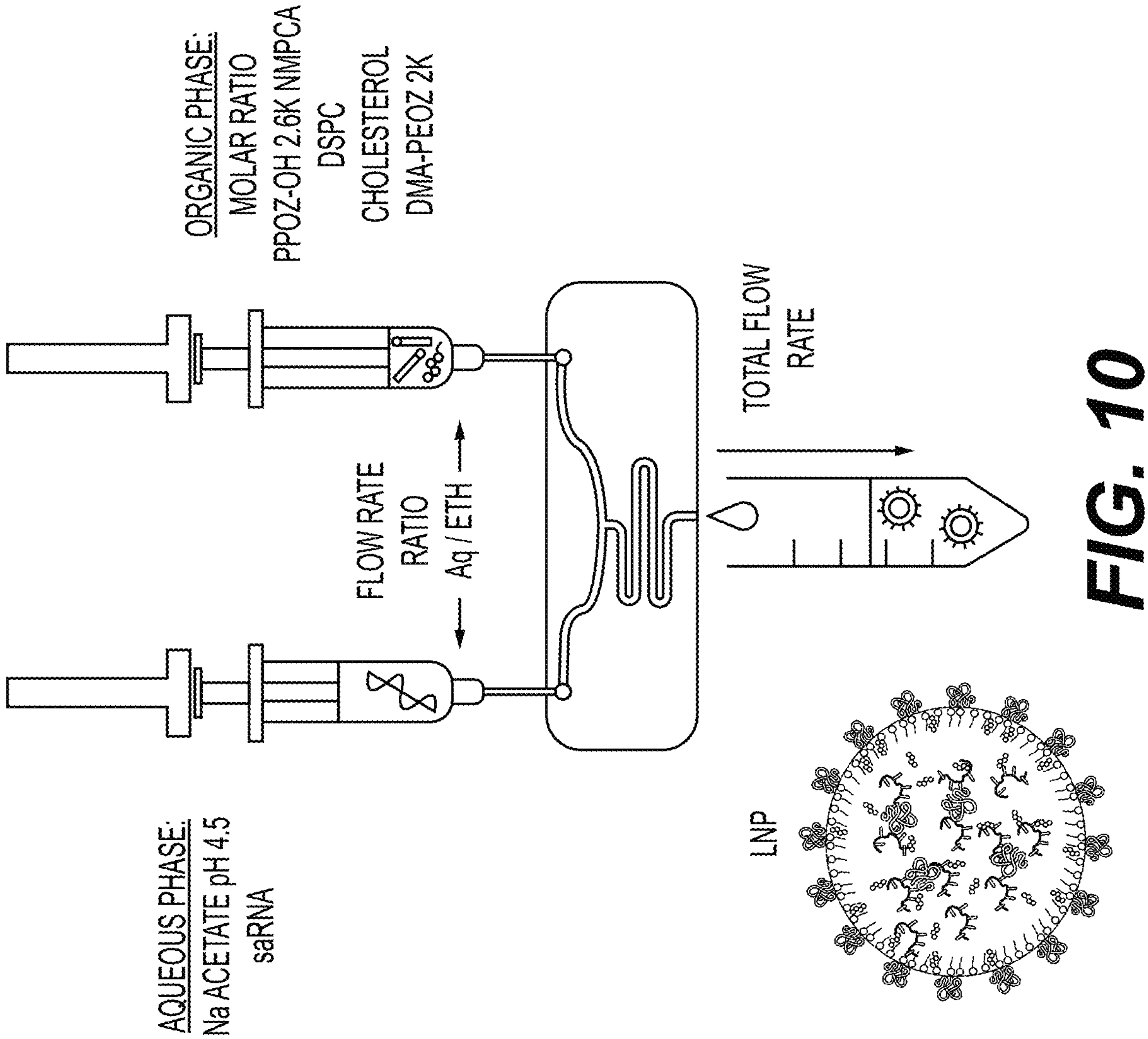
FIG. 10 shows a microfluidic mixing system suitable for mixing a payload, lipids, and cationic POZ in accordance with embodiments of the present disclosure.

As shown in FIG. 10, a microfluidic mixing system equipped with a cartridge (Nunchuck, Unchained Labs) was used to mix the saRNA and the lipids with ionizable PPOZ 2.6K NMPCA polymer. Both syringes were loaded on the instrument and set to dispense at a ratio of 3 parts aqueous to 1 part. Flow rate of 20 mL/min was programmed into the instrument and set to collect 0.25 mL fractions of mixture. Each fraction was diluted 10 times with 25 mM Tris-HCl, pH 7.4, and then incubated for an hour to reduce ethanol content in the formulations.

Figure 11B:
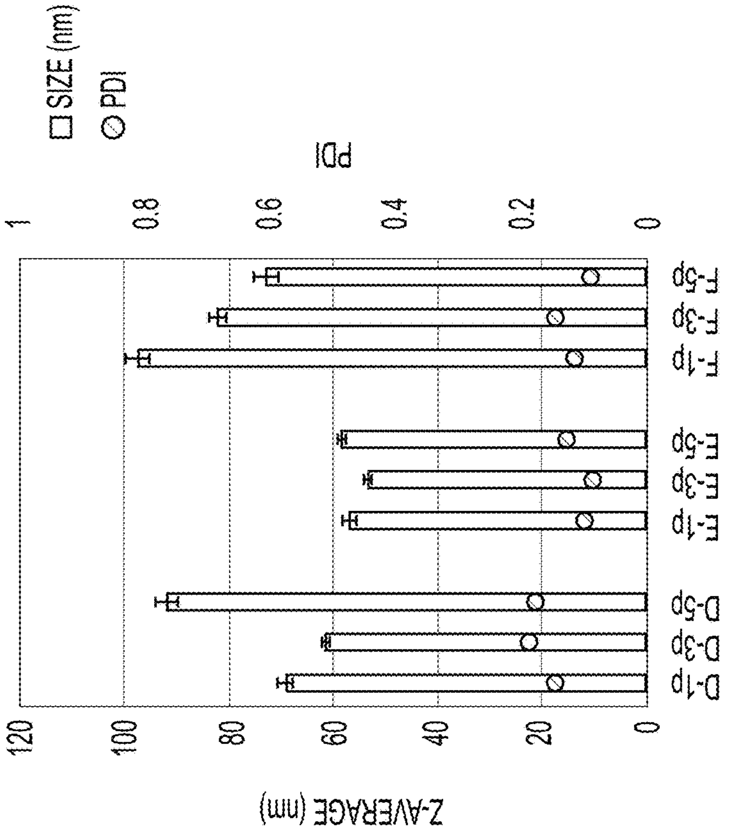
FIGS. 11A-11B shows particle size of LNPs formed in accordance with embodiments of the present disclosure.
Figure 11A:
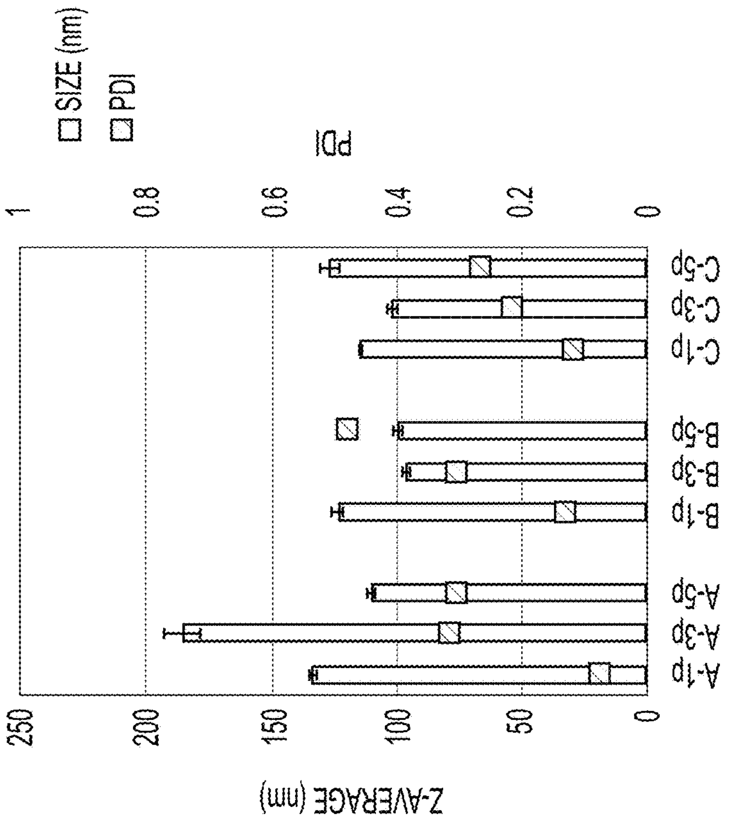
Figure 12B:
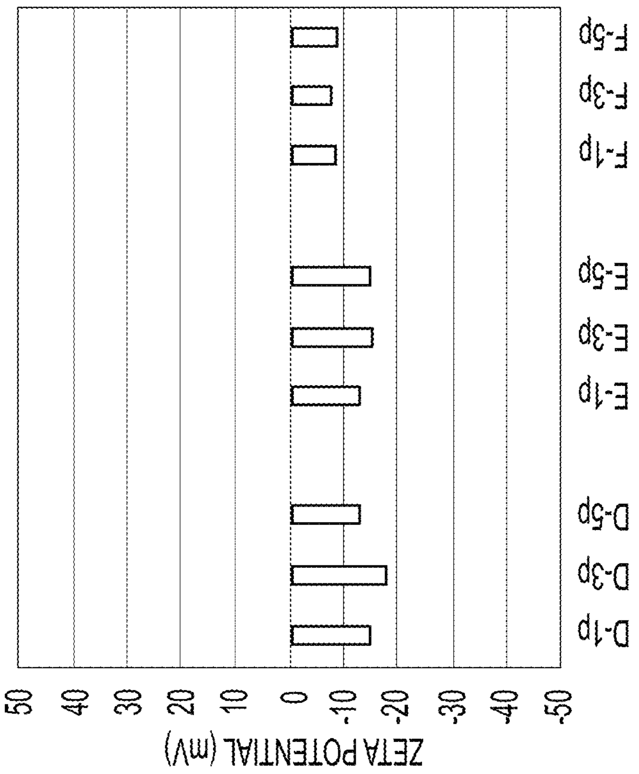
FIGS. 12A-12B shows the zeta potential of LNPs formed in accordance with embodiments of the present disclosure.
Figure 12A:
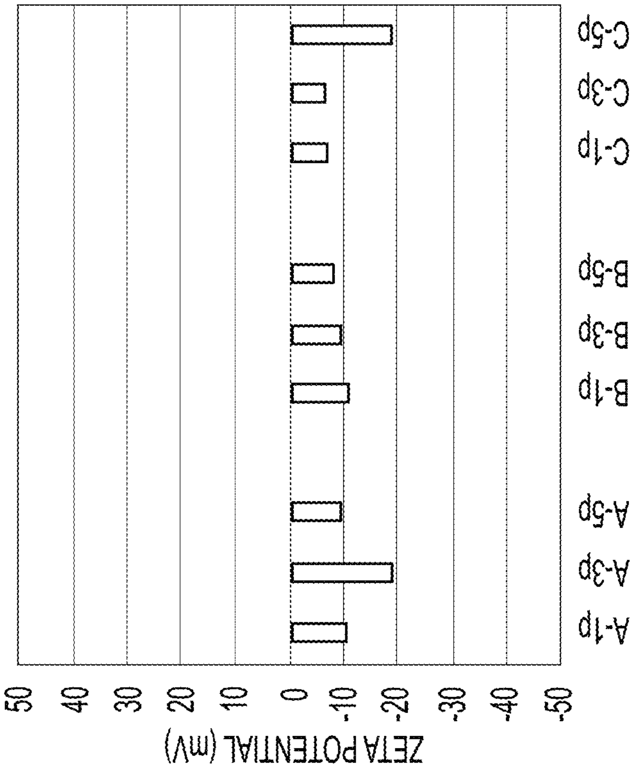

The size of the formulated PPOZ LNPs was measured using dynamic light scattering (DLS) (Zetasizer Ultra, Malvern Panalytical). FIGS. 11A and 11B show the particle size of the PPOZ LNP formulations averaged after three measurements ranged between 60-150 nm with low PDI. The zeta potential of the PPOZ LNPs was measured using a Zetasizer Ultra (Malvern Panalytical) with electrophoretic light scattering capabilities. The PPOZ LNP samples were diluted eight times with 25 mM Tris-HCl buffer to measure the zeta potential. FIGS. 12A and 12B shows the zeta potential recorded after measurements ranged from −8 to −18 mV.

Example 44. Preparation of saRNA/PPOZ-OH 2.6K NMPCA Polyplexes

A stock solution containing ionizable PPOZ-OH 2.6K NMPCA polymers (Examples 26-28), was used in this example. A working solution was prepared in ethanol at a concentration of 10.0 mg/mL and then diluted to 6.8-8.8 mg/mL. The EGFP saRNA solution of 1.106 μg/μL in water was diluted with 10 mM sodium acetate, pH 4.5, to prepare a solution of 0.04-0.15 mg/mL to make N/P ratio of 8.

The PPOZ 2.6K NMPCA in ethanol was mixed with saRNA in 10 mM Na Acetate, pH 4.5 at a ratio of 3 parts aqueous to 1 part organic using a pipette via hand mixing and then diluted 10 times with 25 mM Tris-HCl, pH 7.4. The resulting mixture was incubated for one hour at room temperature to reduce ethanol content in the polyplexes.

Figure 13:
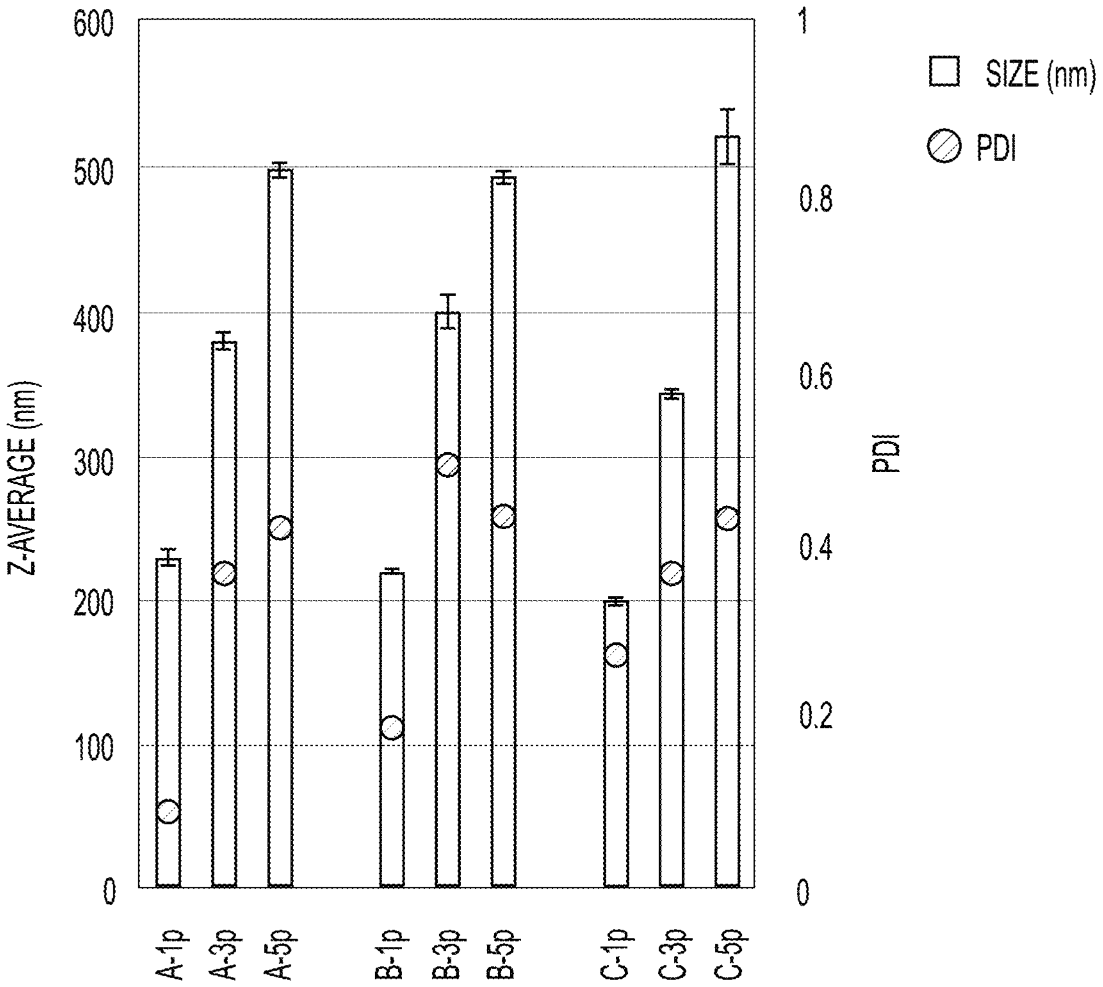
FIG. 13 shows particle size of polyplexes formed in accordance with embodiments of the present disclosure.

The size of polyplexes was measured using dynamic light scattering (DLS) (Zetasizer Ultra, Malvern Panalytical). FIG. 13 shows the particle size of polyplexes averaged after three measurements ranged between 200-500 nm.

Examples 45-48. Preparation of POZ Spermine

The examples below demonstrate POZ Spermine made from the various preceding examples. For example, from PEOZ-NHS 2K (Example 1), the synthesis of PEOZ 2K Spermine amide:

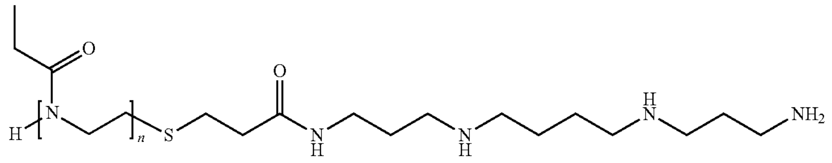

PEOZ 2K Spermine amide

From PEOZ-Propargylamide 2K (Example 4), the synthesis of PEOZ 2K Triazole Spermine:

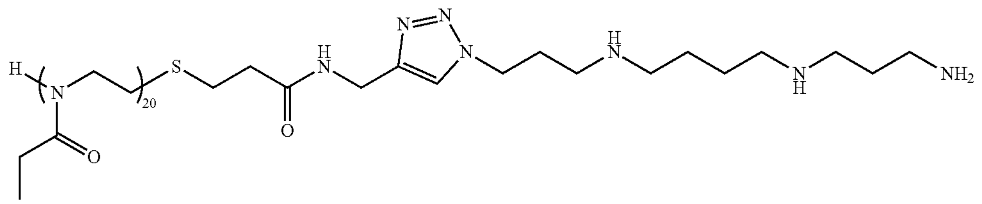

PEOZ 2K Triazole Spermine

From $P[(EOZ)_m(PtynOZ)_n]$-Propargylamide 2K (Example 5), the synthesis of PEOZ 2K (n+1) Triazole Spermine:

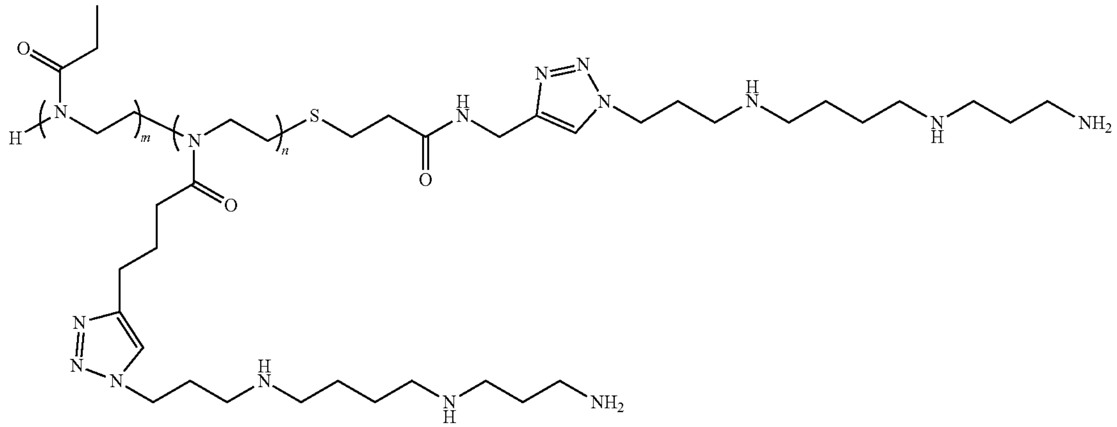

PEOZ 2K (n + 1) Triazole Spermine

From PEOZ-Pip-acid 1.2 k 4p (Example 3), the synthesis of PEOZ 2K 5P (Glycolic Spermine amide) Ester:

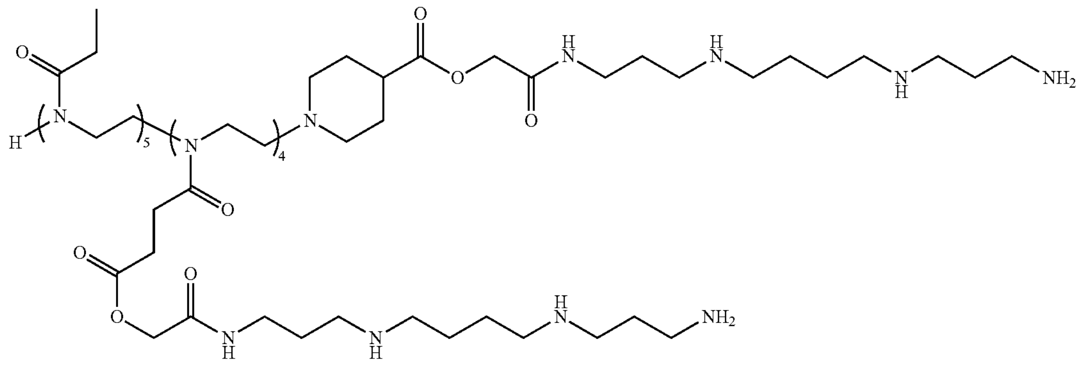

PEOZ 2K 5p (Glycolic Spermine amide) Ester

Example 45. Synthesis of PEOZ 2K Spermine Amide

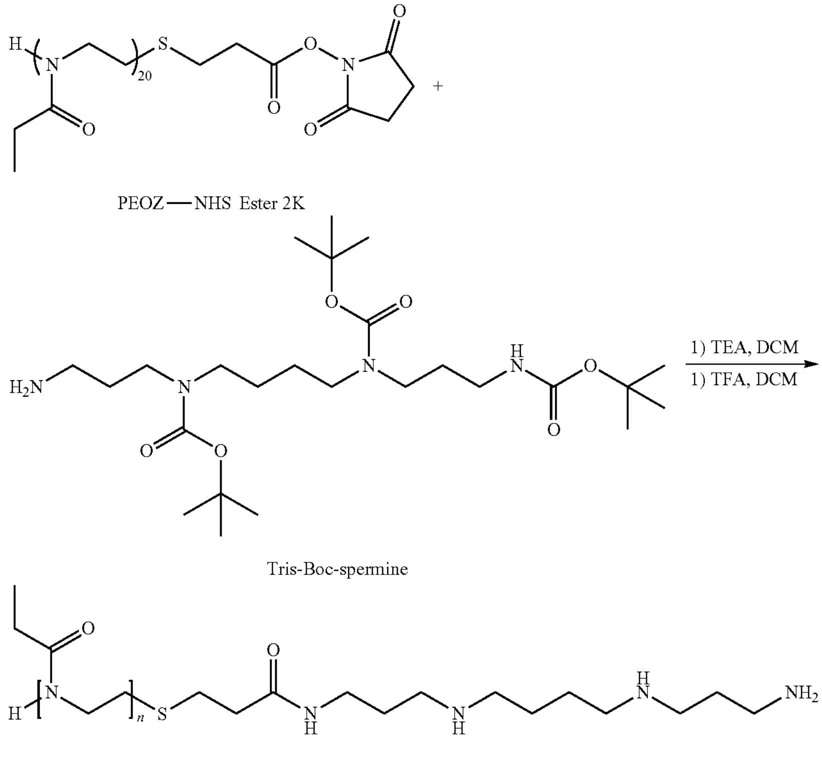

PEOZ—NHS Ester 2K

Tris-Boc-spermine

PEOZ 2K Spermine amide

PEOZ-NHS (200.0 mg, 0.10 mmol, 2K Da, 1.0 equiv) and Tris-Boc-spermine (50.3 mg, 0.10 mmol, 1.0 equiv) were added into a 2-dram vial. 0.1N boric acid (2 mL) was added and the mixture was stirred to dissolve. While stirring, pH of the solution was adjusted to 8.5 by the dropwise addition of 0.1N NaOH(aq) solution. After the stirring overnight, the resulting mixture (pH 8.42) was extracted using DCM and precipitated by addition into diethyl ether. The resulting precipitate was filtered and dried to give PEOZ 2K Tris-Boc-spermine.

The conjugation of tris-Boc-spermine was verified by $^1$H NMR (Varian, 500 MHz, 10 mg/mL DMSO-d6). Besides the polymer related backbone peaks, additional peaks for the tris-Boc-spermine moiety were identified.

Boc-deprotection was performed by treatment with TFA (15 eq) in DCM. The resulting reaction mixture was concentrated using a rotary evaporator. The residue was redissolved in DCM and precipitated by adding into diethyl ether. The precipitate was filtered and dried in vacuo to give the desired PEOZ 2K spermine amide.

The deprotection reaction was verified by $^1$H NMR (Varian, 500 MHz, 10 mg/mL DMSO-d6) that showed the disappearance of peak corresponding to the -Boc group.

Example 46. Synthesis of PEOZ 2K Triazole Spermine

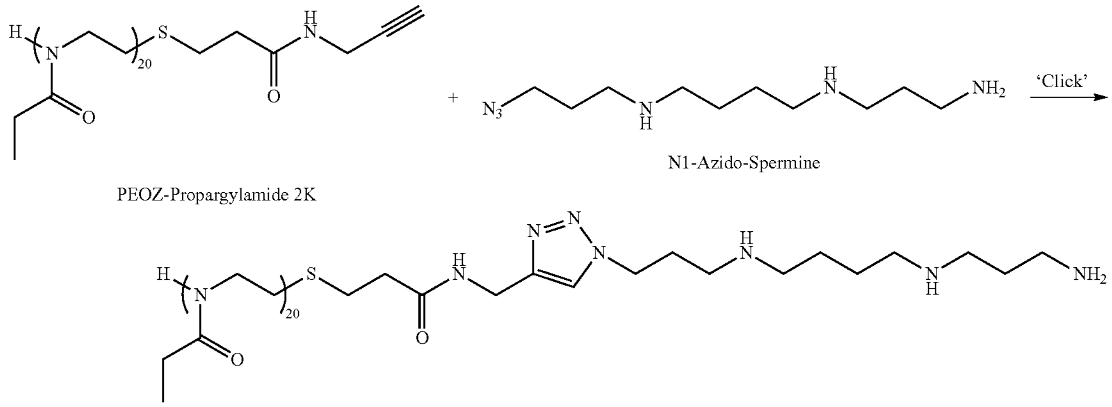

PEOZ-Propargylamide 2K

N1-Azido-Spermine

PEOZ 2K Triazole Spermine

To a solution of PEOZ-Propargylamide 2K (1.0 equiv, Mn 2000 Da) and N1-azido-spermine (1.0 eq) in THE were added CuI (0.4 equiv) and TEA (1.5 equiv). The resulting mixture was stirred for 5 minutes at room temperature and then allowed to stir for 18 hours at 50° C. to give a cloudy yellow solution. After cooling down to room temperature, the reaction mixture was quenched by adding 0.1N aqueous HCl followed by stirring for 5 minutes. The mixture was passed through the Dowex® M4195 column and then THE was removed from the filtrate using a rotary evaporator. The resulting aqueous solution was stirred with of dichloromethane using NaCl (5 w/v % of water volume). The organic phase was collected, dried over $Na_2SO_4$, filtered, and concentrated. The residue was dissolved in DCM and precipitated by adding into diethyl ether, filtered, and dried in vacuo to give the desired product.

The attachment of N1-azido-spermine was verified by 1H NMR (Varian, 500 MHz, 10 mg/mL DMSO-d6) that showed the peaks at 5.59 ppm (m, 1H, triazole-CH2NHC(=O)— and 8.00 ppm (s, 1H, triazole ring, resulted by 'click' reaction), besides the usual polymer backbone peaks.

Example 47. Synthesis of PEOZ 2K (n+1) Trizaole Spermine

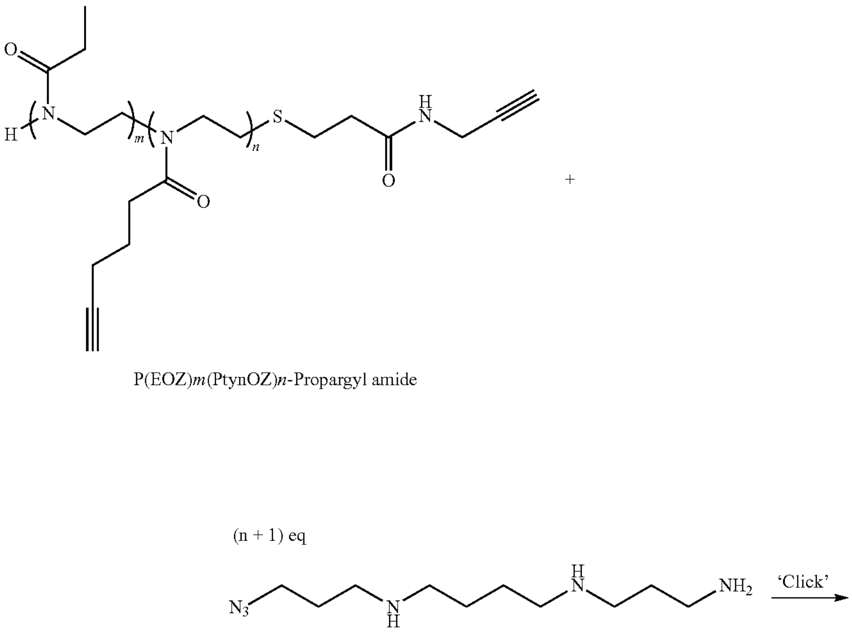

P(EOZ)*m*(PtynOZ)*n*-Propargyl amide

N1-Azido-Spermine

-continued

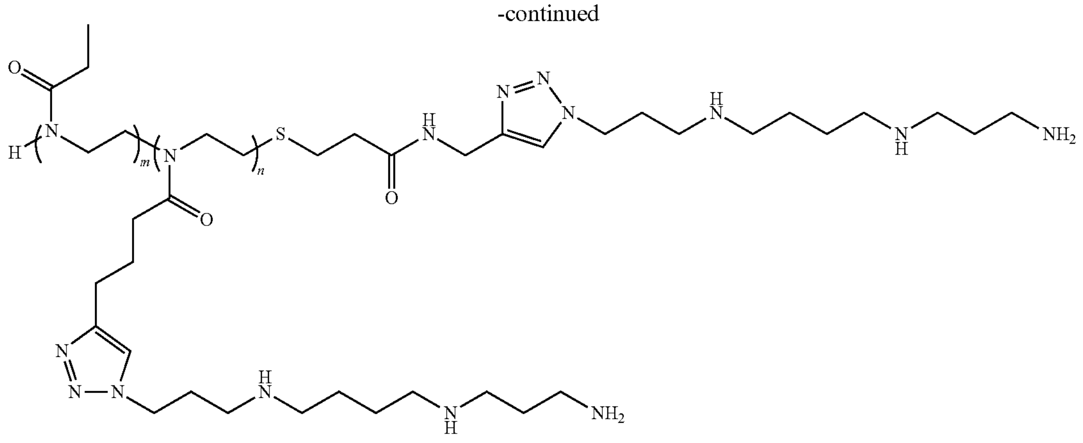

PEOZ 2K (n + 1) Triazole Spermine

To a solution of $(EOZ)_m(PtynOZ)_n$-propargylamide (1.0 equiv, Mn 2000 Da, where m=13 and n=7) and (N-methyl-4-piperidyl)-3-azidopropionate (n+1 eq) in THE were added CuI (0.4×(n+1) equiv) and TEA (1.5×(n+1) equiv). The resulting mixture was stirred for 5 minutes at room temperature and then allowed to stir for 18 hours at 50° C. to give a cloudy yellow solution. After cooling down to room temperature, the reaction mixture was quenched by adding 0.1N aqueous HCl followed by stirring for 5 minutes. The mixture was passed through the Dowex® M4195 column and then THE was removed from the filtrate using a rotary evaporator. The resulting aqueous solution was stirred with of dichloromethane using NaCl (5 w/v % of water volume). The organic phase was collected, dried over Na2SO4, filtered, and concentrated. The residue was dissolved in DCM and precipitated by adding into diethyl ether, filtered, and dried in vacuo to give the desired product.

The attachment of N1-azido-spermine was verified by $^1H$ NMR (Varian, 500 MHz, 10 mg/mL DMSO-$d_6$) that showed the peaks at 5.59 ppm (m, 1H, triazole-$CH_2NHC(=O)$— and 8.00 ppm (s, 1H, triazole ring, resulted by 'click' reaction), besides the usual polymer backbone peaks.

Example 48. Synthesis of PEOZ 2K 5P (Glycolic Spermine Amide) Ester

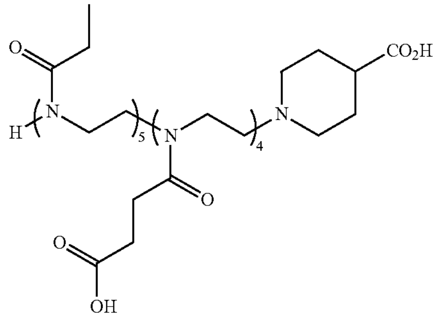

PEOZ-Pip-acid 1.2K 4 P acid

+

5 eq

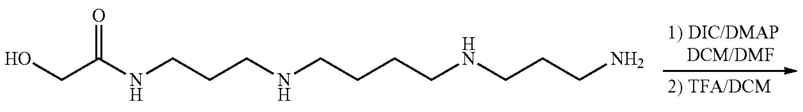

Glycolic Spermine amide

-continued

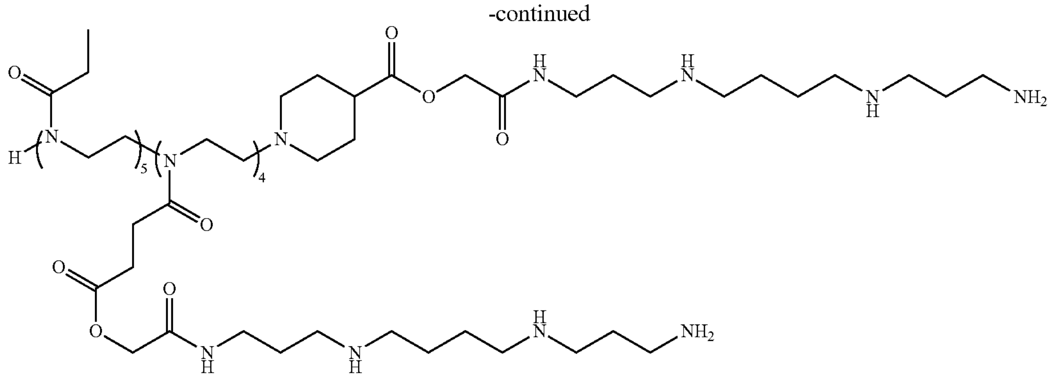

PEOZ 2K 5p (Glycolic Spermine amide) Ester

A reaction flask was charged with $(EOZ)_5(PrAcidOZ)_4$-Pip-COOH 1.2K (1.0 equiv), Glycolic Spermine amide (6.0 equiv), and DMAP (0.1 equiv) followed by a stir bar and DMF under an atmosphere of argon. After the addition of DIC (6.0 equiv), the mixture was allowed to stir for 18 hours at room temperature. The reaction mixture was filtered using a syringe filter and the filtrate was concentrated down followed by the precipitation by addition into diethyl ether. The ether solution was decanted and the residue was stirred with a freshly added diethyl ether. The white precipitate was filtered, collected, and dried in vacuo to give the desired product as a white crystalline.

The attachment of Glycolic Spermine amide was verified by $^1H$ NMR (Varian, 500 MHz, 10 mg/mL DMSO-d6) that showed the peaks corresponding to the glycolic $CH_2$ and spermine moiety.

The cationic POZ, LNPs and polyplexes, and pharmaceutical compositions described and claimed herein are not to be limited in scope by the specific embodiments herein disclosed, since these embodiments are intended as illustrations of several aspects of the disclosure. Any equivalent embodiments are intended to be within the scope of this disclosure. Indeed, various modifications of the formulas and structures in addition to those shown and described herein will become apparent to those skilled in the art from the foregoing description. Such modifications are also intended to fall within the scope of the appended claims. All patents and patent applications cited in the foregoing text are expressly incorporated herein by reference in their entirety. Any section headings herein are provided only for consistency with the suggestions of 37 C.F.R. § 1.77 or otherwise to provide organizational queues. These headings shall not limit or characterize the invention(s) set forth herein.

What is claimed is:

1. A lipid nanoparticle comprising:

a cationic POZ;

a helper lipid;

a polymer lipid; and a sterol lipid, wherein the cationic POZ is selected from the group consisting of one cationic POZ of Formulae I-IV:

$$R-POZ_1-\text{cation} \quad (I)$$

wherein R comprises an initiating group and $POZ_1$ comprises a polyoxazoline polymer;

$$R-\{[NCH_2CH_2]_n[N(COR_2)CH_2CH_2]_m\}_a-T \quad (II)$$
cation wherein R comprises an initiating group, n ranges from 1 to 10, $R_2$ is independently selected for each repeating unit from an unsubstituted or substituted alkyl, alkenyl, aralkyl, heterocyclylalkyl, or active functional group, m ranges from 1 to 100, a is ran, which indicates a random copolymer, or block, which indicates a block copolymer, and T comprises a terminating group;

$$R-\{[NCH_2CH_2]_n[N(COR_2)CH_2CH_2]_m\}_a-T\text{-cation} \quad (III)$$
cation wherein R comprises an initiating group, n ranges from 1 to 10, $R_2$ is independently selected for each repeating unit from an unsubstituted or substituted alkyl, alkenyl, aralkyl, heterocyclylalkyl, or active functional group, m ranges from 1 to 100, a is ran, which indicates a random copolymer, or block, which indicates a block copolymer, and T comprises a terminating group; and $$R-\{[NCH_2CH_2]_n[N(COR_2)CH_2CH_2]_m\}_a-T\text{-cation} \quad (IV)$$
cation wherein R comprises an initiating group, n ranges from 1 to 10, $R_2$ is independently selected for each repeating unit from an unsubstituted or substituted alkyl, alkenyl, aralkyl, heterocyclylalkyl, or active functional group, m ranges from 1 to 100, a ranges from 3 to 20, and T comprises a terminating group.

2. The lipid nanoparticle of claim 1, wherein the lipid nanoparticle comprises about 0.1 percent to about 10 percent cationic POZ, about 30 percent to about 80 percent sterol lipid, about 0.5 percent to about 20 percent polymer lipid, and about 15 percent to about 65 percent helper lipid.

3. The lipid nanoparticle of claim 2, wherein the lipid nanoparticle comprises about 35 percent to about 78 percent sterol lipid and about 18 percent to about 63 percent helper lipid.

4. The lipid nanoparticle of claim 2, wherein the lipid nanoparticle comprises about 0.3 percent to about 5 percent cationic POZ.

5. The lipid nanoparticle of claim 1, wherein the lipid nanoparticle comprises about 30 percent to about 70 percent cationic POZ, about 30 percent to about 50 percent sterol lipid, about 0.5 percent to about 20 percent polymer lipid, and about 5 percent to about 15 percent helper lipid.

6. The lipid nanoparticle of claim 1, wherein the polymer lipid is a POZ-lipid of Formula V:

$$R—POZ_2—L—Lipid \qquad (V)$$

wherein R comprises an initiating group, $POZ_2$ comprises poly(oxazoline),

L comprises a linking group, and

Lipid comprises a non-charged lipid comprising at least one hydrophobic moiety.

7. The lipid nanoparticle of claim 6, wherein the linking group is physiologically degradable.

8. A lipid nanoparticle comprising:

a cationic POZ of Formula I $$R—POZ_1—cation \qquad (I)$$

wherein R comprises an initiating group and $POZ_1$ comprises a polyoxazoline polymer;

a helper lipid;

a polymer lipid; and a sterol lipid.

9. The lipid nanoparticle of claim 8, the polymer lipid is a POZ-lipid of Formula V:

$$R—POZ_2—L—Lipid \qquad (V)$$

wherein R comprises an initiating group, $POZ_2$ comprises poly(oxazoline),

L comprises a linking group, and

Lipid comprises a non-charged lipid comprising at least one hydrophobic moiety.

10. The lipid nanoparticle of claim 9, wherein the linking group is physiologically degradable.

11. The lipid nanoparticle of claim 8, wherein the lipid nanoparticle comprises about 0.1 percent to about 10 percent cationic POZ, about 30 percent to about 80 percent sterol lipid, about 0.5 percent to about 20 percent polymer lipid, and about 15 percent to about 65 percent helper lipid.

12. The lipid nanoparticle of claim 8, wherein the lipid nanoparticle comprises about 30 percent to about 70 percent cationic POZ, about 30 percent to about 50 percent sterol lipid, about 0.5 percent to about 20 percent polymer lipid, and about 5 percent to about 15 percent helper lipid.

13. A lipid nanoparticle comprising:

a cationic POZ of Formula II $$R-\{[\underset{\text{cation}}{\underset{|}{N}}CH_2CH_2]_n[N(COR_2)CH_2CH_2]_m\}_a—T \qquad (II)$$

wherein R comprises an initiating group, n ranges from 1 to 10, $R_2$ is independently selected for each repeating unit from an unsubstituted or substituted alkyl, alkenyl, aralkyl, heterocyclylalkyl, or active functional group, m ranges from 1 to 100, a is ran, which indicates a random copolymer, or block, which indicates a block copolymer, and T comprises a terminating group;

a helper lipid;

a polymer lipid; and a sterol lipid.

14. The lipid nanoparticle of claim 13, the polymer lipid is a POZ-lipid of Formula V:

$$R—POZ_2—L—Lipid \qquad (V)$$

wherein R comprises an initiating group, $POZ_2$ comprises poly(oxazoline),

L comprises a linking group, and

Lipid comprises a non-charged lipid comprising at least one hydrophobic moiety.

15. The lipid nanoparticle of claim 14, wherein the linking group is physiologically degradable.

16. The lipid nanoparticle of claim 13, wherein the lipid nanoparticle comprises about 0.1 percent to about 10 percent cationic POZ, about 30 percent to about 80 percent sterol lipid, about 0.5 percent to about 20 percent polymer lipid, and about 15 percent to about 65 percent helper lipid.

17. The lipid nanoparticle of claim 13, wherein the lipid nanoparticle comprises about 30 percent to about 70 percent cationic POZ, about 30 percent to about 50 percent sterol lipid, about 0.5 percent to about 20 percent polymer lipid, and about 5 percent to about 15 percent helper lipid.

* * * * *